US012440581B2

(12) United States Patent
Lavis et al.

(10) Patent No.: US 12,440,581 B2
(45) Date of Patent: Oct. 14, 2025

(54) FLUOROPHORES FOR SUPER-RESOLUTION IMAGING

(71) Applicant: HOWARD HUGHES MEDICAL INSTITUTE, Chevy Chase, MD (US)

(72) Inventors: Luke D. Lavis, Leesburg, VA (US); Qinsi Zheng, Ashburn, VA (US)

(73) Assignee: HOWARD HUGHES MEDICAL INSTITUTE, Chevy Chase, MD (US)

( * ) Notice: Subject to any disclaimer, the term of this patent is extended or adjusted under 35 U.S.C. 154(b) by 333 days.

(21) Appl. No.: 17/027,286

(22) Filed: Sep. 21, 2020

(65) Prior Publication Data

US 2021/0085805 A1 Mar. 25, 2021

Related U.S. Application Data

(60) Provisional application No. 62/902,708, filed on Sep. 19, 2019.

(51) Int. Cl.

| | |
|---|---|
| ***A61K 49/00*** | (2006.01) |
| ***C07D 311/04*** | (2006.01) |
| ***C07F 7/08*** | (2006.01) |
| ***G01N 21/64*** | (2006.01) |

(52) U.S. Cl.

CPC ........ *A61K 49/0021* (2013.01); *C07D 311/04* (2013.01); *C07F 7/0816* (2013.01); *G01N 21/64* (2013.01); *G01N 2223/406* (2013.01)

(58) Field of Classification Search

CPC ............................ C12N 15/113; C12N 5/063; C12N 2310/141; A61K 8/606; A61K 35/36

See application file for complete search history.

(56) References Cited

U.S. PATENT DOCUMENTS

| | | | | |
|---|---|---|---|---|
| 5,164,385 | A | 11/1992 | Cliffe et al. | |
| 5,194,439 | A | 3/1993 | Cliffe et al. | |
| 5,555,861 | A | 9/1996 | Mayr et al. | |
| 9,933,417 | B2 | 4/2018 | Lavis et al. | |
| 2014/0172396 | A1 | 6/2014 | Albarello | |
| 2018/0291265 | A1 * | 10/2018 | Schwarz | ................ C09K 11/06 |

FOREIGN PATENT DOCUMENTS

| | | | | |
|---|---|---|---|---|
| CN | 111334067 B | * 10/2021 | | ............. C09B 57/00 |
| EP | 0395244 A1 | 10/1990 | | |
| GB | 2247887 A | 3/1992 | | |
| WO | 2004/087687 A1 | 10/2004 | | |
| WO | 2007/105053 A2 | 9/2007 | | |
| WO | 2007/133637 A2 | 11/2007 | | |
| WO | 2010/149190 A1 | 12/2010 | | |
| WO | 2012/045196 A1 | 4/2012 | | |
| WO | 2012/125983 A1 | 9/2012 | | |
| WO | 2013/010974 A2 | 1/2013 | | |
| WO | 2013/090929 A1 | 6/2013 | | |
| WO | WO-2015153813 A1 | * 10/2015 | | ........... C07D 205/06 |

OTHER PUBLICATIONS

European Patent Office, Extended European Search Report cited in corresponding Application No. EP15774408, mailed Aug. 23, 2017.
Bernhard Witulski, et al. "Palladiuim-Catalyzed N-Arylation Reactions with Aziridine and Azetidine," Synthesis, ,01. 2007, No. 2, Jan. 1, 2007, pp. 243-250.
I.A. Cliffe, et al. "7-amino--5,6,7,8-tetrahydroquinolines. Preparation from 5,6-dihydroquinoline and nitrogen nucleophiles," Tetrahedron Letters, vol. 32, No. 46, Nov. 11, 1991, pp. 6789-6792.
Rebecca B. White, et al.. "The effect of RPR 102341 on theophylline metabolism and phenacetin O-deethylase activity in human liver microsomes," Jan. 1, 1997.
Jonathan B. Grimm, et al. "A general method 4-6,9-15 to improve fluorophores for live-cell and single-molecule microscopy," Nature Methods, vol. 12, No. 3, Jan. 19, 2015, pp. 244-250.
WIPO, International Preliminary Report on Patentability issued in international application No. PCT/US15/23953 on Oct. 4, 2016.

* cited by examiner

*Primary Examiner* — Robert S Cabral
(74) *Attorney, Agent, or Firm* — Stites & Harbison, PLLC; Mandy Wilson Decker

(57) ABSTRACT

The presently-disclosed subject matter includes fluorescent compounds of the following formula:

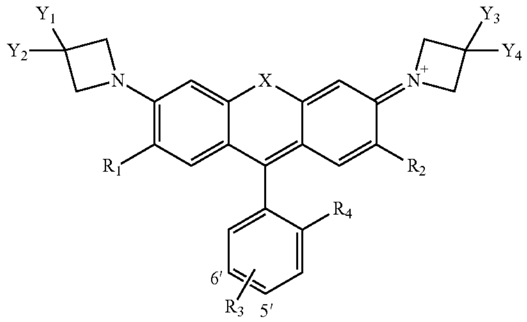

The compounds can be used as probes, dyes, tags, and the like. The presently-disclosed subject matter also includes kits comprising the same as well as methods for using the same to detect a target substance.

24 Claims, 15 Drawing Sheets

11
12: R = Boc
8: R = H 13
14
15
16
$8_{HTL}$ 19
29
10

24
30: R = t-Bu
31: R = H $7_{HTL}$: X = H
$10_{HTL}$: X = H
$7_{STL}$: X = H
$10_{STL}$: X = H $10_{HST}$ $10_{TXL}$ $10_{PEP}$

1
*off state*

1
*on state*

32
*off state*

32
*on state*

24: R = t-Bu
33: R = H
34
35
36: R = t-Bu
37: R = H
38

| ligand | X | Y | $NR_2$ | $\Delta A/A_0$ | $\Delta\Phi/\Phi_0$ |
|---|---|---|---|---|---|
| $1_{HTL}$ | $Si(CH_3)_2$ | H |  | 6.5 | 4.8 |
| $2_{HTL}$ | $Si(CH_3)_2$ | H |  | 21 | 9.8 |
| $3_{HTL}$ | $Si(CH_3)_2$ | H |  | 112 | 66 |
| $4_{HTL}$ | $C(CH_3)_2$ | H |  | 0.11 | 1.8 |
| $5_{HTL}$ | $C(CH_3)_2$ | H |  | 78 | 98 |
| $6_{HTL}$ | O | H |  | 0.032 | 0.65 |
| $7_{HTL}$ | O | H |  | 0.50 | 1.6 |
| $8_{HTL}$ | $Si(CH_3)_2$ | H |  | 6.8 | 8.7 |
| $9_{HTL}$ | O | F |  | 0.015 | 2.7 |
| $10_{HTL}$ | O | F |  | 15 | 8.9 |

$1_{TXL}$ $7_{TXL}$

FLUOROPHORES FOR SUPER-RESOLUTION IMAGING

TECHNICAL FIELD

The presently-disclosed subject matter relates to fluorescent compounds. In particular, the presently-disclosed subject matter relates to unique polycyclic chemical fluorophores, capable of emitting distinct colors, as well as method for making and using the same.

INTRODUCTION

Fluorescence microscopy enables the imaging of specific molecules inside living cells. This technique relies on the precise labeling of biomolecules with bright, photostable fluorescent dyes. Thus, small-molecule fluorophores are fundamental tools for biological research.[1-2]

The century-old[3-4] rhodamine dyes remain a very useful class of small-molecule fluorophores and serve as scaffolds for a variety of useful imaging probes: biomolecule labels, cellular stains, and environmental indicators.[5-6] This broad utility can be attributed to three key aspects of rhodamine dyes: (i) exceptional brightness and photostability; (ii) a broad palette of spectral properties accessed through straightforward structural modifications;[7-17] and (iii) the equilibrium between the colorless, nonfluorescent lactone (L) and the colored, fluorescent zwitterion (Z; equilibrium constant: $K_{L-Z}$). For example, the following illustrates the equilibrium between the lactone and zwitterion of Rhodamine B.

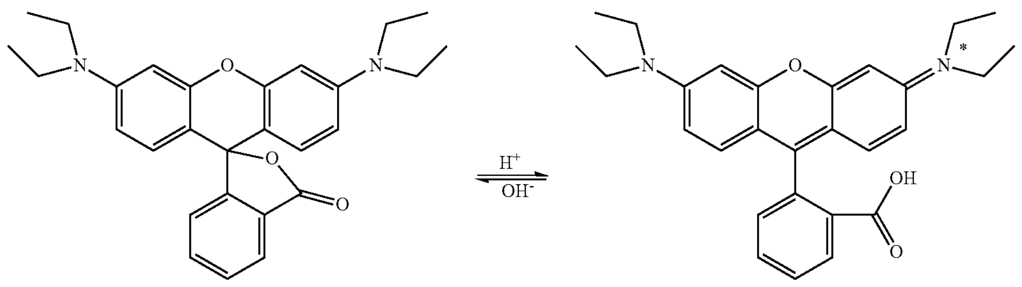

Nonfluorescent, Closed Lactone (L)

Fluorescent, Open Zwitterion (Z)

Tuning $K_{L-Z}$ lower—toward the lipophilic nonfluorescent lactone form—can improve cell-permeability[18] and yield 'fluorogenic' probes,[19] molecules that show substantial increases in absorbance and fluorescence upon labeling their cognate biomolecular targets.

The inherent fluorescence increase of fluorogenic ligands is particularly useful for biological imaging as such compounds remain quiescent until bound to their target, making them universal platforms for imaging and sensing.[20] This property can avoid the need to wash out excess label[18] and allow exchange of ligands to circumvent photobleaching.[21]

Early examples of fluorogenic molecules exploited solvatochromism,[22] pH sensitivity,[23-24] or quencher ejection[25-26] to translate the binding event into a change in fluorescence intensity.

More recently, the tetramethyl-Si-rhodamine ('SiR', 1; FIG. 1A and FIG. 7A (Top Panel)) has emerged as an remarkably versatile fluorogenic dye.[14] Compound 1 exhibits far-red wavelengths with an absorption maxima ($\lambda_{abs}$) of 643 nm, a fluorescence emission maxima ($\lambda_{em}$) of 662 nm, a modest fluorescence quantum yield ($\Phi$=0.41), and excellent photostability.

An important feature of SiR-based ligands is the relatively low $K_{L-Z}$ value (0.0034), which means the dye preferentially adopts the nonfluorescent lactone in aqueous solution (FIG. 1A). This results in a lower extinction coefficient ($\varepsilon$=28,200 $M^{-1}$ $cm^{-1}$) for the free dye in aqueous solution but makes SiR-based ligands highly cell-permeable due to the increased fraction of the lipophilic lactone. The lower $K_{L-Z}$ also makes SiR compounds fluorogenic as binding to biomolecular targets often shifts the equilibrium toward the fluorescent zwitterionic form (FIG. 1B).

The initial development of SiR-based ligands focused on fluorogenic ligands for genetically encoded self-labeling tags like the HaloTag and the SNAP-tag,[14, 25] but soon expanded to stains for endogenous structures like microtubules, F-actin, and DNA,[27-28] as well as sensors for disparate analytes.[13, 29-30] The cell-permeability, brightness, photostability, and far-red wavelengths of SiR ligands have enabled advanced imaging experiments using structured illumination microscopy (SIM) and stimulated emission depletion (STED) imaging.[14]

The low $K_{L-Z}$ of SiR also spurred the development of hydroxymethyl (HM) derivatives of SiR that spontaneously blink under physiological conditions and are useful for single-molecule localization microscopy (SMLM).[31] In another extension, it was discovered that replacing the N,N-dimethylamino groups in fluorophores with four-membered azetidine rings was a general strategy to improve brightness.[15] Applying this strategy to SiR yielded a brighter and more fluorogenic dye: 'Janelia Fluor' 646 ($JF_{646}$, 2; $\lambda_{abs}/\lambda_{em}$=646 nm/664 nm, $\varepsilon$=5,000 $M^{-1}$ $cm^{-1}$, $\Phi$=0.54, $K_{L-Z}$=0.0012).[15]

This Si-rhodamine could be fine-tuned by incorporating 3-fluoroazetidine into the structure, yielding $JF_{635}$ (3, $\lambda_{abs}$/$\lambda_{cm}$=635 nm/652 nm, $\varepsilon$=400 $M^{-1}$ $cm^{-1}$, $\Phi$=0.54), which exhibited a low $K_{L-Z}$ value (<0.0001) and high fluorogenicity.[32-33] This universal approach could be applied to carborhodamine and standard oxygen-containing rhodamine scaffolds to yield bright fluorescent and fluorogenic dyes across the visible spectrum (4-7, FIG. 1C).

While there have been a number of advances in the field of fluorescence microscopy for imaging living cells, due to the importance and utility of small-molecule fluorophores as fundamental tools for biological research, there remains a need in the art for additional fluorogenic molecules, including fluorogenic molecules emitting distinct colors, and molecules that are sufficiently highly fluorogenic, which can be used in advanced fluorescent microscopy studies.

SUMMARY

The presently-disclosed subject matter meets some or all of the above-identified needs, as will become evident to those of ordinary skill in the art after a study of information provided in this document.

This Summary describes several embodiments of the presently-disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently-disclosed subject matter, whether listed in this Summary or not. To avoid excessive repetition, this Summary does not list or suggest all possible combinations of such features.

In view of the importance and utility of small-molecule fluorophores as fundamental tools for biological research, disclosed herein are a number of unique fluorogenic molecules emitting distinct colors. Molecules disclosed herein expand the palette of fluorogenic molecules to include, for example, green- or orange-emitting versions of SiR. As also disclosed herein, the relationship between $K_{L-Z}$ of various and the fluorogenicity of their respective HaloTag ligands were investigated to create a quantitative framework for the rational design of new fluorogenic rhodamine dyes.

As taught herein, the $K_{L-Z}$ is sufficient to predict fluorogenicity and determined that $K_{L-Z}<10^{-2}$ was an appropriate threshold for the design of highly fluorogenic ligands, which was validated with known molecules, and applied to unique molecules disclosed herein.

In some embodiments of the presently-disclosed subject matter, a compound of the following formula is provided:

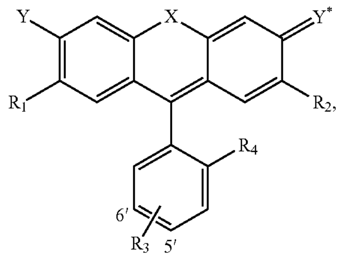

wherein Y is —$NH_2$ or

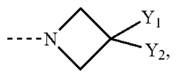

wherein $Y_1$ and $Y_2$ are each independently selected from the group consisting of H, F, CN, $OCH_3$, $SO_2Me$, $CF_3$, $CH_3$, and $CO_2H$; X is selected from the group consisting of O,N-alkyl, S, $Si(alkyl)_2$, and $C(alkyl)_2$; $R_1$ and $R_2$ are each independently selected from the group consisting of H, alkyl, and halogen; $R_3$, which can be a substitution at either the 5' position or the 6' position of the ring to which it is bound, is selected from the group consisting of H, self-labeling protein tag ligand, $CO_2H$, $CO_2CH_3$, $CO_2t$-Bu, N-hydroxysuccinimidyl (NHS) ester, and a targeting moiety; and $R_4$ is $CH_2OH$ or $CO_2H$, so long as when $R_4$ is $CO_2H$, then $Y_1$-$Y_4$ are selected from the group consisting of H and F $R_1$, and $R_2$ are F, and X is O.

As will be appreciated by the skilled artisan, the compounds disclosed herein will In some embodiments of the presently-disclosed subject matter, a compound of the following formula is provided:

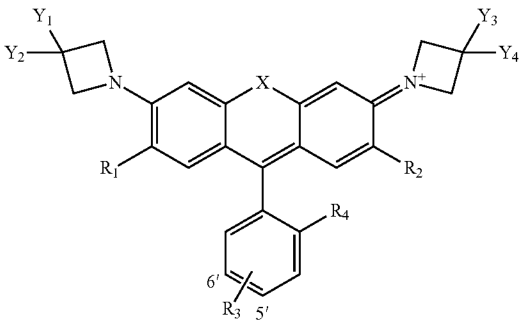

or

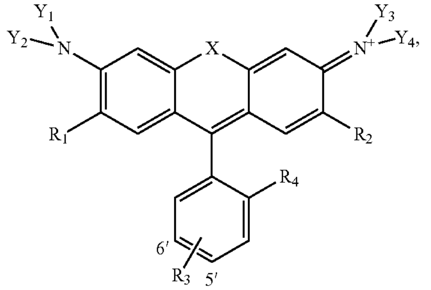

wherein $Y_1$-$Y_4$ are each independently selected from the group consisting of H, F, CN, $OCH_3$, $SO_2Me$, $CF_3$, $CH_3$, and $CO_2H$; X is selected from the group consisting of O,N-alkyl, S, $Si(alkyl)_2$, and $C(alkyl)_2$; $R_1$ and $R_2$ are each independently selected from the group consisting of H, alkyl, and halogen; $R_3$, which can be a substitution at either the 5' position or the 6' position of the ring to which it is bound, is selected from the group consisting of H, self-labeling protein tag ligand, $CO_2H$, $CO_2CH_3$, $CO_2t$-Bu, N-hydroxysuccinimidyl (NHS) ester, and a targeting moiety; and $R_4$ is $CH_2OH$ or $CO_2H$, so long as when $R_4$ is $CO_2H$, then $Y_1$-$Y_4$ are selected from the group consisting of H and F $R_1$, and $R_2$ are F, and X is O.

In some embodiments of the presently-disclosed subject matter, a compound of the following formula is provided:

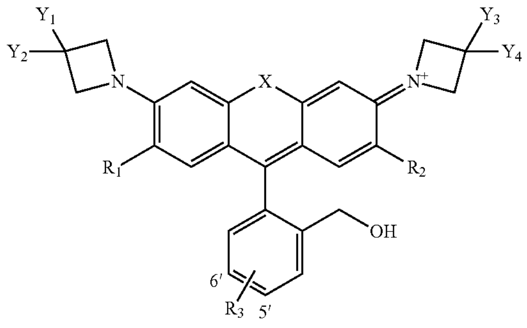

wherein $Y_1$-$Y_4$ are each independently selected from the group consisting of H, F, CN, $OCH_3$, $SO_2Me$, $CF_3$, $CH_3$, and $CO_2H$; X is selected from the group consisting of O,N-alkyl, S, $Si(alkyl)_2$, and $C(alkyl)_2$; $R_1$ and $R_2$ are each independently selected from the group consisting of H, alkyl, and halogen; and $R_3$, which can be a substitution at either the 5' position or the 6' position, is selected from the group consisting of H, self-labeling protein tag ligand, $CO_2H$, $CO_2CH_3$, $CO_2t$-Bu, N-hydroxysuccinimidyl (NHS) ester, and a targeting moiety.

In some embodiments of the presently-disclosed subject matter, a compound of the following formula is provided:

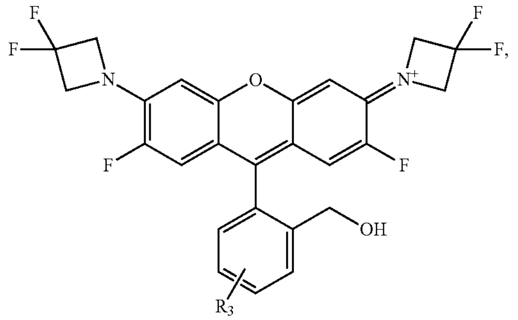

wherein $R_3$, which can be a substitution at either the 5' position or the 6' position, is selected from the group consisting of H, self-labeling protein tag ligand, $CO_2H$, $CO_2CH_3$, $CO_2t$-Bu, N-hydroxysuccinimidyl (NHS) ester, and a targeting moiety.

In some embodiments of the presently-disclosed subject matter, a compound of the following formula is provided:

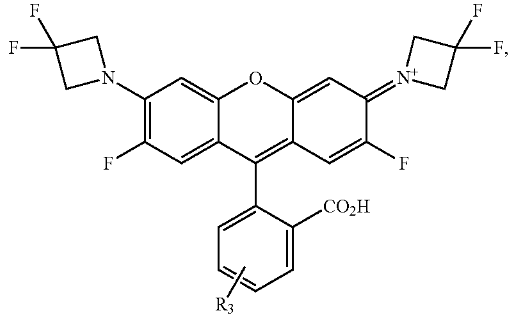

wherein $R_3$, which can be a substitution at either the 5' position or the 6' position, is selected from the group consisting of H, self-labeling protein tag ligand, $CO_2H$, $CO_2CH_3$, $CO_2t$-Bu, N-hydroxysuccinimidyl (NHS) ester, and a targeting moiety.

In some embodiments of the presently-disclosed subject matter, a compound of the following formula is provided:

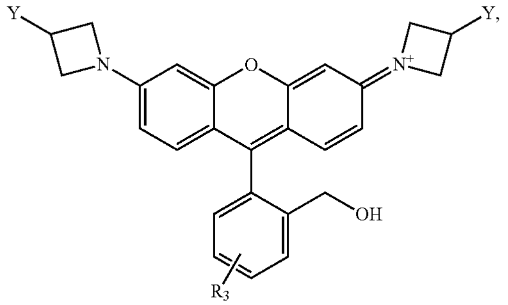

wherein $R_3$, which can be a substitution at either the 5' position or the 6' position, is selected from the group consisting of H, self-labeling protein tag ligand, $CO_2H$, $CO_2CH_3$, $CO_2t$-Bu, N-hydroxysuccinimidyl (NHS) ester, and a targeting moiety; and Y is H or F.

In some embodiments of the presently-disclosed subject matter, a compound of the following formula is provided:

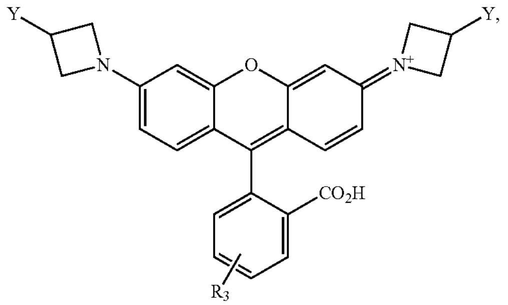

wherein $R_3$, which can be a substitution at either the 5' position or the 6' position, is selected from the group consisting of H, self-labeling protein tag ligand, $CO_2H$, $CO_2CH_3$, $CO_2t$-Bu, N-hydroxysuccinimidyl (NHS) ester, and a targeting moiety; and Y is H or F.

In some embodiments of the presently-disclosed subject matter, a compound of the following formula is provided:

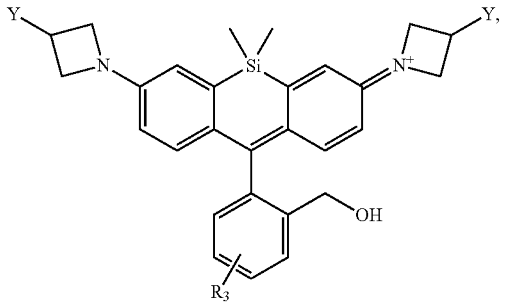

wherein $R_3$, which can be a substitution at either the 5' position or the 6' position, is selected from the group consisting of H, self-labeling protein tag ligand, $CO_2H$, $CO_2CH_3$, $CO_2t$-Bu, N-hydroxysuccinimidyl (NHS) ester, and a targeting moiety; and Y is H or F.

In some embodiments of the presently-disclosed subject matter, a compound of the following formula is provided:

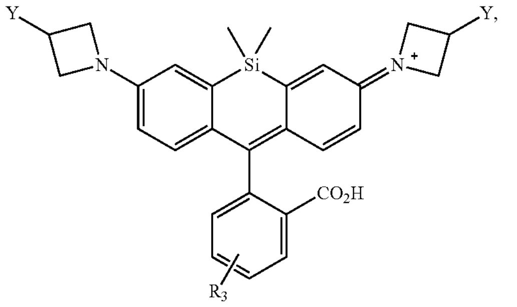

wherein $R_3$, which can be a substitution at either the 5' position or the 6' position, is selected from the group consisting of H, self-labeling protein tag ligand, $CO_2H$, $CO_2CH_3$, $CO_2$t-Bu, N-hydroxysuccinimidyl (NHS) ester, and a targeting moiety; and Y is H or F.

In some embodiments of the presently-disclosed subject matter, a compound of the following formula is provided:

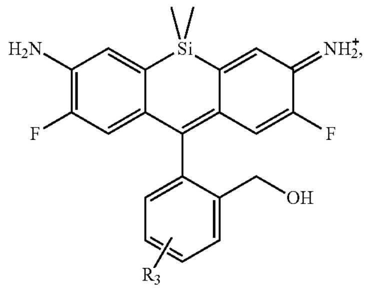

wherein $R_3$, which can be a substitution at either the 5' position or the 6' position, is selected from the group consisting of H, self-labeling protein tag ligand, $CO_2H$, $CO_2CH_3$, $CO_2$t-Bu, N-hydroxysuccinimidyl (NHS) ester, and a targeting moiety.

In some embodiments of the presently-disclosed subject matter, a compound of the following formula is provided:

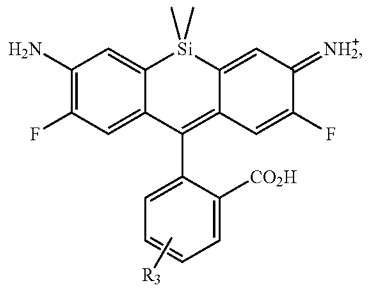

wherein $R_3$, which can be a substitution at either the 5' position or the 6' position, is selected from the group consisting of H, self-labeling protein tag ligand, $CO_2H$, $CO_2CH_3$, $CO_2$t-Bu, N-hydroxysuccinimidyl (NHS) ester, and a targeting moiety.

In some embodiments of the presently-disclosed subject matter, $R_3$ is a targeting moiety that is a self-labeling protein tag. In some embodiments of the presently-disclosed subject matter, $R_3$ is a targeting moiety for directing the compound to DNA, microtubules, or lysosomes. In some embodiments of the presently-disclosed subject matter, $R_3$ is a targeting moiety selected from the group consisting of trimethoprim, Taxol, Hoechst, and pepstatin A.

The presently-disclosed subject matter is further inclusive of methods for using the present compounds and their intermediates, as well as methods for preparing such compounds and the their intermediates.

In some embodiments of the presently-disclosed subject matter, a detection method is provided. An exemplary method provides for the detection of a target substance, and involves contacting a sample with a compound as disclosed herein, and detecting an emission light from the compound. The emission light can indicate the presence of the target substance and the intesity of the emission light can indicate the relative amount of the target substance.

In some embodiments of the detection method, the target substance is selected from a protein, a carbohydrate, a polysaccharide, a glycoprotein, a hormone, a receptor, an antigen, an antibody, a virus, a substrate, a metabolite, an inhibitor, a drug, a nutrient, a growth factor, a lipoprotein, and a combination thereof.

In some embodiments of the detection method, the detecting step is performed with a microscope. In some embodiments, the contacting step and the detecting step are performed in a live cell.

In some embodiments, the detection method also involves a step of exposing the compound to an absorption light that includes a wavelength of about 100 nm to about 1000 nm.

In some embodiments of the method, the compound includes a first compound and a second compound, where the first compound is selective for a first target substance and is capable of emitting a first emission light, and the second compound is selective for a second target substance and is capable of emitting a second emission light. The detecting step includes detecting the first emission light that indicates the presence of the first target substance and the second emission light that indicates the presence of the second target substance.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are used, and the accompanying drawings of which:

FIG. 1A—Lactone-zwitterion equilibrium of SiR (1). FIG. 1B—Proposed mechanism of fluorogenicity and cell-permeability of SiR (1). FIG. 1C-Structure of $JF_{646}$ (2) and other Janelia Fluor dyes 3-7. FIG. 1D—Absorption at $\lambda_{abs}$ vs. SDS concentration for 1 and 2; gray shading indicates [SDS] above the critical micellular concentration (c.m.c.). FIG. 1E—The change in fluorescence over basal fluorescence of HaloTag ligands upon labeling purified HaloTag protein ($\Delta F/F_0$) vs. the $K_{L-Z}$ of the corresponding free dyes 1-10; the solid line indicates a linear fit ($R^2$=0.93) and the dashed lines indicate the $K_{L-Z}$ threshold for a 10-fold fluorogenic effect.

FIG. 2A—Synthesis of $SiR_{110}$ (8). FIG. 2B—Synthesis of $SiR_{110}$-HaloTag ligand ($8_{HTL}$). FIG. 2C—Absorption spectra of $8_{HTL}$ (5 μM) in the absence (black line) or presence (grey line) of excess HaloTag protein. FIG. 2D—Widefield fluorescence image of U2OS cells expressing histone H2B-HaloTag fusion protein and labeled with $8_{HTL}$; scale bar: 20

Figure 2A:
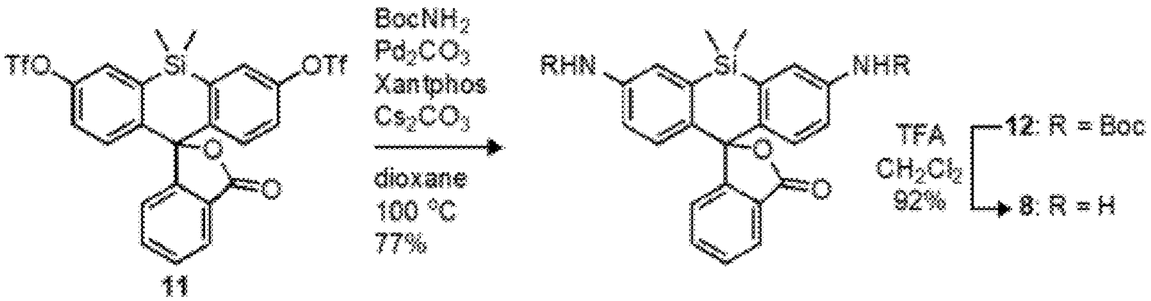
FIGS. 2A-2E. Synthesis and testing of $SiR_{110}$.
Figure 2B:
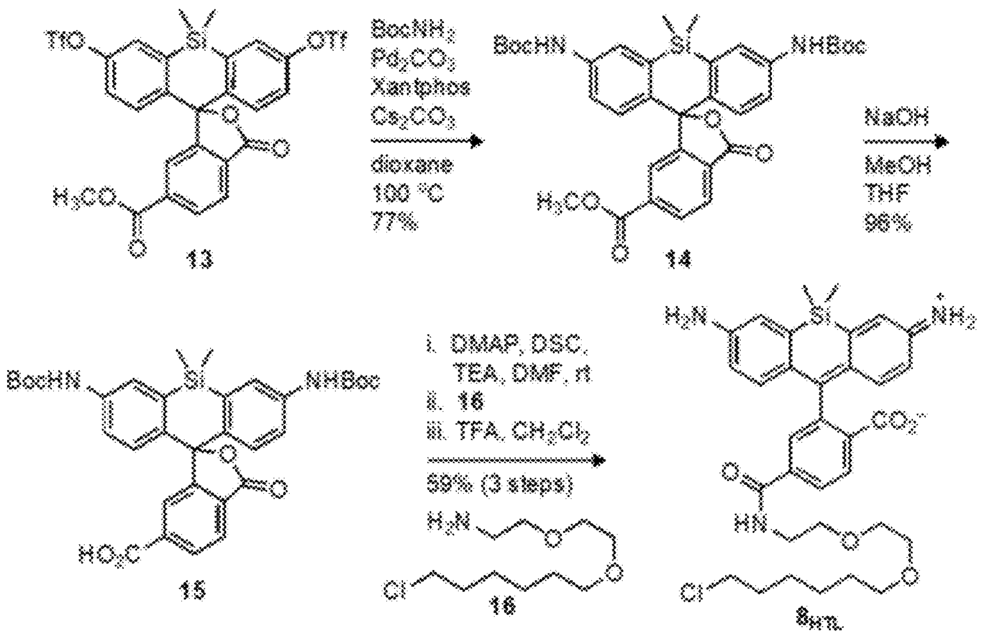
Figure 2C:
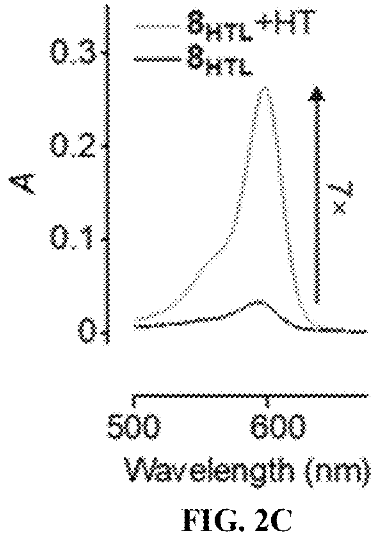
Figure 2D:
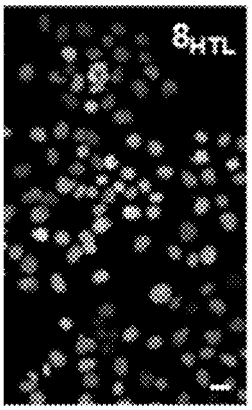
Figure 2E:
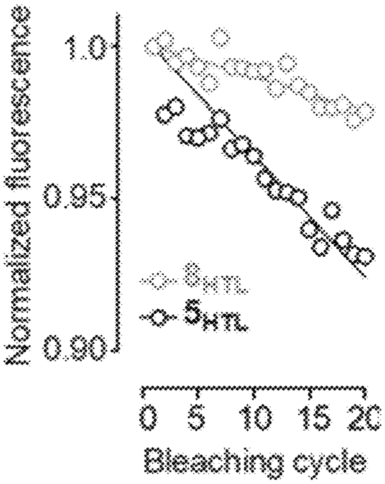

μm FIG. 2E—Relative photostability of $8_{HTL}$ and $JF_{585}$-HaloTag ligand ($5_{HTL}$) in live cells.

Figure 3A:
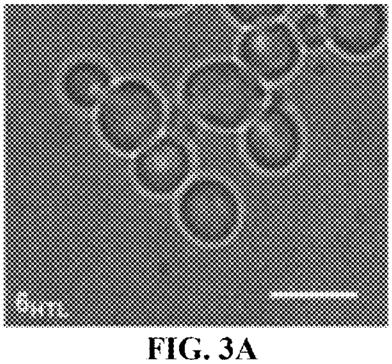
Figure 3B:
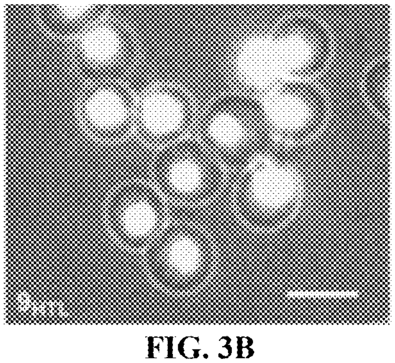
Figure 3C:
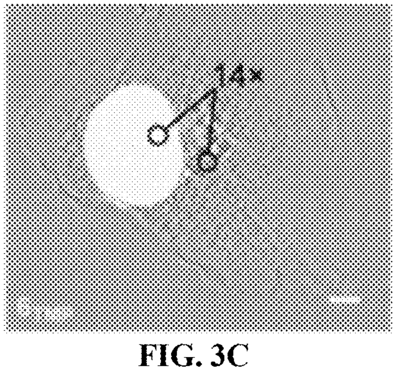
Figure 3D:
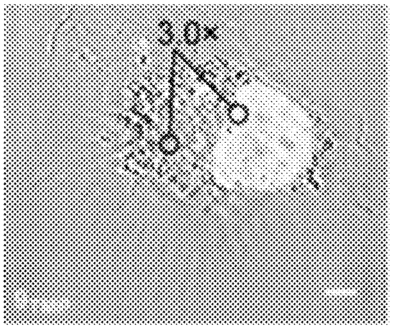

FIGS. 3A-3D. $JF_{552}$ ligands show improved cell permeability. FIGS. 3A and 3B—Overlay of fluorescence and bright-field images of yeast cells expressing a histone-H2A.Z-HaloTag fusion protein and labeled with $6_{HTL}$ (FIG. 3A) or $9_{HTL}$. (FIG. 3B); scale bars: 5 μm. FIGS. 3C and 3D—Overlay of fluorescence and bright-field images of U2OS cells expressing histone-H2B-eDHFR fusion protein and labeled with $6_{TMP}$ (FIG. 3C) or $9_{TMP}$ (FIG. 3D); scale bars: 5 μm.

Figure 4A:
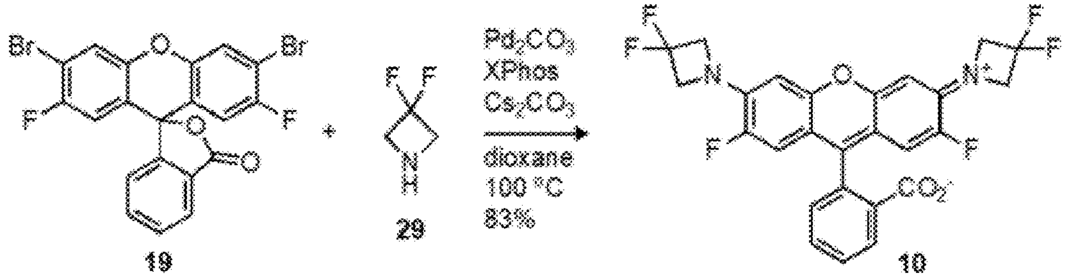
Figure 4B:
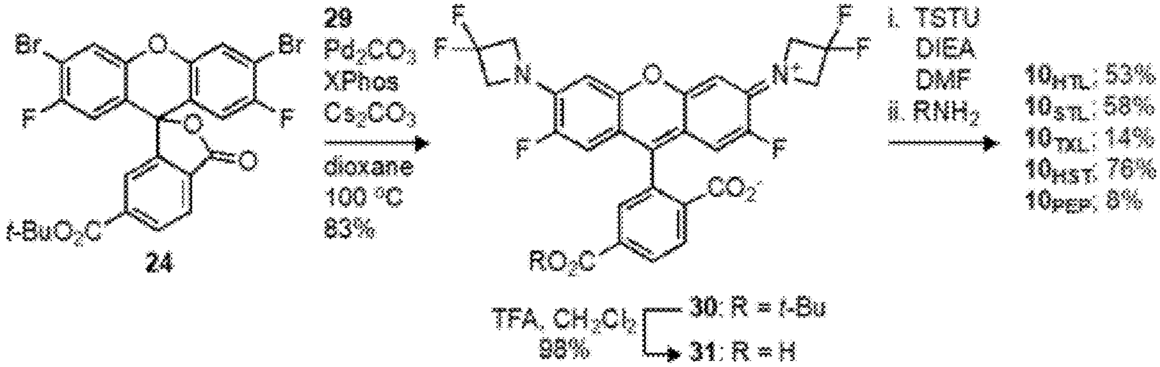
Figure 4C:
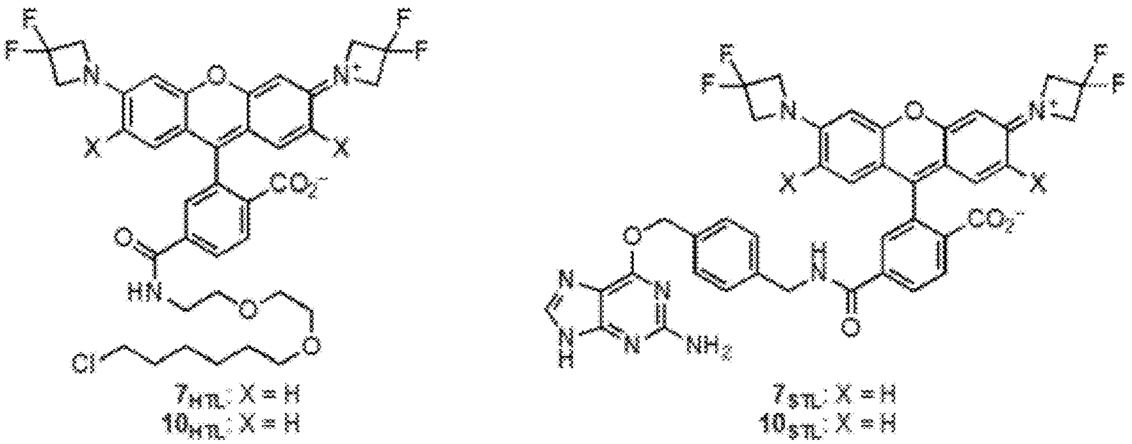
Figure 4D:
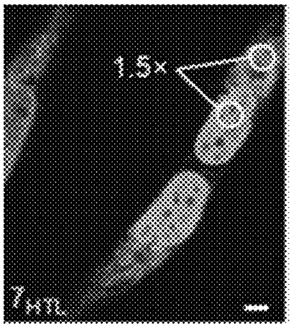
Figure 4E:
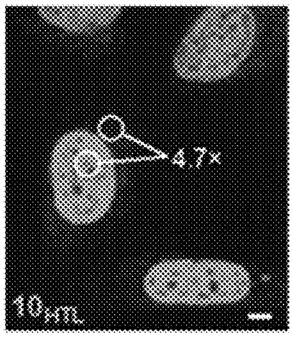
Figure 4F:
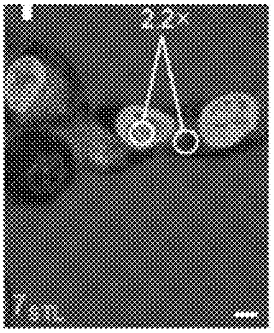
Figure 4G:
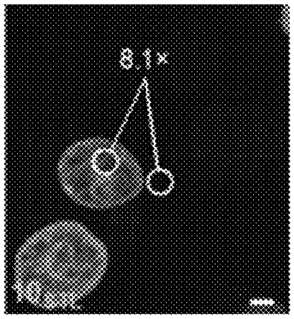

FIGS. 4A-4G. Synthesis and no-wash imaging of $JF_{526}$ ligands. FIGS. 4A and 4B—Synthesis of $JF_{526}$ (FIG. 4A) and $JF_{526}$ ligands (FIG. 4B). FIG. 4C—Structures of $JF_{525}$ and $JF_{526}$-HaloTag and SNAP-tag ligands. FIGS. 4D and 4E-Confocal images of COS7 cells expressing a histone-H2B-HaloTag fusion protein and labeled with 500 nM of $JF_{525}$-HaloTag ligand ($7_{HTL}$, d) or $JF_{526}$-HaloTag ligand ($10_{HTL}$, e). FIGS. 4F and 4G—Confocal images of COS7 cells expressing histone-H2B-SNAP-tag fusion protein and labeled with 1 μM of $JF_{525}$-SNAP-tag ligand ($7_{STL}$, FIG. 4F) or $JF_{526}$-SNAP-tag ligand ($10_{STL}$, FIG. 4G); scale bars for all images: 5 μm.

Figure 5A:
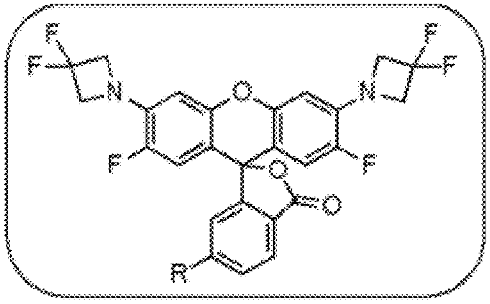
Figure 5A:
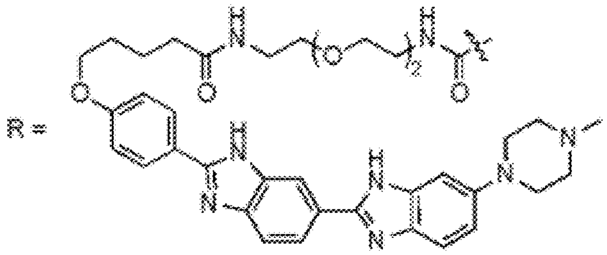
Figure 5A:
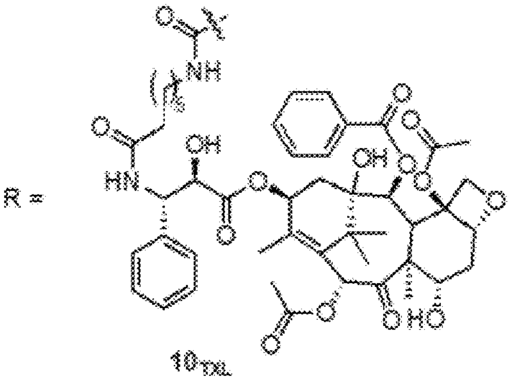
Figure 5A:
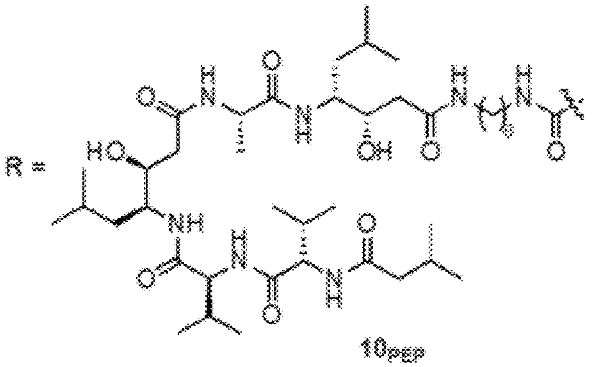
Figure 5B:
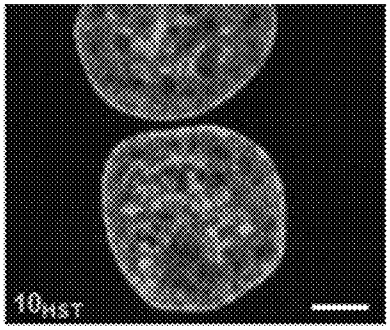
Figure 5C:
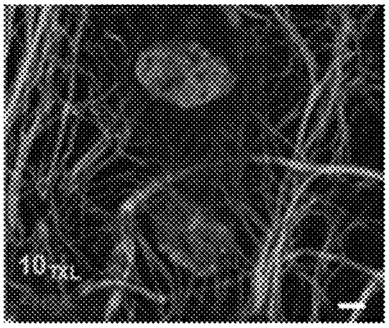
Figure 5D:
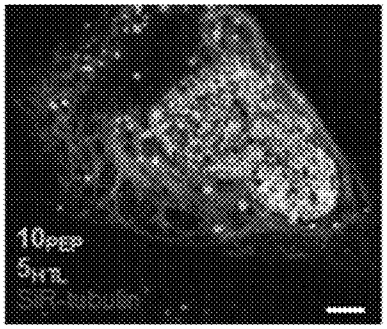

FIGS. 5A-5D. Extending the repertoire of $JF_{526}$ ligands. FIG. 5A—Structures of $JF_{526}$ ligands. FIG. 5B—Confocal image of live U2OS cells stained with $JF_{526}$-Hoechst ($10_{HST}$). FIG. 5C—Confocal image of mouse primary hippocampal neurons stained with $JF_{526}$-Taxol ($10_{TXL}$) and $JF_{646}$-Hoechst ($2_{HST}$). FIG. 5D—Confocal image of U2OS cells expressing histone-H2B-HaloTag fusion protein and labeled with $JF_{526}$-pepstatin A ($10_{PEP}$), $JF_{585}$-HaloTag ligand ($5_{HTL}$), and 'SiR-tubulin' ($1_{TXL}$). All images were acquired without washing; scale bars: 5 μm.

Figure 6A:
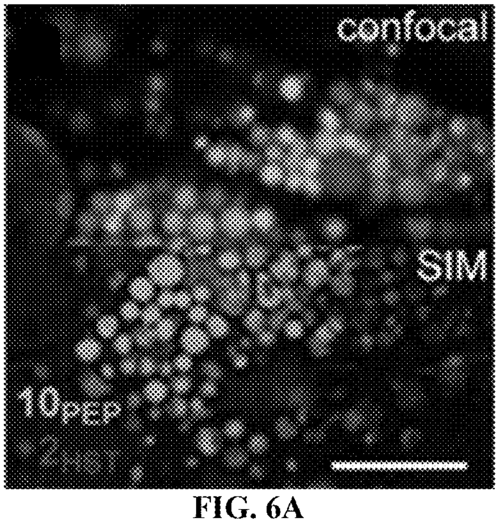
Figure 6B:
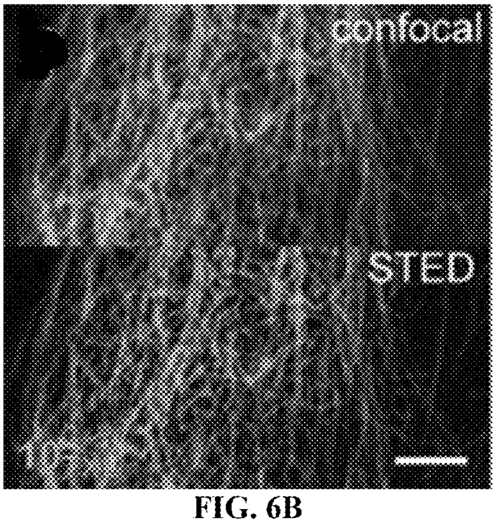
Figure 6C:
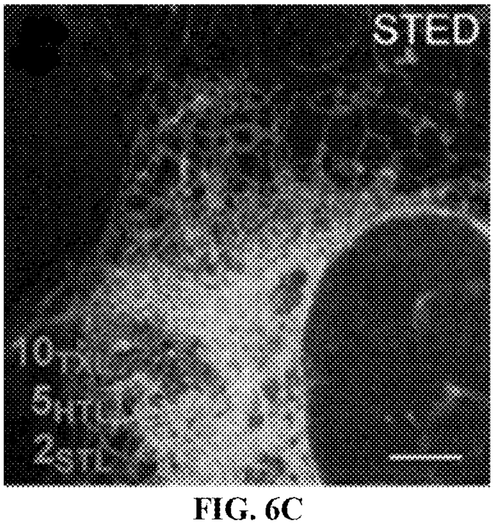
Figure 6D:
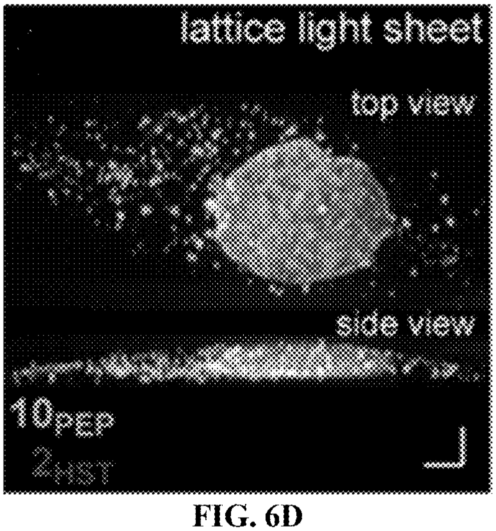

FIGS. 6A-6D. Advanced microscopy imaging using $JF_{526}$. FIG. 6A—Confocal and SIM images of mouse primary hippocampal neurons stained with $10_{PEP}$ and $JF_{646}$-Hoechst ($2_{HST}$). FIG. 6B—Confocal and STED microscopy images of U2OS cells stained with $10_{TXL}$. FIG. 6C—Three-color live-cell STED image of U2OS cells expressing Sec61β-SNAP-tag labeled with $JF_{646}$-SNAP-tag ligand ($2_{STL}$), TOMM20-HaloTag labeled with $JF_{585}$-HaloTag ligand ($5_{HTL}$) and microtubules stained with $10_{TXL}$. FIG. 6D—Lattice light sheet microscopy image of U2OS cells stained with $10_{PEP}$ and $2_{HST}$. Scale bars for all images: 5 μm.

Figure 7A:
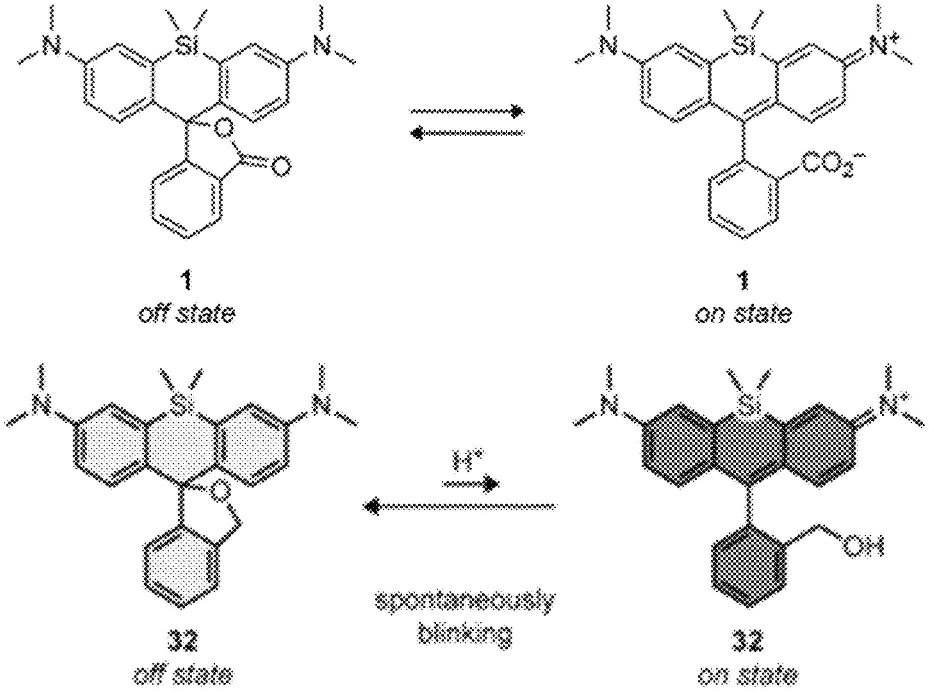
Figure 7B:
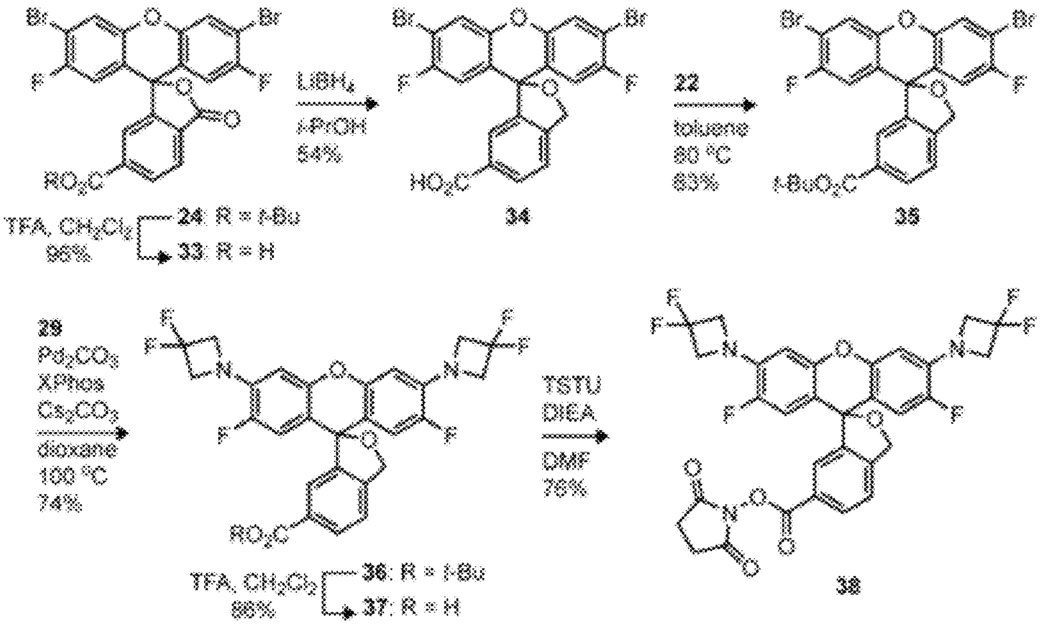
Figure 7C:
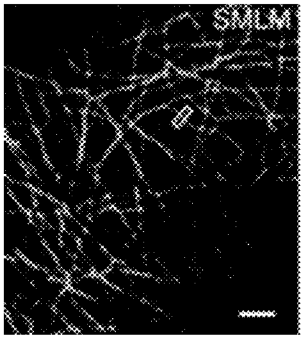
Figure 7D:
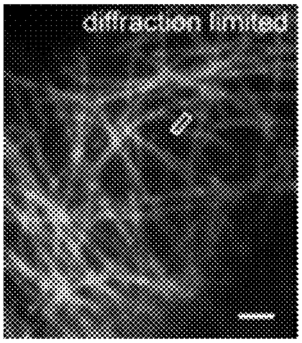
Figure 7E:
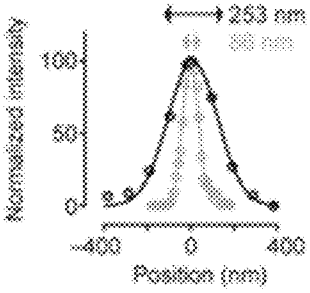
Figure 7F:
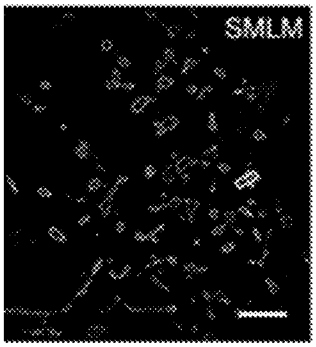
Figure 7G:
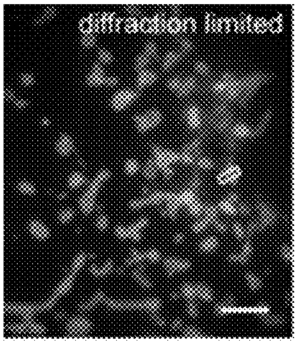

FIGS. 7A-7H. Localization microscopy with HM-$JF_{526}$. FIG. 7A—Top panel: The rhodamines exist as the equilibrium between the nonfluorescent, closed form and the fluorescent, open form; Replacing the o-carboxy moiety in tetramethyl-Si-rhodamine (SiR, 1) with a more nucleophilic hydroxymethyl group elicits a substantial shift of the equilibrium to the nonfluorescent, closed form. Bottom panel: The resulting hydroxymethyl SiR (HM-SiR, 32) dye mainly adopts the nonfluorescent form at physiological conditions, while spontaneously opens to the fluorescent form and enables facile Single-Molecule Localization Microscopy (SMLM) at physiological conditions. FIG. 7B—Synthesis of HM-$JF_{526}$ NHS 38. FIGS. 7C and 7D—Immunofluorescence images of tubulin labeled with HM-$JF_{526}$: (FIG. 7C) SMLM (FIG. 7D) diffraction limited. FIG. 7E—Transverse profiles of fluorescence intensity corresponding to boxed regions in FIG. 7C and FIG. 7D. FIGS. 7F and 7G—Immunofluorescence images of TOMM20 labeled with HM-$JF_{526}$: (FIG. 7F) SMLM (FIG. 7G) diffraction limited. (FIG. 7H—Transverse profiles of fluorescence intensity corresponding to boxed regions in FIGS. 7F and 7G. Scale bars for all images: 5 μm. Solid lines in FIGS. 7E and 7H indicate Gaussian fits; numbers indicate the full width at half maximum (FWHM) determined by the Gaussian fits of the SMLM (grey) and diffraction limited imaging (black).

Figure 8:
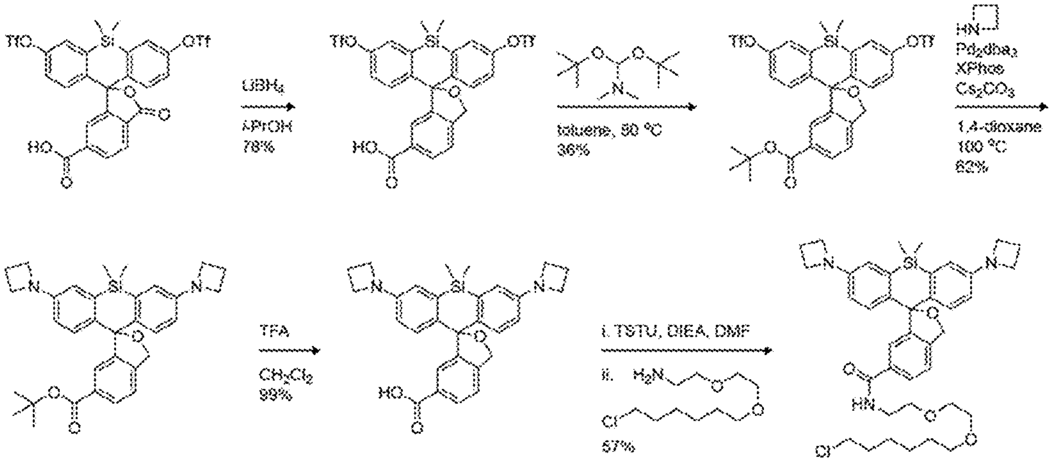

FIG. 8. The synthesis of HM-$JF_{646}$-HaloTag Ligand (HM-$JF_{646}$-HTL).

Figure 9A:
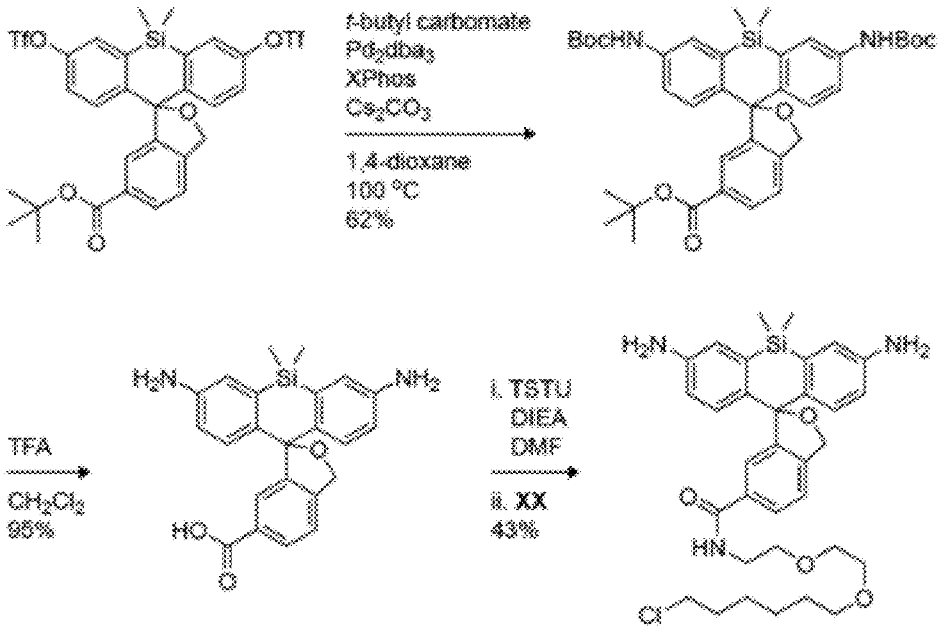
Figure 9B:
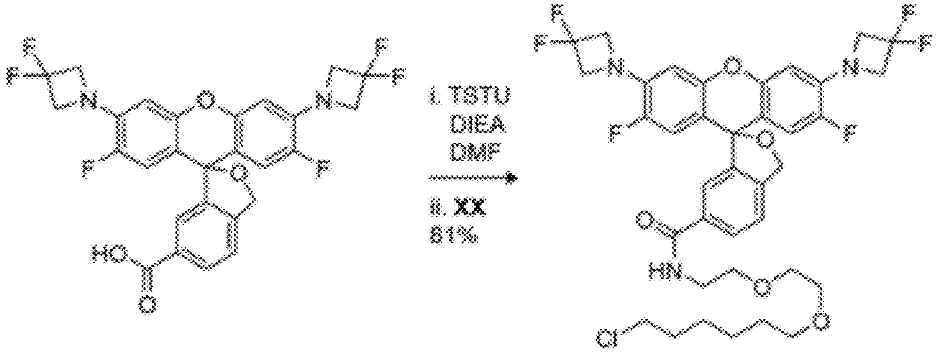

FIGS. 9A and 9B. The synthesis of HM-$SiR_{110}$-HTL (FIG. 9A) and HM-$JF_{526}$-HTL (FIG. 9B).

FIGS. 10A-10F. HaloTag ligands of the HM dyes were labeled with cells expressing mitochondrial protein TOMM20 fused to the HaloTag protein. Cells were imaged using conventional microscopy, SMLM, or super-resolution optical fluctuation imaging (SOFI). (FIGS. 10A and 10B) HM-$JF_{526}$-HTL. (FIGS. 10C and 10D) HM-$SiR_{110}$-HTL. (FIGS. 10E and 10F) HM-$JF_{646}$-HTL.

Figure 11A:
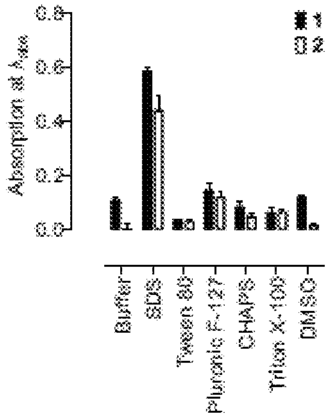
Figure 11B:
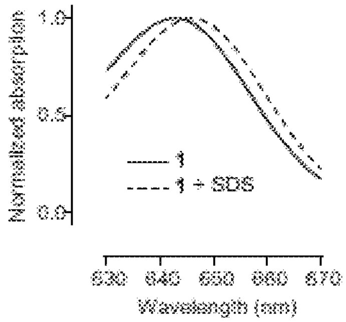
Figure 11C:
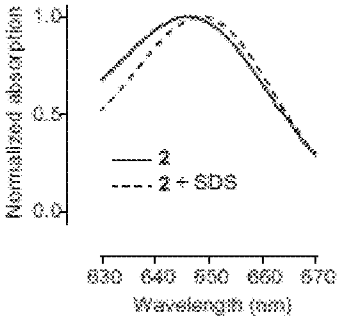
Figure 11D:
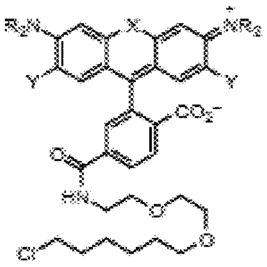
Figure 11D:
Figure 11D:
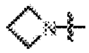
Figure 11D:
Figure 11D:
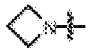
Figure 11D:
Figure 11D:
Figure 11D:
Figure 11D:
Figure 11D:
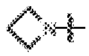
Figure 11D:
Figure 11E:
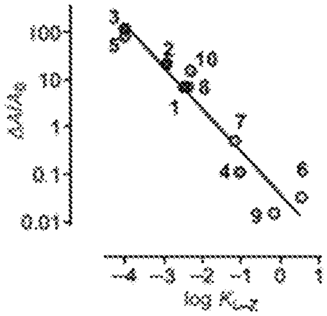
Figure 11F:
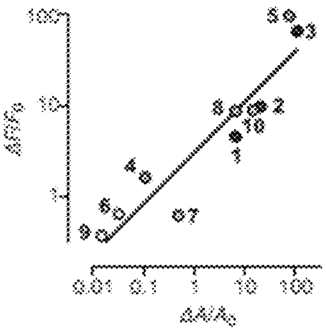
Figure 11G:
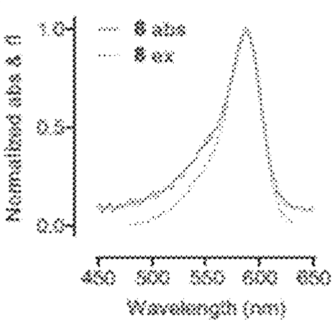
Figure 11H:
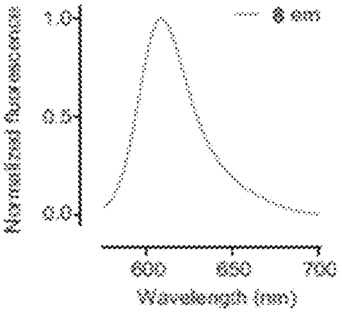
Figure 11I:
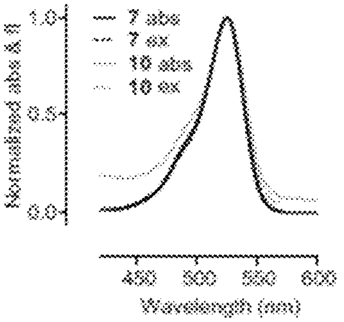
Figure 11J:
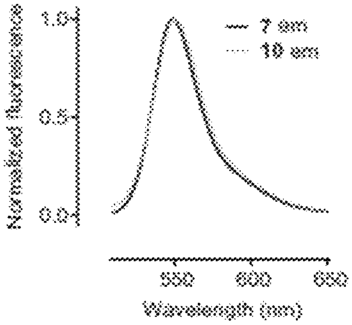

FIGS. 11A-11J. FIG. 11A-Absorption at $\lambda_{abs}$ for dyes 1 and 2 in 20 mM sodium phosphate buffer, pH 7.0 containing 5 mg/mL detergent, error bars show±s.e.m. FIGS. 11B and 11C-Absorption spectra for dyes 1 (FIG. 11B) and 2 (FIG. 11C) near $\lambda_{abs}$ in the presence (dashed line) or absence (solid line) of SDS. FIG. 11D—Chemical structures and properties of HaloTag ligands 1HTL-10HTL; ΔA/A0 indicates the change in absorption (ΔA) and ΔF/F0 indicates the change in fluorescence (ΔF) of the HaloTag ligands upon binding purified HaloTag protein divided by the basal absorption or fluorescence of the free ligand (F0 or A0). FIG. 11E—ΔA/A0 of the HaloTag ligands 1HTL-10HTL vs. KL-Z of the corresponding free dyes 1-10; the solid line indicates a linear fit ($R^2$=0.93). (f) ΔF/F0 vs. ΔA/A0 for the HaloTag ligands 1HTL-10HTL; the solid line indicates a linear fit ($R^2$=0.87). FIG. 11G—Normalized absorption (abs, solid line), normalized fluorescence excitation (ex, dashed line), and FIG. 11H—normalized fluorescence emission (em) spectra for dye 8 in 10 mM HEPES, pH 7.3. FIG. 11I—Normalized abs (solid line), normalized ex (dashed line), and FIG. 11J—normalized em spectra for dyes 7 and 10 in 10 mM HEPES, pH 7.3; note: the normalized absorption spectra of dyes 8 and 10 exhibit higher noise due to relatively low visible absorption in aqueous buffer.

Figure 12A:
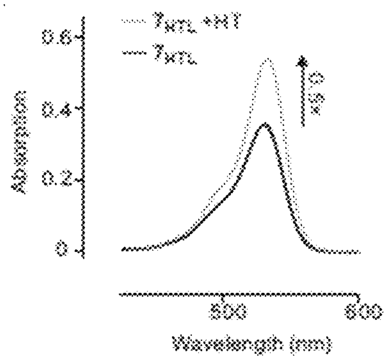
Figure 12B:
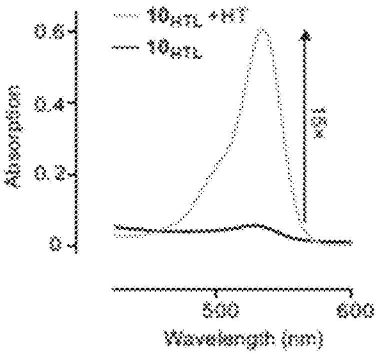
Figure 12C:
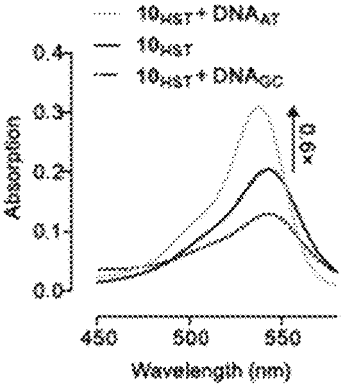
Figure 12D:
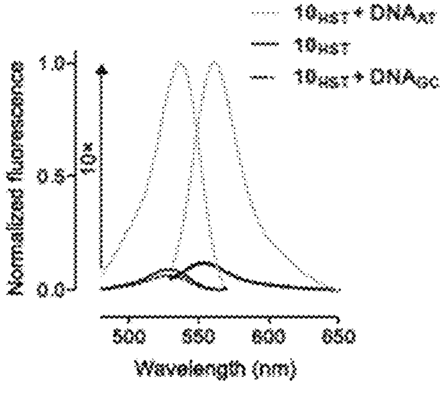
Figure 12E:
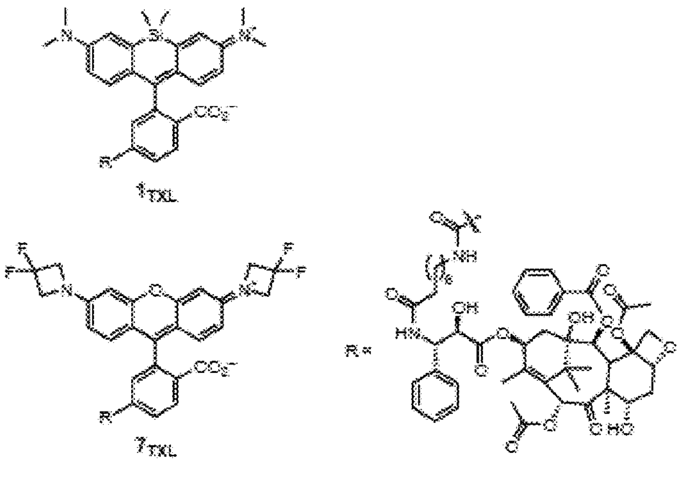
Figure 12F:
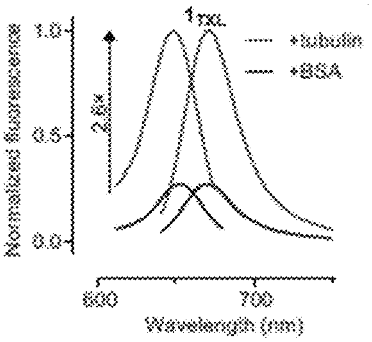
Figure 12G:
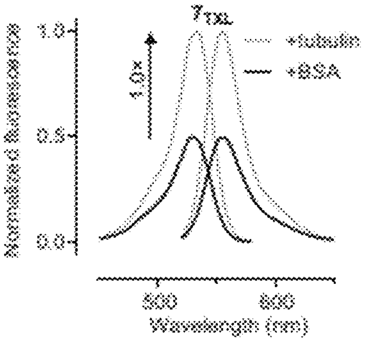
Figure 12H:
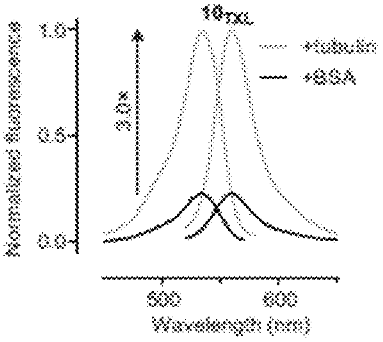
Figure 12I:
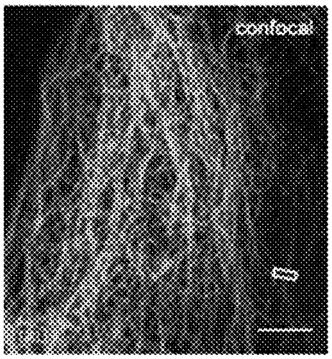
Figure 12J:
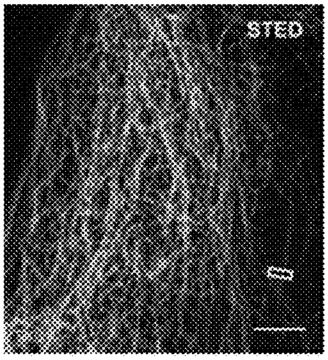
Figure 12K:
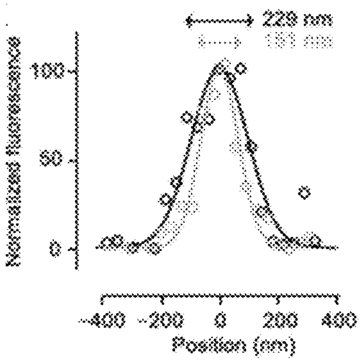

FIGS. 12A-12K. FIGS. 12A and 12B—Absorption spectra of HaloTag ligands 7HTL (FIG. 12A) and 10HTL (FIG. 12B) in the presence or absence of excess HaloTag protein (HT). FIG. 12C—Absorption spectra of JF526-Hoechst conjugate (10HST, 5 μM) in PBS, pH 7.4 alone, with polyA·polyT DNA (DNAAT, 50 μM), or polyG·polyC DNA (DNAGC, 50 PM). FIG. 12D—Fluorescence excitation and emission spectra of JF526-Hoechst conjugate (10HST, 500 nM) in PBS, pH 7.4 alone, with polyA·polyT DNA (DNAAT, 5 μM), or polyG·polyC DNA (DNAGC, 5 μM). FIG. 12E—Chemical structures of 'SiR-tubulin' ($1_{TXL}$) and JF525-Taxol (7TXL). FIG. 12F-12H—Normalized fluorescence excitation and emission spectra of 1TXL (FIG. 12F), 7TXL (FIG. 12G), or 10TXL (FIG. 12H) in the presence of polymerized tubulin (grey) or bovine serum albumin (BSA; black). FIGS. 12I and 12J—Confocal image (FIG. 12I) and STED image (FIG. 12J) of live U2OS cells incubated with 10TXL (1 μM) and Verapamil (10 μM) for 1 h; scale bars: 5 μm. FIG. 12K—Transverse profiles of fluorescence intensity corresponding to regions boxed in confocal (black) and STED (grey). Solid lines indicate Gaussian fit; double-headed arrows and numbers indicate full width at half maximum (FWHM) determined by the Gaussian fit.

DESCRIPTION OF EXEMPLARY EMBODIMENTS

The details of one or more embodiments of the presently-disclosed subject matter are set forth in this document. Modifications to embodiments described in this document, and other embodiments, will be evident to those of ordinary skill in the art after a study of the information provided in this document. The information provided in this document, and particularly the specific details of the described exemplary embodiments, is provided primarily for clearness of understanding and no unnecessary limitations are to be understood therefrom. In case of conflict, the specification of this document, including definitions, will control.

Rhodamine dyes exist in equilibrium between a fluorescent zwitterion and nonfluorescent lactone. Tuning this equilibrium toward the nonfluorescent lactone form can improve cell-permeability and create ‘fluorogenic’ molecules-dyes that shift to the fluorescent zwitterion upon binding a biomolecular target.

Based on a prototypical fluorogenic dye SiR (1) and Janelia Fluor dyes (2-7), it was shown, as described herein, that the equilibrium constant, $K_{L-Z}$, is sufficient to predict fluorogenicity of ligands. An inverse relationship between these two parameters was found and a quantitative framework for developing new fluorogenic molecules was developed: decreasing $K_{L-Z}$ below $10^{-2}$ gives fluorogenicity of at least 10-fold.

This rubric allowed the identification of exemplary compounds, as disclosed herein. Exemplary embodiments of the compounds have shorter fluorescent excitation and emission wavelengths, and/or improved photostability, as compared to prior compounds. The compounds disclosed in these studies provide versatile scaffolds for fluorogenic probes including labels for self-labeling tags, stains for endogenous structures, and spontaneously blinking labels for single-molecule localization microscopy.

The presently-disclosed subject matter includes compounds that have utility as fluorophores (e.g., fluorescent dyes). The present compounds can be utilized as fluorescent probes to observe and characterize the location and/or concentration of particular substances. In this regard, terms such as ‘probe,’ ‘dye,’ and the like are used herein to refer to compounds comprising a fluorophore moiety that is selective for and/or is bonded to a binding element that is selective for a target substance. The probes can emit an emission light, which can be used to determine the presence of and/or measure the quantity of the target substance. In this respect, the presently-disclosed subject matter also includes methods for using the present compounds and their intermediates, as well as methods for preparing such compounds and the their intermediates.

In some embodiments of the presently-disclosed subject matter, a compound of the following formula is provided:

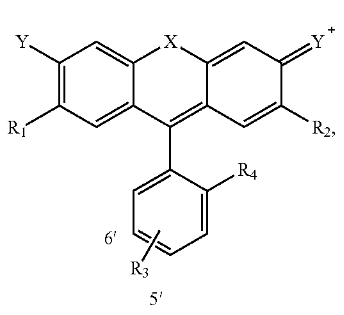

wherein Y is —$NH_2$ or

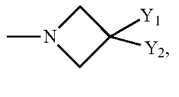

wherein $Y_1$ and $Y_2$ are each independently selected from the group consisting of H, F, CN, $OCH_3$, $SO_2Me$, $CF_3$, $CH_3$, and $CO_2H$; X is selected from the group consisting of O,N-alkyl, S, $Si(alkyl)_2$, and $C(alkyl)_2$; $R_1$ and $R_2$ are each independently selected from the group consisting of H, alkyl, and halogen; $R_3$, which can be a substitution at either the 5' position or the 6' position of the ring to which it is bound, is selected from the group consisting of H, self-labeling protein tag ligand, $CO_2H$, $CO_2CH_3$, $CO_2$t-Bu, N-hydroxysuccinimidyl (NHS) ester, and a targeting moiety; and $R_4$ is $CH_2OH$ or $CO_2H$, so long as when $R_4$ is $CO_2H$, then $Y_1$-$Y_4$ are selected from the group consisting of H and F $R_1$, and $R_2$ are F, and X is O.

As will be appreciated by the skilled artisan, the compounds disclosed herein will exist in equilibrium between an open form and a closed form and thus, a presentation of the compound in an open form is understood to be inclusive of the closed form, and a presentation of the compound in a closed form is understood to be inclusive of the open form.

For example, the following compound according to the presently-disclosed subject matter exists in an equilibrium between its open and closed forms:

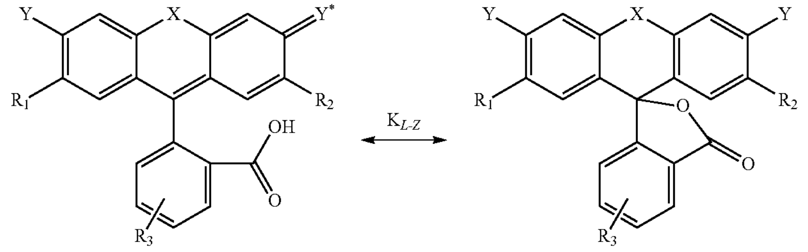

Open Form
Zwitterion (Z)

Closed Form
Lactone (L)

In this example, the open form is a zwitterion (Z) and the closed form is a lactone (L), and thus, the equilibrium constant is designated “$K_{L-Z}$.”

For another example, the following compound according to the presently-disclosed subject matter exists in an equilibrium between its open and closed forms:

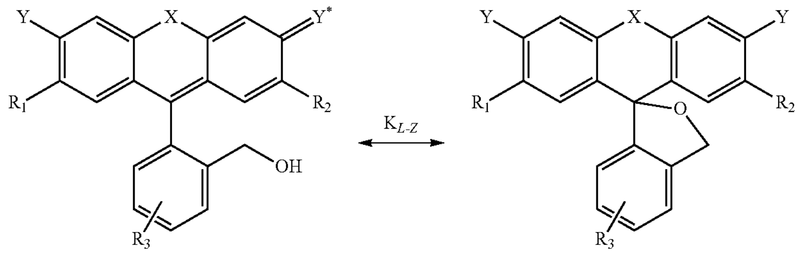

Open Form (Z) Closed Form (L)

In this example, although the closed form is not technically a lactone, for the purpose of consistency throughout the present document, the equilibrium constant will still be designated "$K_{L-Z}$," where it is understood that "L" refers to the closed form of the compound and "Z" refers to the open form of the compound.

In some embodiments of the presently-disclosed subject matter, a compound of the following formula is provided:

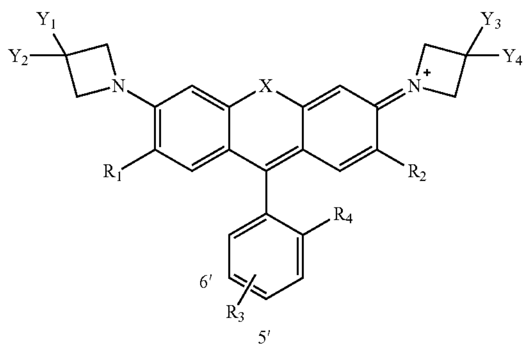

or

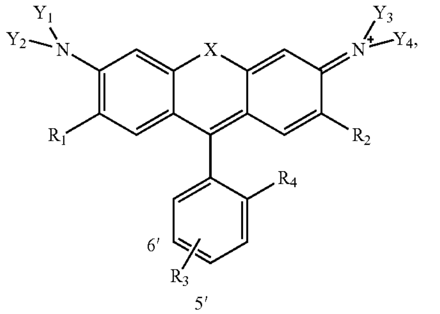

wherein $Y_1$-$Y_4$ are each independently selected from the group consisting of H, F, CN, $OCH_3$, $SO_2Me$, $CF_3$, $CH_3$, and $CO_2H$; X is selected from the group consisting of O,N-alkyl, S, $Si(alkyl)_2$, and $C(alkyl)_2$; $R_1$ and $R_2$ are each independently selected from the group consisting of H, alkyl, and halogen; $R_3$, which can be a substitution at either the 5' position or the 6' position of the ring to which it is bound, is selected from the group consisting of H, self-labeling protein tag ligand, $CO_2H$, $CO_2CH_3$, $CO_2$t-Bu, N-hydroxysuccinimidyl (NHS) ester, and a targeting moiety; and $R_4$ is $CH_2OH$ or $CO_2H$, so long as when $R_4$ is $CO_2H$, then $Y_1$-$Y_4$ are selected from the group consisting of H and F $R_1$, and $R_2$ are F, and X is O.

In some embodiments of the presently-disclosed subject matter, a compound of the following formula is provided:

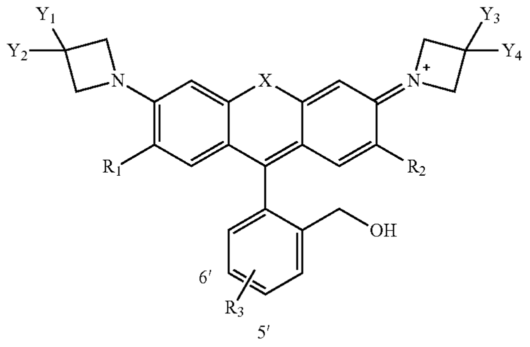

wherein $Y_1$-$Y_4$ are each independently selected from the group consisting of H, F, CN, $OCH_3$, $SO_2Me$, $CF_3$, $CH_3$, and $CO_2H$; X is selected from the group consisting of O,N-alkyl, S, $Si(alkyl)_2$, and $C(alkyl)_2$; $R_1$ and $R_2$ are each independently selected from the group consisting of H, alkyl, and halogen; and $R_3$, which can be a substitution at either the 5' position or the 6' position, is selected from the group consisting of H, self-labeling protein tag ligand, $CO_2H$, $CO_2CH_3$, $CO_2$t-Bu, N-hydroxysuccinimidyl (NHS) ester, and a targeting moiety.

In some embodiments of the presently-disclosed subject matter, a compound of the following formula is provided:

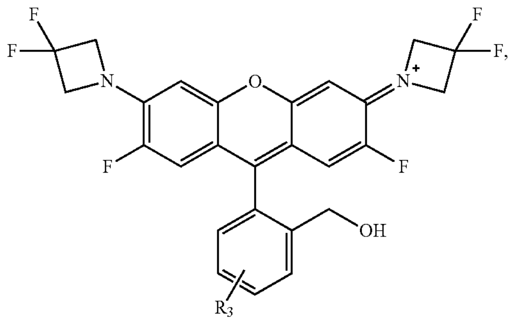

wherein $R_3$, which can be a substitution at either the 5' position or the 6' position, is selected from the group consisting of H, self-labeling protein tag ligand, $CO_2H$, $CO_2CH_3$, $CO_2$t-Bu, N-hydroxysuccinimidyl (NHS) ester, and a targeting moiety.

In some embodiments of the presently-disclosed subject matter, a compound of the following formula is provided:

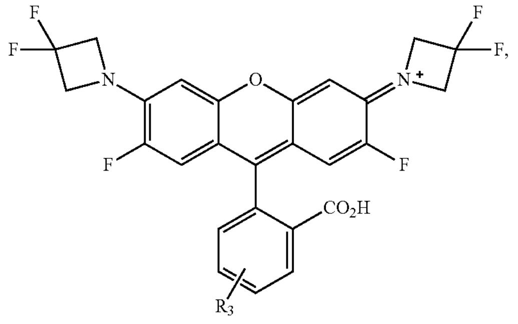

wherein $R_3$, which can be a substitution at either the 5' position or the 6' position, is selected from the group consisting of H, self-labeling protein tag ligand, $CO_2H$, $CO_2CH_3$, $CO_2$t-Bu, N-hydroxysuccinimidyl (NHS) ester, and a targeting moiety.

In some embodiments of the presently-disclosed subject matter, a compound of the following formula is provided:

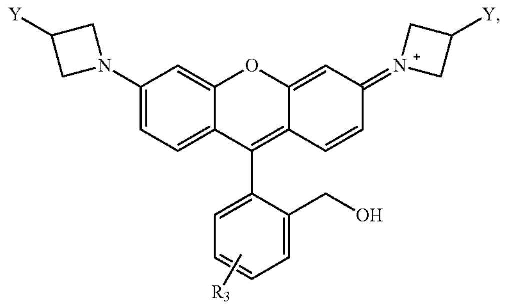

wherein $R_3$, which can be a substitution at either the 5' position or the 6' position, is selected from the group consisting of H, self-labeling protein tag ligand, $CO_2H$, $CO_2CH_3$, $CO_2$t-Bu, N-hydroxysuccinimidyl (NHS) ester, and a targeting moiety; and Y is H or F.

In some embodiments of the presently-disclosed subject matter, a compound of the following formula is provided:

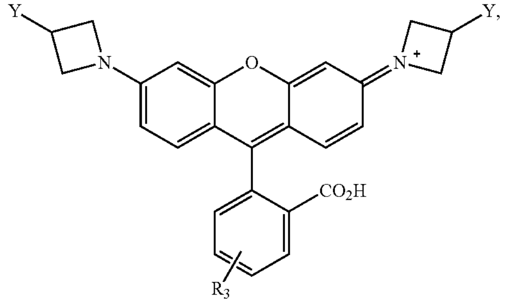

wherein $R_3$, which can be a substitution at either the 5' position or the 6' position, is selected from the group consisting of H, self-labeling protein tag ligand, $CO_2H$, $CO_2CH_3$, $CO_2$t-Bu, N-hydroxysuccinimidyl (NHS) ester, and a targeting moiety; and Y is H or F.

In some embodiments of the presently-disclosed subject matter, a compound of the following formula is provided:

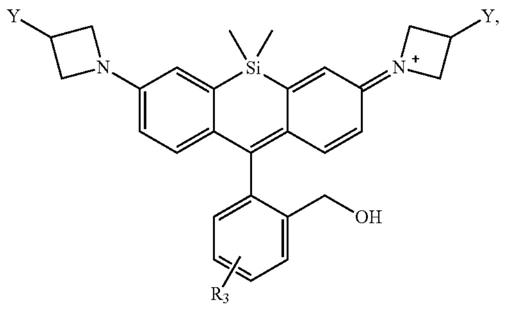

wherein $R_3$, which can be a substitution at either the 5' position or the 6' position, is selected from the group consisting of H, self-labeling protein tag ligand, $CO_2H$, $CO_2CH_3$, $CO_2$t-Bu, N-hydroxysuccinimidyl (NHS) ester, and a targeting moiety; and Y is H or F.

In some embodiments of the presently-disclosed subject matter, a compound of the following formula is provided:

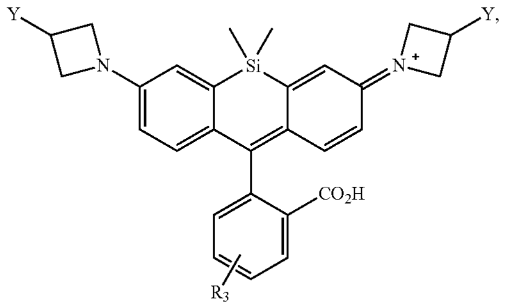

wherein $R_3$, which can be a substitution at either the 5' position or the 6' position, is selected from the group consisting of H, self-labeling protein tag ligand, $CO_2H$, $CO_2CH_3$, $CO_2$t-Bu, N-hydroxysuccinimidyl (NHS) ester, and a targeting moiety; and Y is H or F.

In some embodiments of the presently-disclosed subject matter, a compound of the following formula is provided:

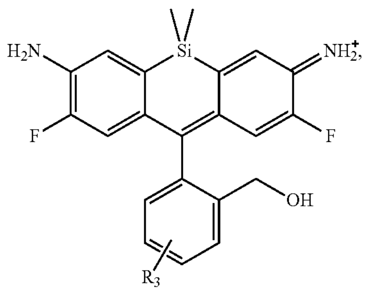

wherein $R_3$, which can be a substitution at either the 5' position or the 6' position, is selected from the group consisting of H, self-labeling protein tag ligand, $CO_2H$, $CO_2CH_3$, $CO_2$t-Bu, N-hydroxysuccinimidyl (NHS) ester, and a targeting moiety.

In some embodiments of the presently-disclosed subject matter, a compound of the following formula is provided:

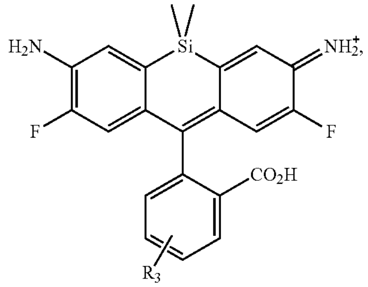

wherein $R_3$, which can be a substitution at either the 5' position or the 6' position, is selected from the group consisting of H, self-labeling protein tag ligand, $CO_2H$, $CO_2CH_3$, $CO_2t$-Bu, N-hydroxysuccinimidyl (NHS) ester, and a targeting moiety.

In some embodiments of the presently-disclosed subject matter, $R_3$ is a targeting moiety that is a self-labeling protein tag. In some embodiments of the presently-disclosed subject matter, $R_3$ is a targeting moiety for directing the compound to DNA, microtubules, or lysosomes. In some embodiments of the presently-disclosed subject matter, $R_3$ is a targeting moiety selected from the group consisting of trimethoprim, Taxol, Hoechst, and pepstatin A.

In some embodiments of the presently-disclosed subject matter, a compound of one of the following formulae is provided:

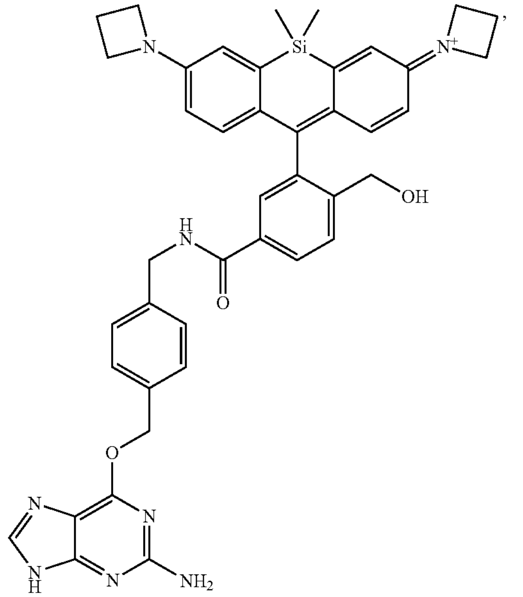

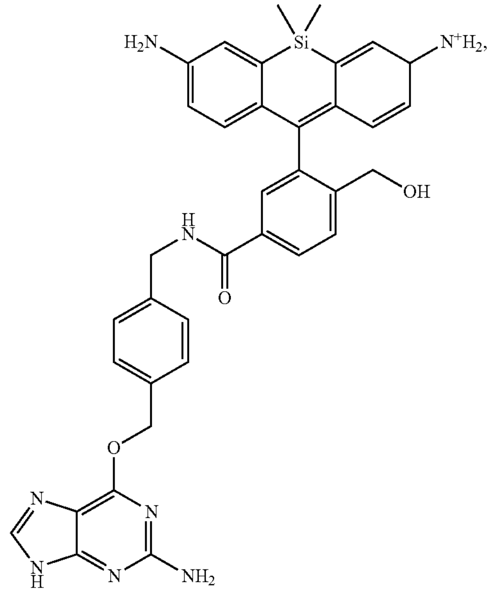

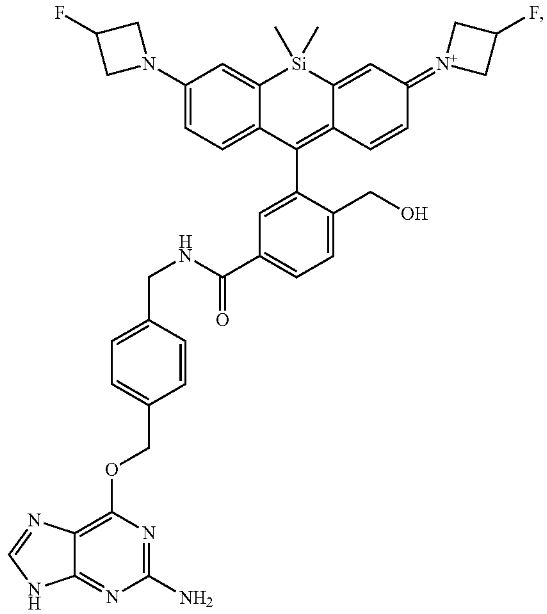

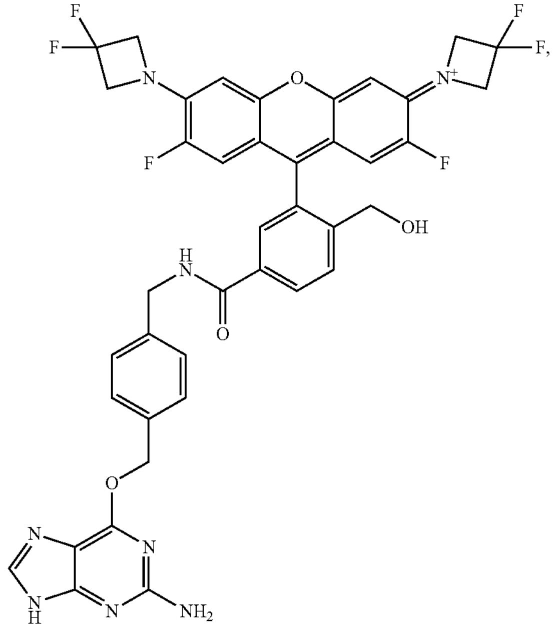

-continued
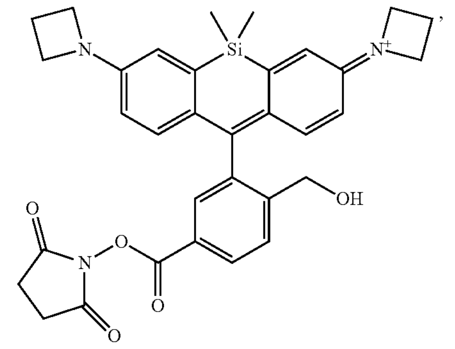
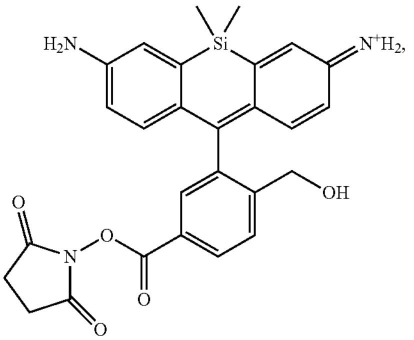
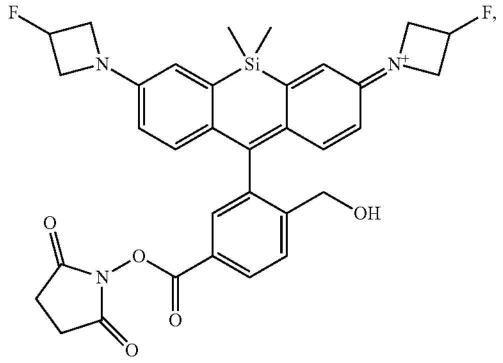
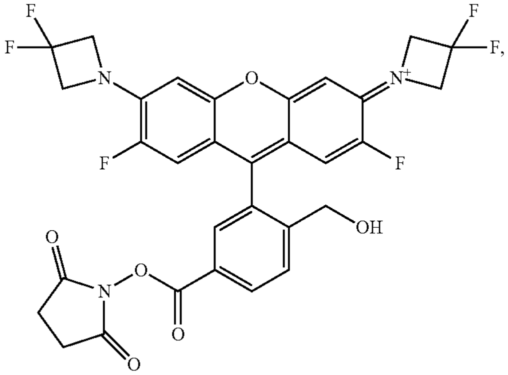
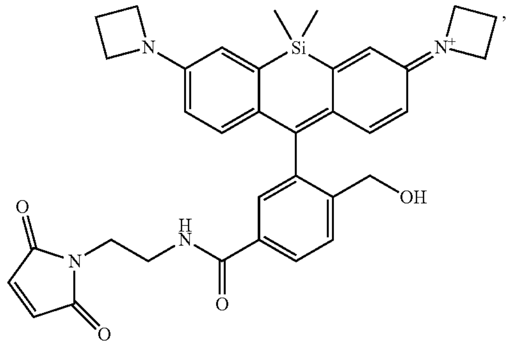
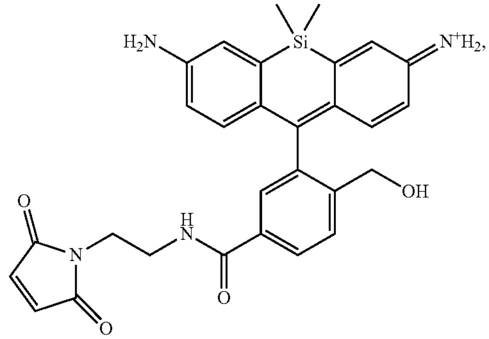
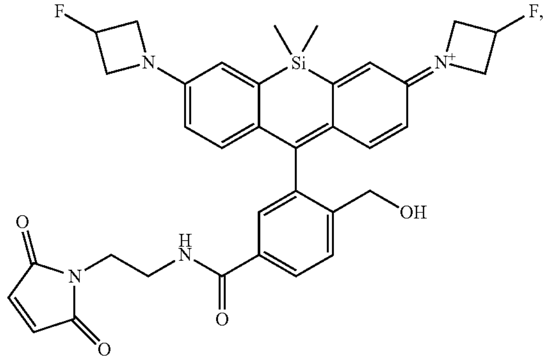
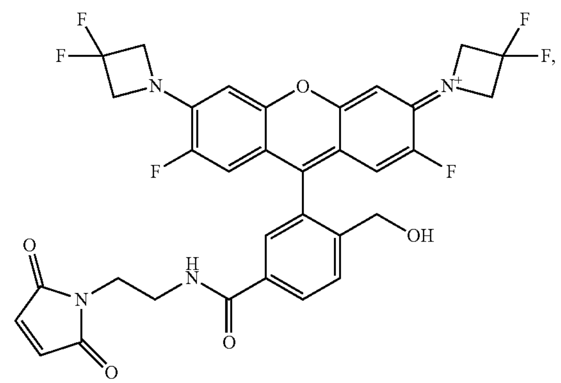

-continued
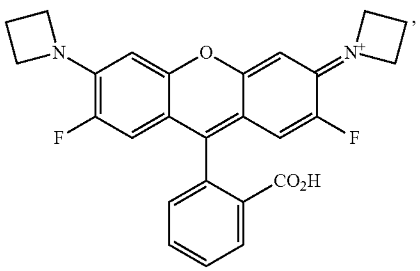
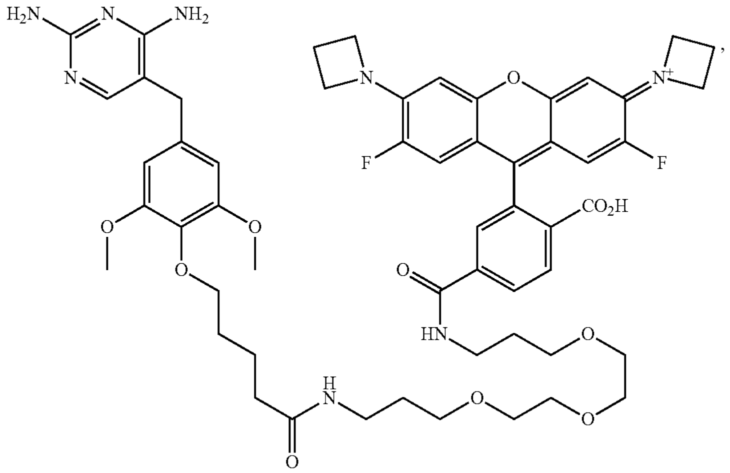
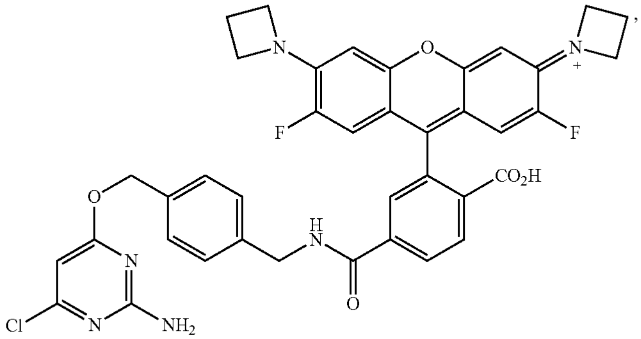
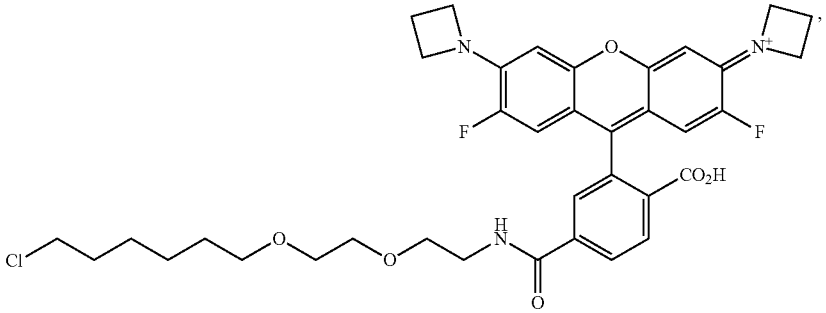
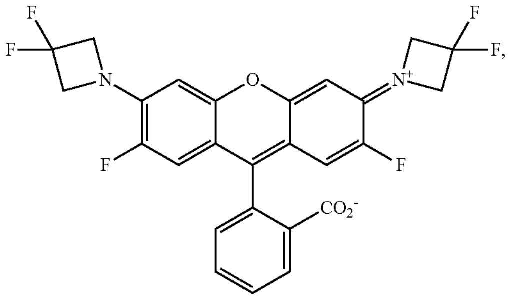

-continued
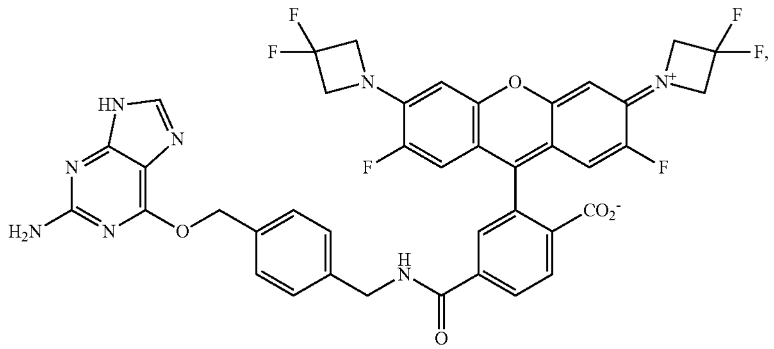
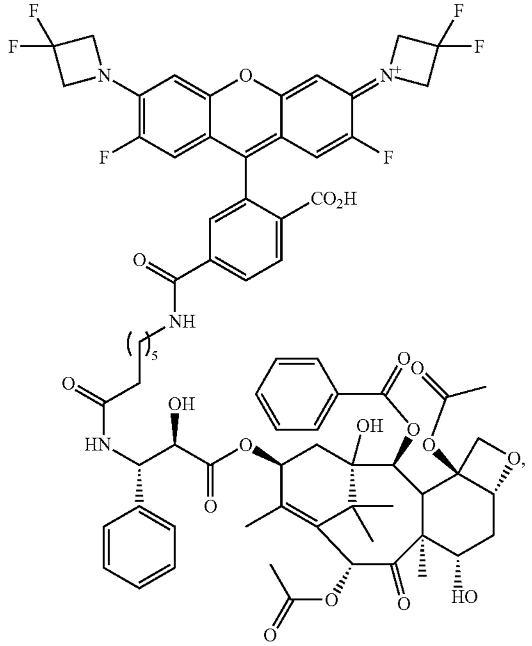
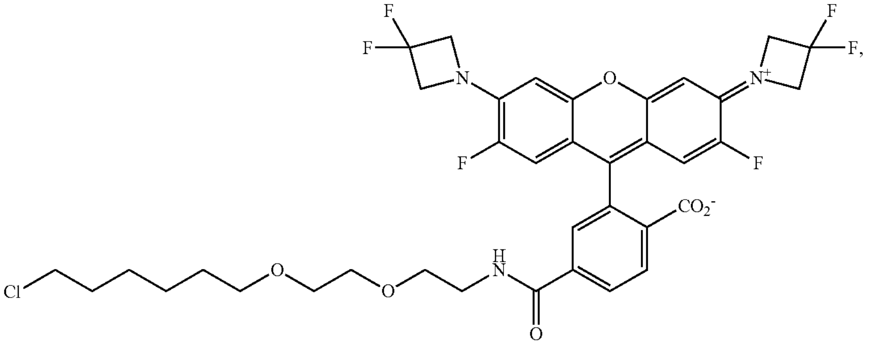
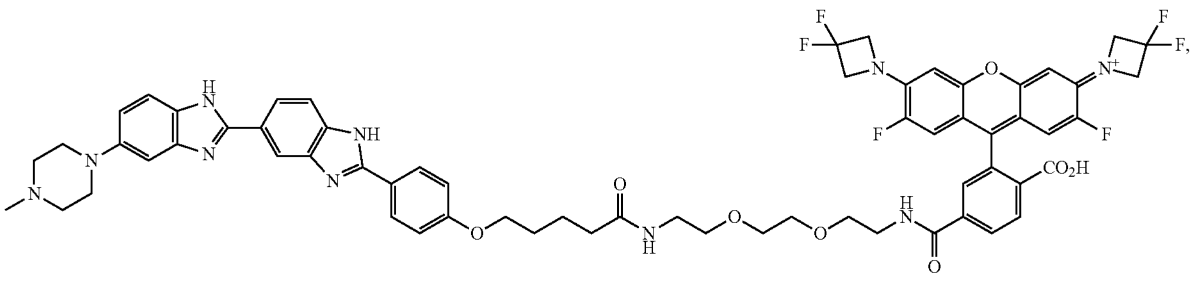

-continued

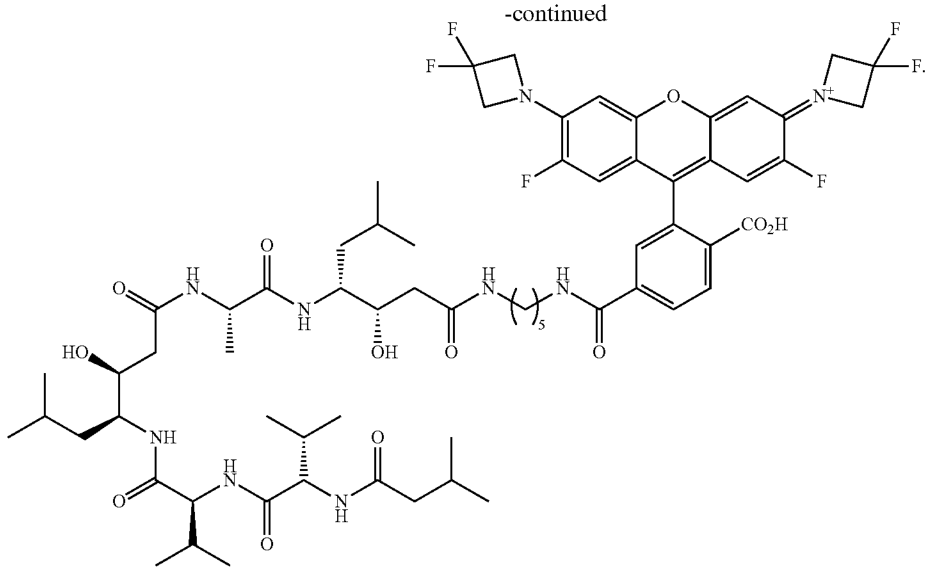

As noted hereinabove, a presentation of any compound herein in an open form is understood to be inclusive of the closed form, and a presentation of the compound in a closed form is understood to be inclusive of the open form. As such, with regard to all compounds presented herein as in the open form, such compounds are inclusive of the closed form, and vice versa. For example, the following exemplary compound is presented in the open form:

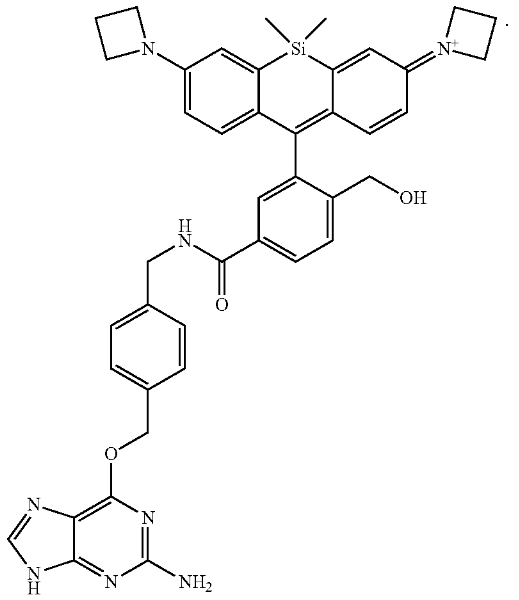 [SMILES: C[Si]1(C)C2=CC(=[N+]3CCC3)C=CC2=C(c2cc(C(=O)NCc3ccc(COc4nc(N)nc5[nH]cnc45)cc3)ccc2CO)c2ccc(N3CCC3)cc21]

However, such presentation in the open form should be understood to be inclusive of the closed form, as follows:

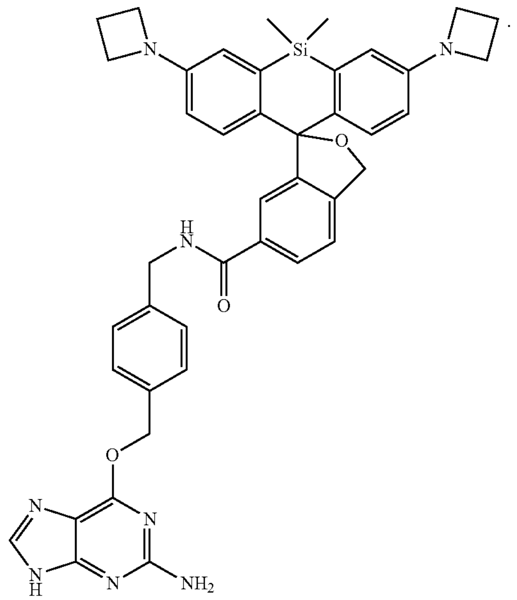 [SMILES: C[Si]1(C)c2cc(N3CCC3)ccc2C2(OCc3ccc(C(=O)NCc4ccc(COc5nc(N)nc6[nH]cnc56)cc4)cc32)c2ccc(N3CCC3)cc21]

The following are additional examples of closed forms of compounds that are captured by the presentation of the open forms of the compounds hereinabove:

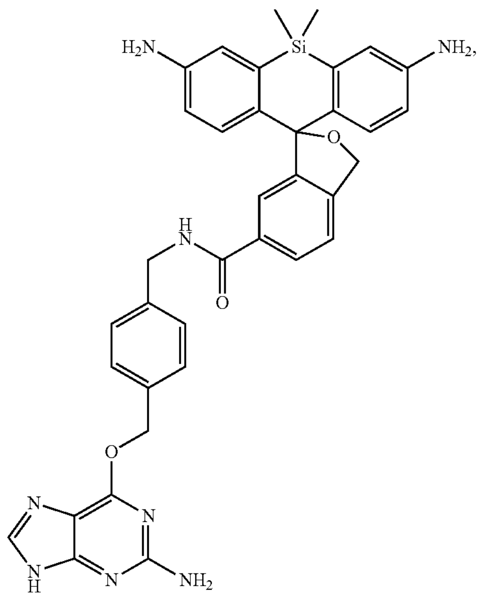
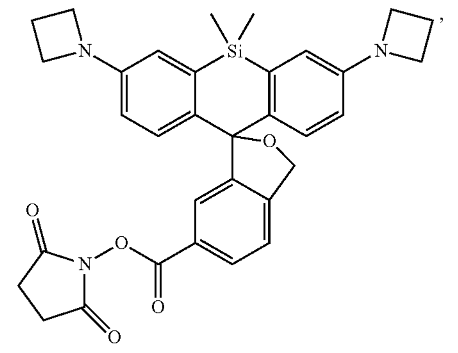
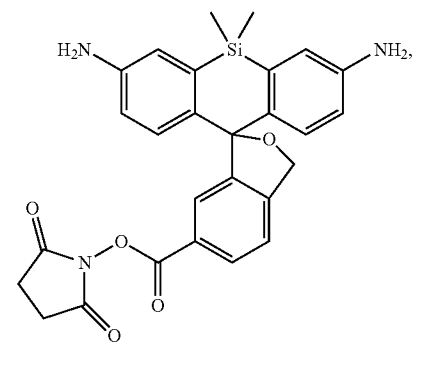
-continued
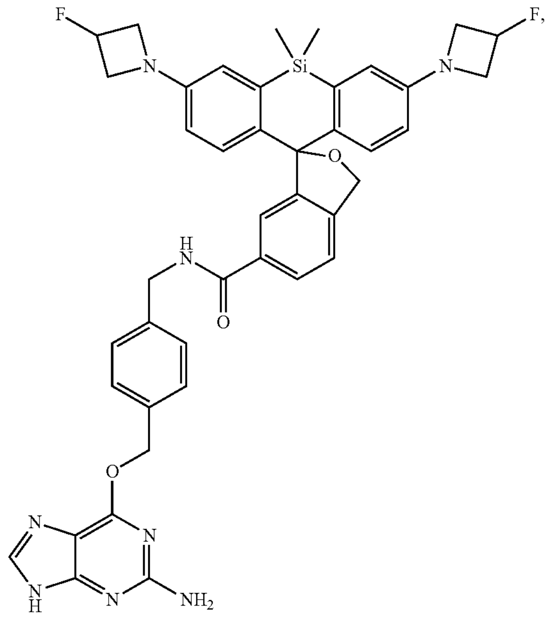
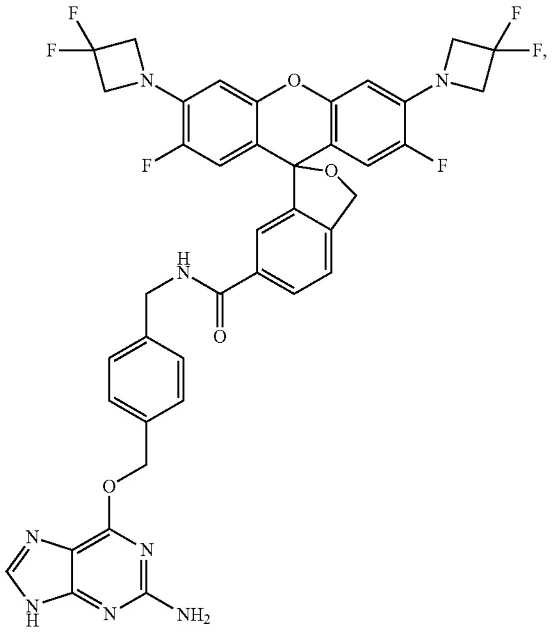
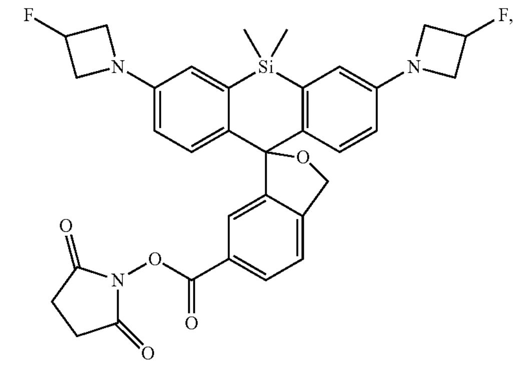

-continued

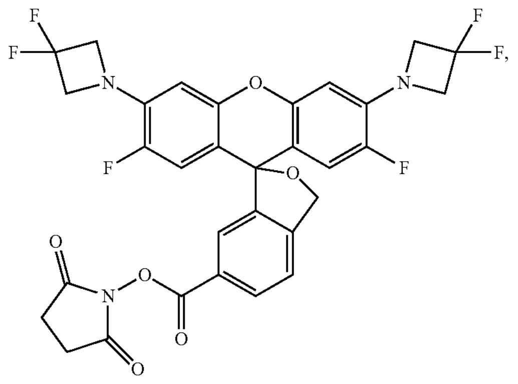

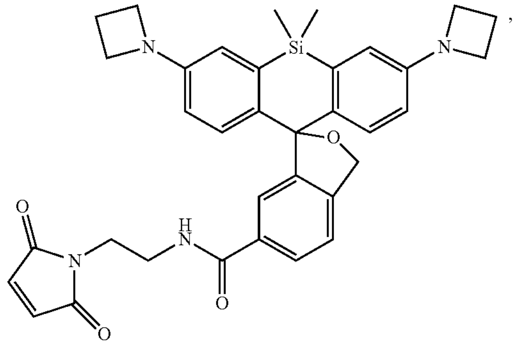

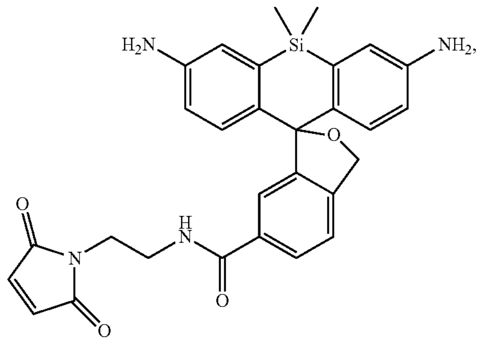

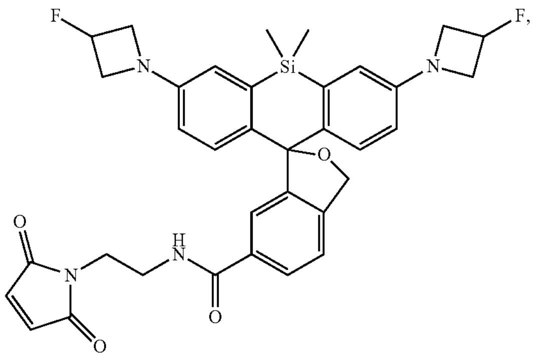

and

-continued

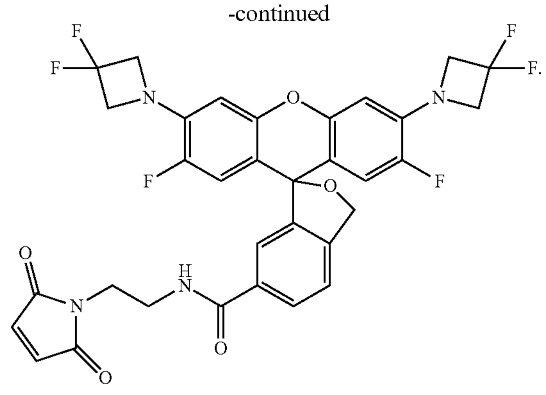

The presently-disclosed subject matter is further inclusive of methods for using the present compounds and their intermediates, as well as methods for preparing such compounds and the their intermediates.

In some embodiments of the presently-disclosed subject matter, a detection method is provided. An exemplary method provides for the detection of a target substance, and involves contacting a sample with a compound as disclosed herein, and detecting an emission light from the compound. The emission light can indicate the presence of the target substance and the intesity of the emission light can indicate the relative amount of the target substance.

In some embodiments of the detection method, the target substance is selected from a protein, a carbohydrate, a polysaccharide, a glycoprotein, a hormone, a receptor, an antigen, an antibody, a virus, a substrate, a metabolite, an inhibitor, a drug, a nutrient, a growth factor, a lipoprotein, and a combination thereof.

In some embodiments of the detection method, the detecting step is performed with a microscope. In some embodiments, the contacting step and the detecting step are performed in a live cell.

In some embodiments, the detection method also involves a step of exposing the compound to an absorption light that includes a wavelength of about 100 nm to about 1000 nm.

In some embodiments of the method, the compound includes a first compound and a second compound, where the first compound is selective for a first target substance and is capable of emitting a first emission light, and the second compound is selective for a second target substance and is capable of emitting a second emission light. The detecting step includes detecting the first emission light that indicates the presence of the first target substance and the second emission light that indicates the presence of the second target substance.

While the terms used herein are believed to be well understood by those of ordinary skill in the art, certain definitions are set forth to facilitate explanation of the presently-disclosed subject matter.

The term "alkyl" as used herein is a branched or unbranched saturated hydrocarbon group of 1 to 24 carbon atoms, such as methyl, ethyl, n-propyl, isopropyl, n-butyl, isobutyl, s-butyl, t-butyl, n-pentyl, isopentyl, s-pentyl, neopentyl, hexyl, heptyl, octyl, nonyl, decyl, dodecyl, tetradecyl, hexadecyl, eicosyl, tetracosyl, and the like. The alkyl group can be cyclic or acyclic. The alkyl group can be branched or unbranched. The alkyl group can also refer to both substituted or unsubstituted alkyls. For example, the alkyl group can be substituted with one or more groups including, but not limited to, optionally substituted alkyl, cycloalkyl, alkoxy, amino, ether, halide, hydroxy, nitro, silyl, sulfo-oxo, or thiol, as described herein. A "lower alkyl" group is an alkyl group containing from one to six (e.g., from one to four) carbon atoms.

The term "halide" or "halogen" refers to at least one of the halogens selected from fluorine, chlorine, bromine, and iodine.

The term "self-labeling protein tag" will be understood by those of ordinary skill in the art, and refers to a protein tag that catalyses the attachment of an exogenously added synthetic ligand. Examples of self-labeling tags include HaloTag, SNAP-tag, CLIP-tag, and TMP-tag.

The term "self-labeling protein tag ligand" refers to a synthetic ligand that selectively bind to a self-labeling protein tag. As will be appreciated by those of ordinary skill in the art, such synthetic ligands are tag-specific and can be coupled to various labels, such as, for example, labels that are fluorescent dyes. By way of an example, the ligand for HaloTag has the structure

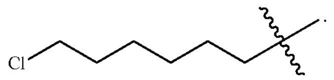 [SMILES: *CCCCCCCl]

For another example, the ligand for SNAP-tag has one of the structures selected from

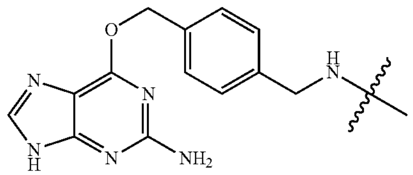

and

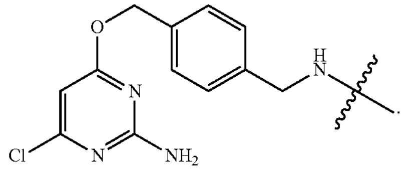 [SMILES: *NCc1ccc(COc2cc(Cl)nc(N)n2)cc1]

For another example, the ligand for CLIP-tag has the structure

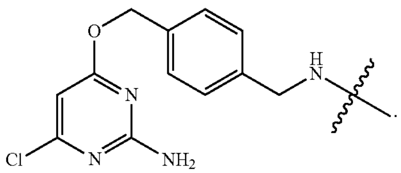

For yet another example, the ligand for TMP-tag has the structure

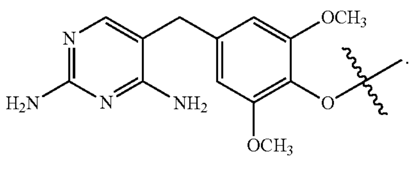 [SMILES: *Oc1c(OC)cc(Cc2cnc(N)nc2N)cc1OC]

The term "targeting moiety" refers to is a moiety or group of certain embodiments of the presently-disclosed compounds, which selectively binds to a target substance. In some embodiments, for example, the targeting moiety can include chemical small molecule, a nucleotide, or a polypeptide that selectively binds to a target substance.

The term "target substance" refers to a substance that is selectively bound directly by the presently-disclosed compounds and/or indirectly by a molecule that is bound to the present compound. A target substances can include, but is not limited to, a protein, carbohydrates, polysaccharide, glycoprotein, hormone, receptor, antigen, antibody, virus, substrate, metabolite, inhibitor, drug, nutrient, growth factor, and the like. In some embodiments the target substance refers to an entire molecule, and in other embodiments the target substances refers to a site on a molecule, such as a binding site on a particular protein.

The terms "selectively bind" or "selectively bound" are used herein to refer to the property of an atom, moiety, and/or molecule preferentially being drawn to or binding a particular compound. In some instances the atom, moiety, and/or molecule selectively binds to a particular site on a compound, such as an active site on a protein molecule.

Unless defined otherwise, all technical and scientific terms used herein have the same meaning as is commonly understood by one of skill in the art to which the invention(s) belong.

All patents, patent applications, published applications and publications, GenBank sequences, databases, websites and other published materials referred to throughout the entire disclosure herein, unless noted otherwise, are incorporated by reference in their entirety.

Where reference is made to a URL or other such identifier or address, it understood that such identifiers can change and particular information on the internet can come and go, but equivalent information can be found by searching the internet. Reference thereto evidences the availability and public dissemination of such information.

As used herein, the abbreviations for any protective groups, amino acids and other compounds, are, unless indicated otherwise, in accord with their common usage, recognized abbreviations, or the IUPAC-IUB Commission on Biochemical Nomenclature (see, Biochem. (1972) 11(9): 1726-1732).

Although any methods, devices, and materials similar or equivalent to those described herein can be used in the practice or testing of the presently-disclosed subject matter, representative methods, devices, and materials are described herein.

In certain instances, nucleotides and polypeptides disclosed herein are included in publicly-available databases, such as GENBANK® and SWISSPROT. Information including sequences and other information related to such nucleotides and polypeptides included in such publicly-available databases are expressly incorporated by reference. Unless otherwise indicated or apparent the references to such publicly-available databases are references to the most recent version of the database as of the filing date of this Application.

Following long-standing patent law convention, the terms "a", "an", and "the" refer to "one or more" when used in this application, including the claims. Thus, for example, reference to "a cell" includes a plurality of such cells, and so forth.

Unless otherwise indicated, all numbers expressing quantities of ingredients, properties such as reaction conditions, and so forth used in the specification and claims are to be understood as being modified in all instances by the term "about". Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, concentration or percentage is meant to encompass variations of in some embodiments±20%, in some embodiments±10%, in some embodiments±5%, in some embodiments±1%, in some embodiments±0.5%, in some embodiments±0.1%, in some embodiments±0.01%, and in some embodiments±0.001% from the specified amount, as such variations are appropriate to perform the disclosed method.

As used herein, ranges can be expressed as from "about" one particular value, and/or to "about" another particular value. It is also understood that there are a number of values disclosed herein, and that each value is also herein disclosed as "about" that particular value in addition to the value itself. For example, if the value "10" is disclosed, then "about 10" is also disclosed. It is also understood that each unit between two particular units are also disclosed. For example, if 10 and 15 are disclosed, then 11, 12, 13, and 14 are also disclosed.

As used herein, "optional" or "optionally" means that the subsequently described event or circumstance does or does not occur and that the description includes instances where said event or circumstance occurs and instances where it does not. For example, an optionally variant portion means that the portion is variant or non-variant.

The presently-disclosed subject matter is further illustrated by the following specific but non-limiting examples. The following examples may include compilations of data that are representative of data gathered at various times during the course of development and experimentation related to the present invention.

EXAMPLES

UV-vis and fluorescence spectroscopy. Fluorescent molecules for spectroscopy were prepared as stock solutions in DMSO and diluted such that the DMSO concentration did not exceed 1% v/v. Spectroscopy was performed using 1-cm path length, 3.5-mL quartz cuvettes or 1-cm path length, 1.0-ml quartz microcuvettes (Starna Cells). All measurements were taken at ambient temperature (22±2° C.). Absorption spectra were recorded on a Cary Model 100 spectrometer (Agilent). Fluorescence spectra were recorded on a Cary Eclipse fluorometer (Varian). Maximum absorption wavelength ($\lambda_{abs}$), extinction coefficient (εw), and maximum emission wavelength ($\lambda_{em}$) were taken in 10 mM HEPES, pH 7.3 buffer unless otherwise noted; reported values for ew are averages (n=3). Normalized spectra are shown for clarity.

Determination $K_{L-Z}$ and $\varepsilon_{max}$. The lactone-zwitterion equilibrium constant ($K_{L-Z}$) was calculated as described previously[18,41] using equation 1:

$$K_{L-Z}=(\varepsilon_{dw}/\varepsilon_{max})/(1-\varepsilon_{dw}/\varepsilon_{max}) \quad (1)$$

where $\varepsilon_{dw}$ is the extinction coefficient of the dyes in a 1:1 (v/v) dioxane:water solvent mixture containing 0.01% (v/v) triethylamine; the dioxane-water mixture was chosen to give a large range of $K_{L-Z}$ values and the triethylamine additive ensures the rhodamines are in the net neutral form. The emax (maximal extinction coefficient) values were measured in 0.1% (v/v) trifluoroacetic acid (TFA) in 2,2,2-trifluoroethanol (TFE) for rhodaminc 10, and 0.1% (v/v) TFA in ethanol for the Si-rhodamine 8.

Quantum yield determination. All reported absolute fluorescence quantum yield values (Φ) were measured in the laboratory under identical conditions using a Quantaurus-QY spectrometer (model C11374, Hamamatsu). This instrument uses an integrating sphere to determine photons absorbed and emitted by a sample. Measurements were carried out using dilute samples (A<0.1) and self-absorption corrections were performed using the instrument software[57] when appropriate. Reported values are averages (n=3).

Measurement of increase in absorption of HaloTag ligands 1HTL-10HTL following attachment to HaloTag protein. HaloTag protein was prepared as a 100 μM solution in 75 mM NaCl, 50 mM TRIS·HCl, pH 7.4. Absorption measurements were performed in 1.0-mL quartz cuvettes. HaloTag ligands (5 μM) were dissolved in 10 mM HEPES, pH 7.3 containing 0.1 mg/mL CHAPS. An aliquot of HaloTag protein (75 μL, 7.5 μM, 1.5 equiv) or an equivalent volume of buffer (75 mM NaCl, 50 mM TRIS·HCl, pH 7.4) was added and the resulting mixture was incubated until a consistent absorption signal was observed (~60 min). Absorption scans are averages (n=2).

Measurement of increase in fluorescence of HaloTag ligands 1HTL-10HTL following attachment to HaloTag protein. Fluorescence measurements were performed on an Infinite M1000 Pro microplate reader (Tecan) and a 96-well quartz microplate (Hellma). HaloTag ligands (2 μM) were dissolved in 10 mM HEPES, pH 7.3 containing 0.1 mg/ml CHAPS. An aliquot of HaloTag protein (5 μM, 2.5 equiv) or an equivalent volume of buffer (75 mM NaCl, 50 mM Tris, pH 7.4) was added and the resulting mixture was incubated for 3 h followed by measurement of fluorescence. Fluorescence readings are averages (n=2).

Measurement of increase in absorbance and fluorescence of 10HST following binding DNA. 10HST (5 μM) was added to phosphate buffered saline (PBS; pH 7.4) containing no DNA (blank), a DNA duplex with sequences 5'-A20-3' and 5'-T20-3' (polyA·polyT; i.e., DNAAT; 50 μM; Integrated DNA Technologies), or a DNA duplex with sequences 5'-G20-3' and 5'-C20-3' (polyG·polyC; i.e., DNAGC; 50 μM; Integrated DNA Technologies). These solutions were incubated for 2 h at ambient temperature, followed by measurement of absorption spectra. The solutions were then diluted to 500 nM in PBS for measurement of fluorescence spectra or diluted to 1.25 μM in PBS for measurement of quantum yield. Found: 10HST Φ=0.009; 10HST·DNAAT Φ=0.126; 10HST·DNAGC Φ=0.040.

Measurement of increase in fluorescence of Taxol conjugates 1TXL, 7TXL, and 10TXL following binding to polymerized tubulin. In vitro assays were performed as previously described.[27] Briefly, 1TXL, 7TXL, or 10TXL (3 μM) was added to a solution of monomeric tubulin (2 mg/mL) or bovine serum albumin (BSA, 2 mg/mL) in microtubule polymerization buffer. The microtubule polymerization buffer contained: 80 mM piperazine-N,N'-bis(2-ethanesulfonic acid) sequisodium salt (PIPES), 2 mM MgCl2, 0.5 mM ethylene glycol-bis(β-aminoethyl ether) N,N,N',N'-tetraacetic acid (EGTA, pH 6.9), 1 mM GTP and 15% glycerol. Purified tubulin, BSA, and buffer are components of the tubulin polymerization assay kit (Cytoskeleton). The samples were incubated for 2-3 h at 37° C. and fluorescence spectra were measured on a Cary Eclipse fluorometer (Varian).

General cell culture. COS7 cells and U2OS cells were obtained from ATCC. To prepare cells stably expressing histone H2B-HaloTag, U2OS cells were integrated with a histone H2B-HaloTag expressing plasmid via the piggyback transposase. To prepare cells stably expressing histone H2B-SNAP-tag, COS7 cells were integrated with a histone H2B-SNAP-tag expressing plasmid via the piggyback transposase. Cells were cultured in Dulbecco's modified Eagle medium (DMEM, phenol red-free; Life Technologies) supplemented with 10% v/v FBS (Life Technologies), 1 mM GlutaMAX (Life Technologies) and plated in 35-mm glass bottom dishes (MatTek). Cells were maintained at 37° C. in a humidified 5% (v/v) CO2 environment. All cell lines undergo regular *mycoplasma* testing by the Janelia Cell Culture Facility.

Comparison of HaloTag ligands $6_{HTL}$ and $9_{HTL}$. in live yeast. A *S. cerevisiae* strain expressing a histone H2A.Z-HaloTag fusion under natural promoter control was created; the PDR5 transporter gene was also deleted for improved cellular retention of fluorescent ligands. Cells were grown to early log phase and incubated with either $JF_{552}$-HaloTag ligand (9HTL; 10 nM) or $JF_{549}$-HaloTag ligand (6HTL; 10 nM) for 2 h. Free ligand was removed by three washes in culture media and the live cells were imaged by wide-field fluorescence microscopy at ambient temperature.

Comparison of TMP ligands $6_{TMP}$ and $9_{TMP}$ in live cells. COS7 cells were transfected with a plasmid to express a histone H2B-*E. coli* dihydrofolate reductase (eDHFR) fusion protein using λmaxa Nucleofector (Lonza). Live cells were stained with ligands $6_{TMP}$ or $9_{TMP}$ (200 nM) for 4 h. Cells were washed twice before imaging with an LSM880 confocal microscope (Zeiss; excitation: 514 nm/emission: 526-615 nm). Signal to background (S/B) ratio was determined using the mean fluorescence of the nuclei relative to a region adjacent to each nuclei using Fiji.[58]

Comparison of HaloTag ligands $7_{HTL}$ and $10_{HTL}$ in live cells. U2OS cells expressing histone H2B-HaloTag were incubated with 500 nM of $7_{HTL}$ or $10_{HTL}$ for 30 min and imaged with an LSM880 confocal microscope (Zeiss; excitation: 514 nm/emission: 526-615 nm) without intermediate washing steps. Signal to background (S/B) ratio was determined using the mean fluorescence of the nuclei relative to a region adjacent to each nuclei using Fiji.[58]

Comparison of SNAP ligands $7_{STL}$ and $10_{STL}$ in live cells. COS7 cells expressing histone H2B-SNAP-tag were incubated with 1 μM $7_{STL}$ or $10_{STL}$ for 1 h and imaged with an LSM880 confocal microscope (Zeiss; excitation: 514 nm/emission: 526-615 nm) without intermediate washing steps. Signal to background (S/B) ratio was determined using the mean fluorescence of the nuclei relative to a region adjacent to each nuclei using Fiji.[58]

Live cell staining with ligands $10_{HST}$, $10_{TXL}$, and $10_{PEP}$. For FIG. 5B, U2OS cells were stained with $JF_{526}$-Hoechst ($10_{HST}$, 4 μM). For FIG. 5C, mouse primary hippocampal neurons were stained with $JF_{526}$ Taxol ($10_{TXL}$, 1 μM) and $JF_{646}$-Hoechst[46] (2HST, 1 μM). For FIG. 5D, U2OS cells stably expressing histone H2B-HaloTag were stained with $JF_{526}$-pepstatin A ($10_{PEP}$, 2 M), $JF_{585}$-HaloTag ligand[41] ($5_{HTL}$, 100 nM), SiR-tubulin[27] ($1_{HTL}$, Spirochrome, 1 μM), and Verapamil (10 μM). Verapamil was used to improve staining by preventing efflux of the Taxol conjugates.[27] For all samples, cells were incubated with the stains for 1 h and imaged without intermediate washing steps. Imaging was performed on a LSM880 confocal microscope (Zeiss) using the following configuration: excitation: 514 nm/emission: 526-615 nm ($JF_{526}$); excitation: 594 nm/emission: 599-734 nm ($JF_{585}$); excitation: 633 nm/emission: 638-759 nm ($JF_{646}$ or SiR).

Imaging with lattice light-sheet microscope. U2OS cells were stained with 10PEP (2 μM) and 2HST (4 μM) for 1 h before imaging on a custom-built lattice light sheet microscope (LLSM).[48] Imaging was performed using 532 nm (for JF526) and 642 nm (for JF646) excitation, and a multi-band pass emission filter (NF03-405/488/532/635E, Semrock). Data were acquired by serial scanning the entire cell through the light sheet at 30 ms exposure per 2D image and 400 nm z-steps resulting in a 3D imaging rate of 6 s per volume. All acquired data were deconvolved by using a Richardson-Lucy algorithm adapted to run on a graphics processing unit, using an experimentally measured PSF for each emission wavelength[48].

Imaging with structured illumination microscopy. Mouse primary hippocampal neurons were stained with 10PEP (2 μM) and 2HST[6] (4 μM, 1 h) before three-dimensional structured illumination microscopy (3D-SIM) using a custom-built microscope.[45,59] Briefly, the 3D-SIM microscope was built on a Zeiss Axio Observer inverted microscope platform with an ASI motorized stage and a 100×/1.46 NA oil immersion Zeiss objective (Alpha Plan-APO). Two-color imaging was performed at 488 nm and 647 nm excitation for JF526 and JF646, respectively. Sequential excitation at the two wavelengths was enabled by a software-controlled filter wheel (Finger Lakes Instrumentation). Excitation grating patterns at each wavelength were generated by a spatial light modulator (Forth Dimension Display) as previously described.[45] Fluorescence images were collected using an sCMOS camera (Hamamatsu Flash 4.0) with an exposure time of 30 ms. 3D reconstruction of the raw data was performed using a custom software as previously described.[45,59]

Imaging with stimulated emission depletion microscopy (STED). For one-color STED, U2OS cells were stained with JF526-Taxol ($10_{TXL}$, 1 μM) and Verapamil (10 μM) for 1 h before imaging using STED microscopy. For three-color STED, U2OS cells expressing TOMM20-HaloTag fusion protein were transfected with Sec61β-pSNAPf plasmids using Lipofectamine 2000 (ThermoFisher). Sec61β encodes an endoplasmic reticulum membrane protein translocator protein, and TOMM20 encodes an outer mitochondrial membrane protein as part of a protein translocase complex. Live cells were simultaneously stained with JF646-SNAP-tag ligand (3 μM with 0.2% (w/v) Pluronic F-127) and JF585-HaloTag ligand (100 nM) for 3 h. Cells were washed two times with DMEM media and stained with JF526-Taxol ($10_{TXL}$, 1 μM) and Verapamil (10 μM) for 1 h before imaging with STED microscopy. STED images were acquired using a Leica TCS SP8 confocal laser scanning microscopy platform using the following configuration: 532 nm/emission: 540-592 nm (JF526); excitation: 594 nm/emission: 597-643 nm ($JF_{585}$); excitation: 640 nm/emission: 650-699 nm (JF646). A 775 nm pulsed laser was used as the depletion source to generate STED images. Fluorescence images were collected using HyD detectors.

Labeling of secondary antibody with N-hydroxysuccinimide esters of HM-$JF_{526}$. Goat anti-mouse IgG secondary antibody (IgG, Thermo Fisher) was used as the secondary antibody for immunofluorescence labeling. IgG was concentrated to 5 mg/mL using an Amicon Ultra 0.5 mL centrifugal filter. HM-JF526-NHS (37) was dissolved in DMSO to yield a 10 mM stock solution. IgG was incubated with HM-JF526-NHS (20 equiv.) in PBS pH 7.4/1 M sodium bicarbonate pH 8.3 (9:1 v/v) at room temperature for 90 min. Proteins labeled with dyes were purified using a PD MiniTrap™ G-25 (GE Healthcare) with PBS (pH 7.4) as the eluent. The degree of labeling (DOL) ratio (dye/protein) was determined by measuring the absorption of the labeled-IgG at pH 2, where the HM-$JF_{526}$ exists in the open, colored form. The DOL of HM-JF526-IgG was 2.8.

Sample preparation for single-molecule localization microscopy. Tubulin was immunolabeled as previously described.[41] U2OS cells were grown in 35-mm glass bottom dishes (MatTek) to appropriate density. Cells were washed twice with 60 mM PIPES, 25 mM HEPES, 10 mM EGTA, 2 mM MgCl2 (PHEM), followed by fixation with fresh 0.1% glutaraldehyde and 2% paraformaldehyde for 15 min at 37° C., and three additional washes with PHEM for 10 min each. Cells were then permeabilized with 0.1% Triton X-100 for 2 min and washed 3 times with PHEM for 10 min each. Incubating in PBS with 1% bovine serum albumin (BSA) and 1 mg/mL lysine for 30 min blocked nonspecific protein binding sites. A primary monoclonal antibody against alpha-tubulin (DM1A, ThermoFisher) was bound to the cells at 4 μg/mL in PBS with 1% BSA and 0.05% Tween for 30 min with shaking. After three 10 min washes with PBS, the secondary antibody was applied at 3 g/ml for 30 min with shaking. After another three 10 min washes with 0.05% Tween in PBS, cells were imaged in PBS.

TOMM20 proteins were immunolabeled as previously described.[60] U2OS cells were fixed with 3.7% PFA solution with occasional gentle agitation before aspiration with minimal perturbation. Five PBS washes were administered lasting approximately 0.5, 1, 5, 10 and 15 minutes each. 0.1% Triton X-100 in PBS is used to permeabilize the cells. Following permeabilization, cells were again washed in PBS, once for 30 s and then twice for 5 min. Blocking was achieved using 1% BSA in PBS. A primary mouse monoclonal antibody against TOMM20 (F-10, Santa Cruz Biotech) was bound to the cells at 2 μg/mL in PBS with 1% BSA for 30 min with shaking. After three 5 min washes with PBS, the secondary antibody was applied at 3 μg/ml for 30 min with shaking. After three 5 min washes with PBS, cells were imaged in PBS.

Single-molecule localization microscopy. All single-molecule localization microscopy (SMLM) experiments were performed on an ELYRA system (Carl Zeiss) with a 100×/1.42 NA Plan-Apo objective, as previously described.[39] For correction of sample drift, 100-nm TetraSpeck Microspheres (Invitrogen) were affixed to the cover-glass by incubation in the medium for 30 min at room temperature. Images were taken by a Highly Inclined and Laminated Optical sheet (HILO) microscope coupled to an EMCCD camera that can detect a single photon. Imaging was performed at room temperature in PBS buffer. SMLM images were collected with 10,000 cycles of excitation at a constant illumination power density of around 10 kW/cm$^2$ for 561 nm excitation laser. The exposure time for each cycle was 30 ms. The SMLM data were analyzed with Zeiss Zen software to reconstruct the SMLM images.

Figure 1A:
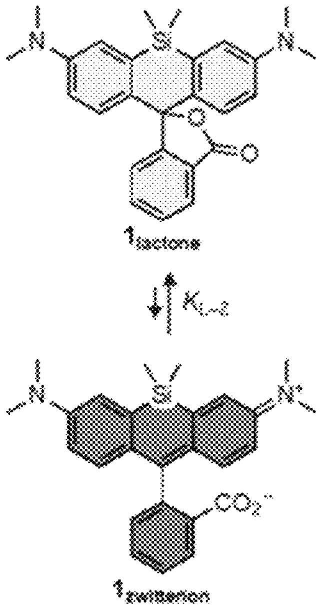
FIGS. 1A-1E. Fluorogenicity of rhodamines.
Figure 1B:
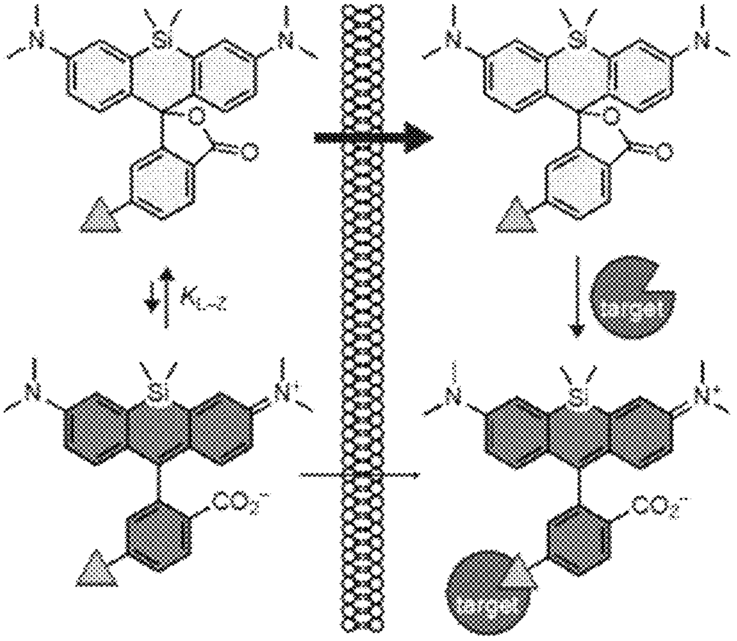
Figure 1C:
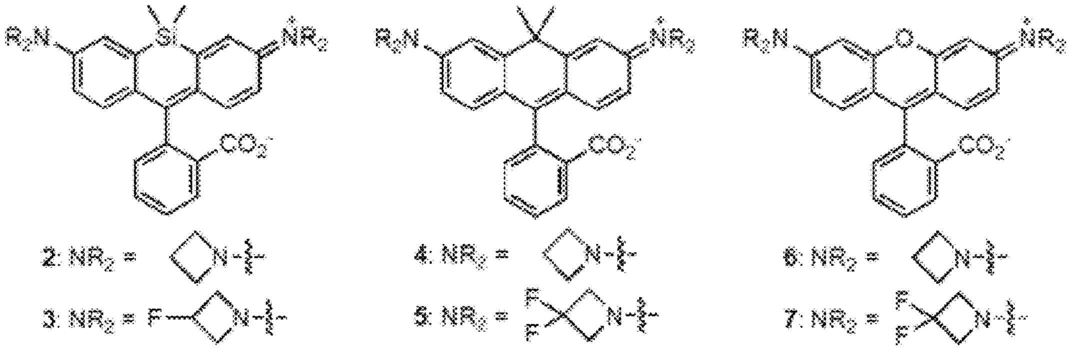

The mechanism of SiR/JF$_{646}$ fluorogenicity. In previous studies, the fluorogenicity of SiR was attributed to either the relatively small $K_{L-Z}$ values[18] or to the formation of weakly fluorescent aggregates.[14, 34] The key evidence for this latter mechanism was the large increase in absorption that occurred when the detergent sodium dodecyl sulfate (SDS) was added to aqueous solutions of SiR-based compounds, presumably disaggregating the dye. The present inventors investigated this effect and found it was detergent-specific; incubation of SiR (1) and JF$_{646}$ (2) with commonly used laboratory detergents showed absorbance increases only in the presence of SDS (FIG. 11A). The interaction between the Si-rhodamine dyes 1 and 2 and SDS was further characterized by measuring the absorption of 1 or 2 vs. [SDS] and observing the absorbance increase only above the critical micelle concentration (c.m.c.) of SDS (FIG. 1C). These results suggest another mechanism for this observed increase in absorption, where dyes 1 and 2 interact with the negatively charged micelle surface, thereby stabilizing the zwitterionic form and giving the increase in absorption. This is further supported by the bathochromic shift in absorption maxima ($\lambda_{max}$) observed for 1 and 2 in the presence of SDS (FIGS. 11B and 11C), which is characteristic for rhodamine-SDS-micelle complexes.[35]

Figure 1D:
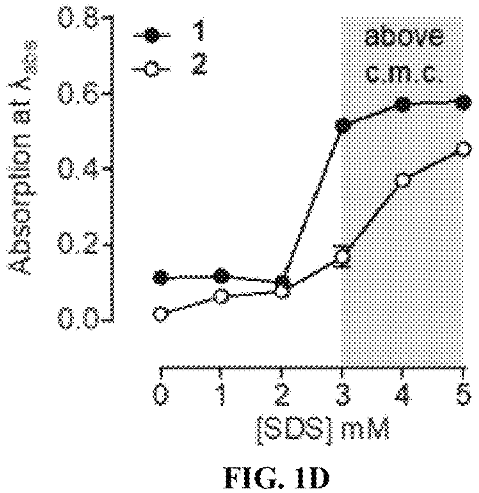

These data reveal a problem with the use of SDS solutions to determine spectral properties of fluorogenic dyes as the measurement is strongly concentration- and dye-dependent (FIG. 1D). Instead, a solution of strong acid in alcoholic solvents was used (e.g., TFA in 3,3,3-trifluoroethanol) to shift the equilibrium to the open form by protonation of the o-carboxyl group. This decades-old procedure[36] allows estimation of the maximal extinction coefficient ($\varepsilon_{max}$) and determination of $K_{L-Z}=(\varepsilon/\varepsilon_{max})/(1-\varepsilon/\varepsilon_{max})$.

Based on these results it was contemplated that the fluorogenicity of SiR and similar dyes was dependent primarily on $K_{L-Z}$. Aggregation of such compounds can still occur, particularly for high concentrations of dyes that strongly prefer the lipophilic lactone form, but this is a consequence of the low $K_{L-Z}$ and not the causal element behind the observed fluorogenicity. To test this premise, the relationship between $K_{L-Z}$ was examined for a series of fluorescent dyes (1-7, FIG. 1C, Table 1) and the increase in fluorescence of the corresponding HaloTag ligands upon conjugation to purified HaloTag proteins. ($1_{HTL}$-$7_{HTL}$, FIG. 1E, FIG. 11D).

TABLE 1

Properties of Various Dyes

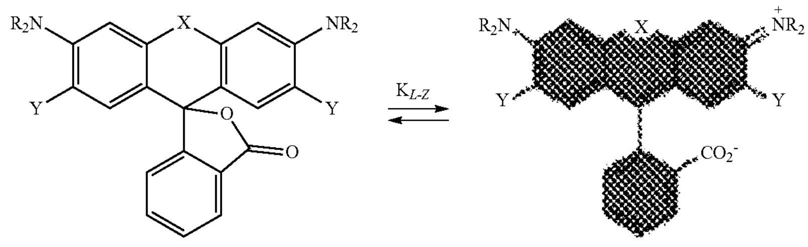

lactone (L) zwitterion (Z)

| dye | X | Y | $NR_2$ | $\lambda_{abs}$ (nm) | $\lambda_{em}$ (nm) | $\varepsilon_w$ ($M^{-1}cm^{-1}$) | $\varepsilon_{max}$ ($M^{-1}cm^{-1}$) | Φ | $K_{L-Z}$ |
|---|---|---|---|---|---|---|---|---|---|
| 1 | $Si(CH_3)_2$ | H | 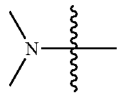 [SMILES: *N(C)C] | 643 | 662 | 28,200 | 141,000 | 0.41 | 0.0034 |

TABLE 1-continued

Properties of Various Dyes

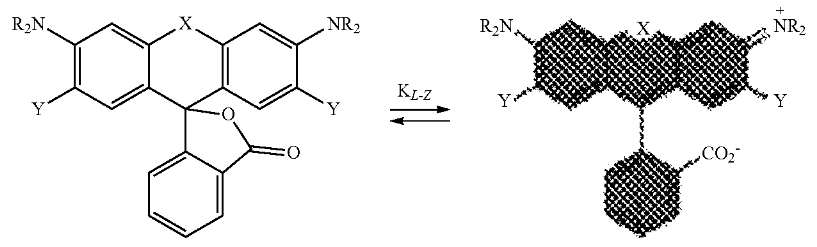

lactone (L) zwitterion (Z)

| dye | X | Y | $NR_2$ | $\lambda_{abs}$ (nm) | $\lambda_{em}$ (nm) | $\varepsilon_w$ ($M^{-1}cm^{-1}$) | $\varepsilon_{max}$ ($M^{-1}cm^{-1}$) | $\phi$ | $K_{L-Z}$ |
|---|---|---|---|---|---|---|---|---|---|
| 2 | $Si(CH_3)_2$ | H | 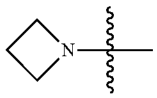 [SMILES: *N1CCC1] | 646 | 664 | 5,000 | 152,000 | 0.54 | 0.0012 |
| 3 | $Si(CH_3)_2$ | H | 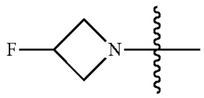 | 635 | 652 | ~400 | 167,000 | 0.56 | <0.0001 |
| 4 | $C(CH_3)_2$ | H | 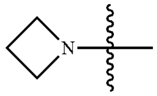 [SMILES: *N1CCC1] | 608 | 631 | 99,000 | 121,000 | 0.67 | 0.091 |
| 5 | $C(CH_3)_2$ | H | 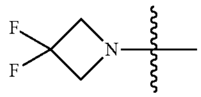 [SMILES: *N1CC(F)(F)C1] | 585 | 609 | 1,500 | 156,000 | 0.78 | <0.0001 |
| 6 | O | H | 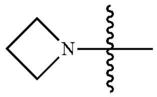 [SMILES: *N1CCC1] | 549 | 571 | 101,000 | 134,000 | 0.88 | 3.5 |
| 7 | O | H | 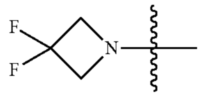 [SMILES: *N1CC(F)(F)C1] | 525 | 549 | 94,000 | 122,000 | 0.91 | 0.068 |
| 8 | $Si(CH_3)_2$ | H | 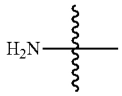 | 587 | 609 | 2,200 | 94,000 | 0.53 | 0.0043 |
| 9 | O | F | 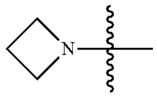 | 552 | 575 | 95,000 | 129,000 | 0.83 | 0.70 |
| 10 | O | F | 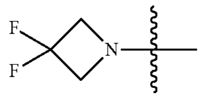 [SMILES: *N1CC(F)(F)C1] | 526 | 550 | 19,000 | 118,000 | 0.87 | 0.0050 |

Figure 1E:
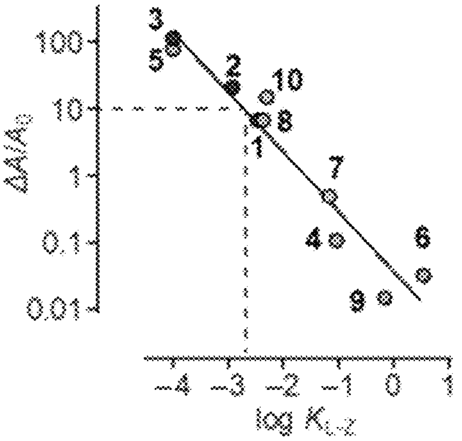

The $K_{L-Z}$ was determined using ε values measured in 1:1 dioxane:water to ensure a broad distribution of values.[18] An inverse relationship was observed between $K_{L-Z}$ and fluorogenicity, showing that $K_{L-Z}$ is sufficient to accurately predict the increase in fluorescence of rhodamine dyes. This increase in fluorescence is primarily driven by the increase in absorption; chromogenicity is correlated both with $K_{L-Z}$ and fluorogenicity (FIGS. 11E-11J). Importantly, this trend holds across different rhodamine scaffolds including Si-rhodamines (1-3), carborhodamines (4-5), and classic, oxygen-containing rhodamines (6-7, FIG. 1C). Based on this inverse relationship a simple rubric was determined: a dye with $K_{L-Z}<10^{-2}$ should yield a HaloTag ligand with at least 10-fold fluorogenicity (FIG. 1E).

Hydroxymethyl $JF_{646}$. Despite a large collection of Si-rhodamine dyes, however, all their spontaneously blinking variants are based on SiR. Owing to the limited color palette and the suboptimal blinking properties of HM-SiR, spontaneously blinking labels have not been extensively used in live-cell super-resolution imaging. Here, the collection of spontaneously blinking labels were expanded by developing a facile and general synthetic strategy for spontaneously blinking Si-rhodamines.

An efficient synthetic route to HM-$JF_{526}$ labels, a hydroxymethyl derivative of a classic rhodamine, was previously developed. A similar method was contemplated, using ditriflate-Si-fluoran XX as an intermediate could yield a divergent route to hydroxymethyl Si-rhodamine labels (FIG. 8). Pd-catalyzed cross-coupling has a broad substrate scope and would allow late-stage incorporation of different amino functionalities.

First, a hydroxymethyl derivative of $JF_{646}$ was prepared. (FIG. 8) Treatment of ditriflate-Si-fluoran XX with $LiBH_4$ at ambient temperature selectively reduced lactone to a cyclic ether XX leaving the 6-carboxy group intact, providing XX with high yield (78%). Formation of 6-t-butyl ester with acetal XX gave XX, allowing Pd-catalyzed cross-coupling with XX. The resulting 6-tert-butoxycarbonyl-HM-$JF_{646}$ (XX) can be deprotected to yield carboxylic acid XX and then converted to HaloTag ligand XX (HM-$JF_{646}$-HTL).

Figure 10A:
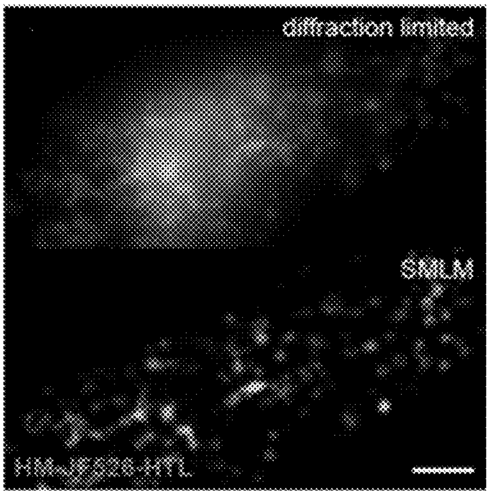
Figure 10B:
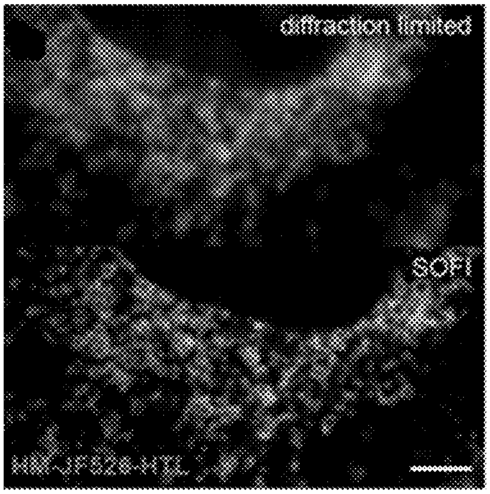
Figure 10C:
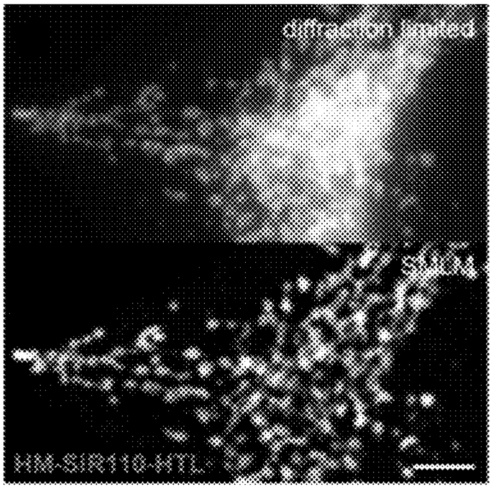
Figure 10D:
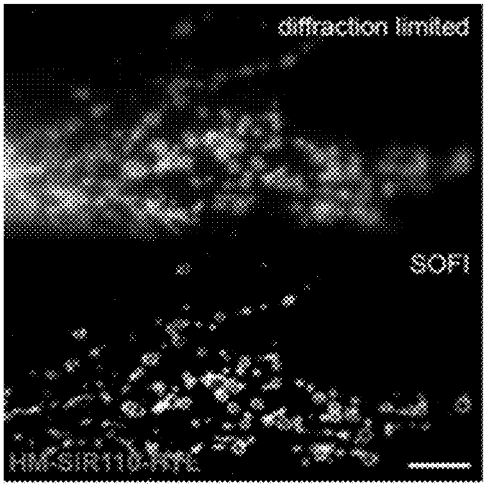
Figure 10E:
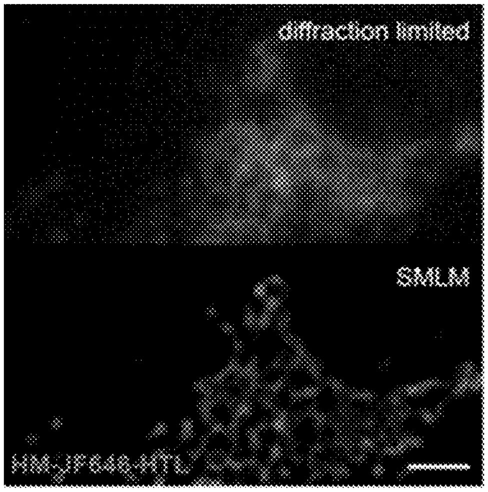
Figure 10F:
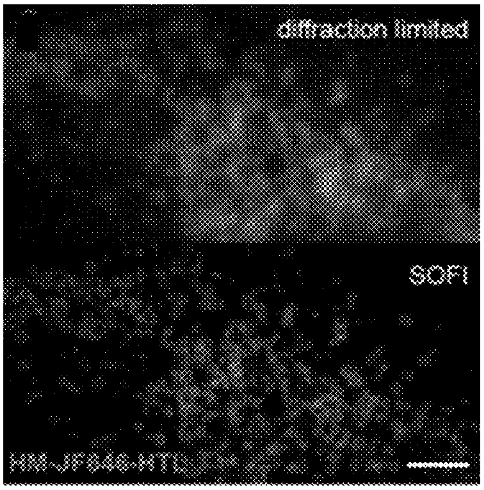

The utility of HM-$JF_{646}$-HaloTag ligand (XX) as a label for SMLM in fixed cells was then tested. Mitochondrial protein TOMM20 fused to the HaloTag protein was imaged and the HaloTag fusions were labeled with ligand XX (FIG. 10). As expected, the HM-$JF_{646}$-HaloTag conjugate spontaneously blinks in standard phosphate-buffered saline (pH 7.4) throughout the imaging session and did not require short-wavelength activation light. Standard SMLM analysis transformed these movies into super-resolution images (FIG. 10E). The HM-$JF_{646}$ ligand was then tested for super-resolution optical fluctuation imaging (SOFI) experiments. SOFI is a super-resolution imaging technique that analyzes the temporally fluctuating fluorescence signal with high order statistics to generate a super-resolution image, and the spontaneously-blinking HM-$JF_{646}$ generate fluctuating fluorescence signal useful for SOFI analysis. Standard second-order SOFI analysis reconstructed these movies into super-resolution images with improved resolution and reduced background fluorescence (FIG. 10F). The reduction of background is because the SOFI algorithm intrinsically removes the non-fluctuating background signal. HM-$JF_{646}$ ligand XX was further evaluated for SOFI experiments in living cells. Since SOFI experiments using HM-$JF_{646}$ labels only require illumination intensity at ~100 W/cm2, it reduces phototoxicity and photobleaching and allows time-lapse super-resolution imaging of mitochondria dynamics.

Si-Rhodamine 110. In previous work the present inventors developed strategies to fine-tune the properties of rhodamines by incorporating substituted azetidines into the dye structure.[18] In particular, the bright, fluorogenic carborhodamine $JF_{585}$ (5, FIG. 1C; $\lambda_{abs}/\lambda_{em}$=585 nm/609 nm, $\Phi$=0.78) was developed by replacing the azetidine rings in $JF_{608}$ (4; $\lambda_{abs}/\lambda_{em}$=608 nm/631 nm, $\Phi$=0.67) with 3,3-difluoroazetidine motifs; the $K_{L-Z}$ trend holds for these dyes (FIG. 1E). As an alternative strategy to create orange-emitting fluorogenic dyes, the Si-containing analog of rhodamine 110 (8) was investigated, which has been described as a scaffold for fluorogenic enzyme substrates in the patent literature,[37] but has not been used as a fluorescent label in cellular experiments. This compound was synthesized using the Pd-catalyzed cross-coupling of the Si-fluorescein bistriflate (11) with t-butyl carbamate followed by deprotection with TFA (FIG. 2A).[15, 38] Compound 8 exhibited $\lambda_{max}/\lambda_{em}$=587 nm/609 nm, representing a ~50 nm hypsochromic shift relative to SiR (1; Labs/$\lambda_{em}$=643 nm/662 nm, Table 1); this dye was named Si-rhodamine 110 ($SiR_{110}$). It has an increased fluorescence quantum yield ($\Phi$=0.53) compared to SiR ($\Phi$=0.41, Table 1), but a comparable $K_{L-Z}$=0.0043.

Based on the $K_{L-Z}$ vs. fluorogenicity relationship (FIG. 1E), it was predicted that ligands based on 8 would be fluorogenic. This was an interesting test since $SiR_{110}$ has similar $K_{L-Z}$ values to SiR but a different structure—lacking the four hydrophobic $CH_3$ groups in 1. To test this hypothesis, the $SiR_{110}$-HaloTag ligand ($8_{HTL}$, FIG. 2B) was prepared starting from the 6-carboxy-Si-fluorescein bistriflate methyl ester (13).[39] Cross-coupling afforded the Boc-protected $SiRh_{110}$ 14, which was saponified to yield free acid 15. Formation of the N-hydroxysuccinimidyl ester in situ, amidation with the HaloTag ligand (16) and deprotection with TFA yielded $8_{HTL}$. A X-fold increase in fluorescence was observed after conjugation of $8_{HTL}$ to HaloTag protein (FIG. 2C), similar to SiR-HaloTag ligand ($1_{HTL}$; $\Delta F/F_0$=XX) and in line with the $K_{L-Z}$ trend (FIG. 1E). This dye was an excellent label for live-cell imaging experiments (FIG. 2D) and showed higher photostability than the previously described orange fluorogenic $JF_{585}$-HaloTag ligand ($5_{HTL}$, FIG. 2E). These results further support the hypothesis that $K_{L-Z}$ is the primary driver for rhodamine fluorogenicity.

Hydroxymethyl $SiR_{110}$. Expansion of the color pellet of spontaneously blinking labels was contemplated. Since $SiR_{110}$ exhibits a similar open-closed equilibrium to SiR and a 50 nm hypsochromic shift of spectrum, it was reasoned that creating a hydroxymethyl derivative of $SiR_{110}$ could yield spectrally distinct spontaneously blinking labels useful for multicolor super-resolution imaging. Cross-coupling of the cyclic ether XX afforded the Boc-protected hydroxymethyl $SiR_{110}$ XX, which was deprotected with TFA to yield free acid XX. Formation of the N-hydroxysuccinimidyl ester in situ and amidation with the HaloTag ligand (XX) yielded HaloTag ligand XX (HM-$SiR_{110}$-HTL). XX was an excellent spontaneously blinking label for facile super-resolution imaging including SMLM and SOFI (FIGS. 10C and 10D). Its high photostability allows super-resolution imaging of mitochondria dynamics at a temporal resolution of 7.5 sec for 5 min without significant photobleaching.

Janelia Fluor 552. The standard, oxygen-containing rhodamine scaffold exemplified by $JF_{549}$ (6, FIG. 1C; $\lambda_{abs}/\lambda_{em}$=549 nm/571 nm, $\Phi$=0.88) was considered next. Creating a fluorogenic rhodamine is challenging since this class strongly prefer the fluorescent zwitterionic form; $JF_{549}$ exhibits a high $K_{L-Z}$=3.5, which is >$10^2$-fold higher than the apparent $K_{L-Z}$ threshold for a fluorogenic ligand (FIG. 1E). Incorporation of 3,3-difluoroazetidine motifs into the $JF_{549}$ structure yields $JF_{525}$ (7), which shows a lower $K_{L-Z}$=0.068 and elicits ~25 nm hypsochromic shift with similar brightness ($\lambda_{max}/\lambda_{em}$=525 nm/549 nm, $\Phi$=0.91; Table 1). This $K_{L-Z}$ tuning is insufficient to achieve fluorogenicity although the $JF_{525}$-HaloTag ligand ($7_{HTL}$) is highly cell- and tissue-permeant.[18, 40] Since the available substitutions on the azetidine ring were exhausted with $JF_{525}$, a complementary approach was considered for further modulating $K_{L-Z}$. A $JF_{549}$ analog was recently reported with fluorine atoms installed at the 2' and 7' positions on the xanthene ring. This modification reduced the $K_{L-Z}$ by 5-fold ($K_{L-Z}$=0.70) with only a minor shift in spectral properties ($\lambda_{abs}/\lambda_{em}$=552 nm/575 nm, $\Phi$=0.83; Table 1).[41] The resulting dye, Janelia Fluor 552 ($JF_{552}$; 9), is of particular interest because it could show improved cell-permeability relative to $JF_{549}$ and could be further modified to create a fluorogenic rhodamine.

A general synthetic strategy was developed for $JF_{552}$ derivatives that would also allow late-stage incorporation of different azetidine functionality. Unfortunately, the standard Pd-catalyzed cross-coupling approach[38] gave low yield (<5%) when starting with 2',7'-difluorofluorescein bistriflate due to the instability of the o-fluorophenyl triflate groups (data not shown). To circumvent this problem, a concise and versatile synthesis was devised starting with 3-bromo-4-fluorophenol (17, Scheme 1a).[42] Acid-mediated condensation of 17 and phthalic anhydride (18) yielded dibromofluoran 19. Pd-catalyzed cross-coupling with azetidine (20) provided $JF_{552}$ (9). To introduce a carboxyl group for bioconjugation, phenol 17 was condensed with trimellitic anhydride (21) to give an isomeric mixture; crystallization from 9:1 toluene: pyridine yielded the 6-carboxy isomer 22. This was protected as the t-butyl ester using N,N-dimethylformamide di-t-butyl acetal (23) to yield 24 followed by Pd-catalyzed cross-coupling with azetidine (18) to provide 6-carboxy-$JF_{552}$ t-butyl ester (25). Deprotection of 25 with TFA yielded carboxylic acid 26 and subsequent conjugation to the HaloTag ligand amine (16) gave $JF_{552}$-HaloTag ligand $9_{HTL}$ (Scheme 1a). Based on this synthesis, an attempt was made to transform 2',7'-difluorofluorescein bistriflates to their respective dibromofluorans using Ru catalysts.[43] This reaction was successful for the synthesis of dibromide 19 but gave poor yields of t-butyl ester 24 (data not shown).

$JF_{552}$ ligands were evaluated as cell-permeable fluorescent labels, comparing $JF_{552}$-Halo Tag ligand ($9_{HTL}$) to $JF_{549}$-HaloTag ligand ($6_{HTL}$, FIG. 11D) in yeast expressing histone-H2A.Z-HaloTag protein fusion. Although $6_{HTL}$ showed relatively poor labeling (FIG. 3A), the $9_{HTL}$ molecule showed high fluorescence signal from the labeled yeast nuclei under the same imaging conditions (FIG. 3B). This result is expected based on the smaller $K_{L-Z}$ of $JF_{552}$, which should improve cell permeability. The trimethoprim (TMP) conjugates of $JF_{549}$ and $JF_{552}$ ($6_{TMP}$ and $9_{TMP}$) were also synthesized by reacting the 6-carboxy derivatives of these dyes (26 and 27, respectively) with the amino-TMP 28 (Scheme 1c). TMP conjugates selectively bind to *E. coli* dihydrofolate reductase (eDHFR) and this labeling strategy can be used for live-cell imaging.[44] Hhistone-H2B-eDHFR fusions were expressed in U2OS cells and labeled with $6_{TMP}$ or $9_{TMP}$. Nuclei labeled with $JF_{552}$-based $9_{TMP}$ were 8-fold brighter than cells labeled with $6_{TMP}$, giving images with higher signal-to-background (FIGS. 3C and 3D). These results support the hypothesis that even modest decreases in $K_{L-Z}$ can improve cell permeability across different cell-types and labeling strategies.

Scheme 1. Syntheses of $JF_{552}$ derivatives a

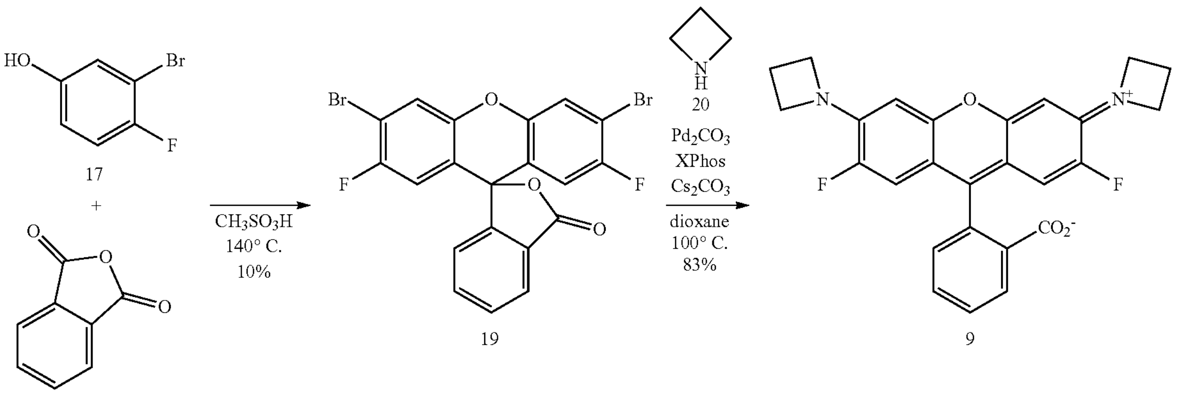

17 18 19 9 b

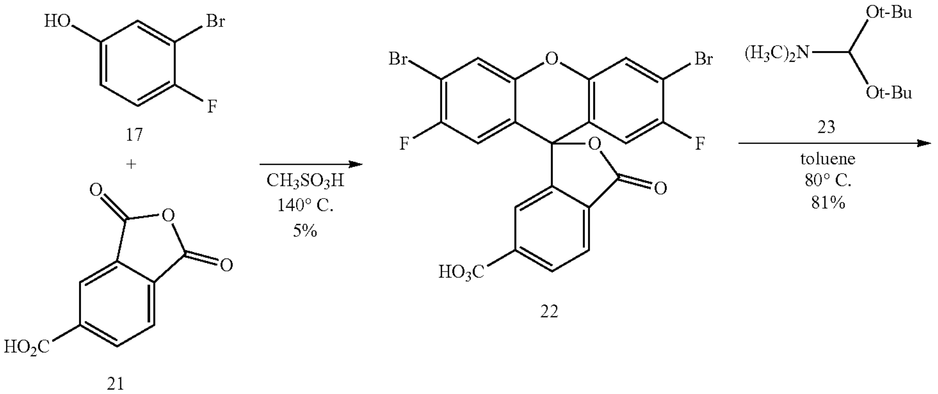

17 21 22

-continued
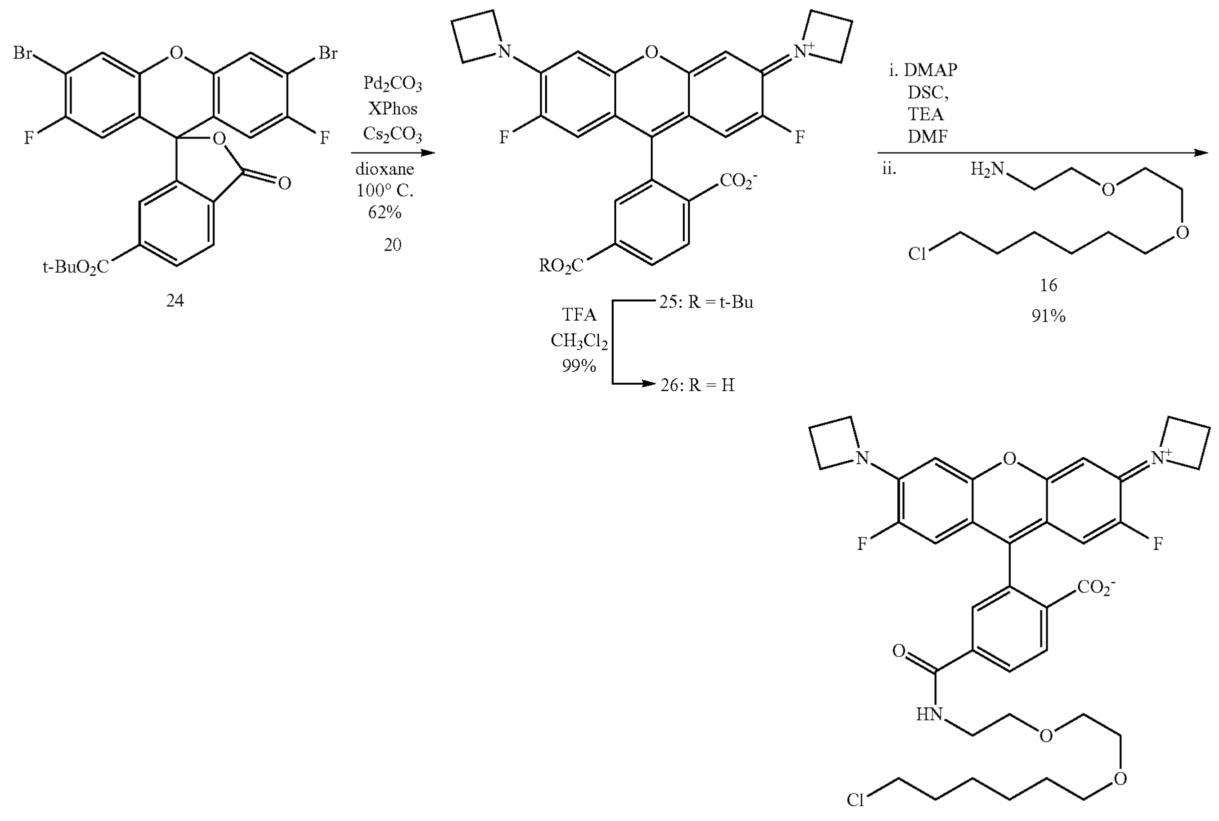
$9_{HTL}$
c
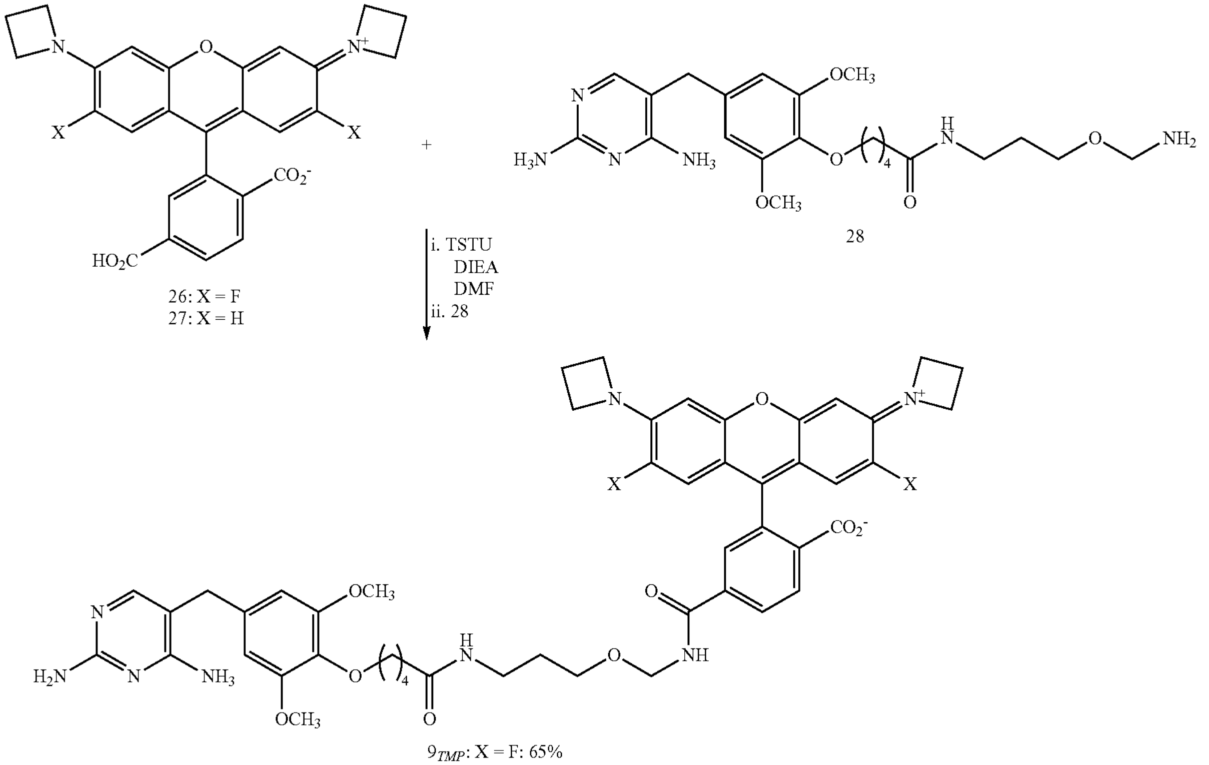
$9_{TMP}$: X = F: 65%
$6_{TMP}$: X = H: 44%

Janelia Fluor 526. The structural modifications of 7 ($K_{L-Z}$=0.068) and 9 ($K_{L-Z}$=0.70) were combined, positing that the two complementary alterations could additively shift the $K_{L-Z}<10^{-2}$, thus yielding a fluorogenic molecule. To prepare the free dyes Pd-catalyzed cross-coupling was used to attach 3,3-difluoroazetidine (29) to dibromide 19 yielding the hexafluorinated rhodamine 10 (FIG. 4A). The resulting compound was named Janelia Fluor 526 ($JF_{526}$, $\lambda_{abs}/\lambda_{em}$=526 nm/550 nm, $\Phi$=0.87), which exhibited the desired additive effect on the lactone-zwitterion equilibrium ($K_{L-Z}$=0.0050; Table 1). Next, the 6-carboxy derivative was synthesized using a route akin to $JF_{552}$ ligands (Scheme 1b)—cross-coupling of dibromide 24 with azetidine 29 to give t-butyl ester 30 followed by deprotection with TFA to give 31. This could be coupled to a variety of amine-containing ligand moieties to yield new labels including the $JF_{526}$-HaloTag ligand ($7_{HTL}$) and $JF_{526}$-SNAP-tag ligand ($7_{STL}$, FIG. 4C). This was compared with the previously reported $JF_{525}$-HaloTag ligand[18] ($7_{HTL}$) in vitro and in live cells. Although $7_{HTL}$ exhibited an increase of absorbance upon conjugation to purified HaloTag protein, $10_{HTL}$ (Scheme 2a) exhibited a substantial increase, again following the $K_{L-Z}$-fluorogenicity trend (FIG. 1E). $JF_{526}$ showed superior signal-to-background compared to $JF_{525}$ in no-wash, live-cell imaging experiments using either the HaloTag (FIGS. 4D and 4E) or SNAP-tag expressed as histone-H2B fusion proteins (10 STL VS. 7 $_{STL}$, FIGS. 4F and 4G).

Other $JF_{526}$ ligands were then prepared to demonstrate the general utility of this dye for multicolor advanced microscopy.[27] The following conjugates were synthesized: $JF_{526}$-Hoechst ($10_{HST}$, Scheme 2b) to stain DNA, $JF_{526}$-Taxol ($10_{TXL}$, Scheme 2c) to image microtubules, and $JF_{526}$-pepstatin A ($10_{PEP}$, Scheme 2d) to visualize lysosomes (FIG. 4B, FIG. 5A). Live-cell imaging with these compounds showed specific staining, enabling one-, two- and three-color 'no-wash' imaging experiments (FIG. 5B-5D). In particular, the $JF_{526}$-Taxol ($10_{TXL}$) showed comparable performance to 'SiR-tubulin' ($1_{TXL}$).[27] $JF_{526}$ ligands were then used in advanced microscopy. Two-color 3D-SIM[45] was performed in live cells using $JF_{526}$-pepstatin A ($10_{PEP}$) and $JF_{646}$-Hoechst[46] ($2_{HST}$, FIG. 6A). $JF_{526}$ also enabled multicolor super-resolution STED microscopy[47] of microtubules using $10_{TXL}$ depleted with 775 nm (FIG. 6B). Notably, the compatibility of $JF_{526}$ with the standard 775 nm depletion line facilitated three-color live-cell STED imaging using $JF_{526}$-Taxol ($10_{TXL}$, microtubules), $JF_{585}$-HaloTag ligand ($5_{HTL}$) targeted to Sec61β (endoplasmic reticulum), and $JF_{646}$-SNAP-tag ($2_{STL}$) ligand targeted to TOMM20 (mitochondria, FIG. 6C). Finally, the $JF_{526}$-pepstatin A ($10_{PEP}$) could be used for live-cell, two-color lattice light-sheet microscopy with $2_{HST}$ (FIG. 6D).[48]

Hydroxymethyl $JF_{526}$. The lactone-zwitterion equilibrium of rhodamine dyes can be further exploited for single-molecule localization microscopy (SMLM). Replacing the carboxyl moiety in SiR with the more nucleophilic hydroxymethyl group elicits an additional shift to the closed form.[49-50] The resulting hydroxymethyl-SiR (HM-SiR, 32) exists primarily in a colorless, non-fluorescent form but spontaneously switches to a transient, fluorescent form at physiological pH (FIG. 7A). This blinking behavior enables facile SMLM imaging, bypassing the need for photoconvertible fluorescent proteins, photoactivatable dyes, or strongly reducing dSTORM buffers.[49, 51]

Given the similarity of the $K_{L-Z}$ values for $JF_{526}$ and SiR it was contemplated that a hydroxymethyl derivative of $JF_{526}$ would show similar utility to 32 in SMLM. A concise, high-yielding approach was devised to synthesize derivatives of hydroxymethyl $JF_{526}$ (HM-$JF_{526}$), leveraging the divergent synthesis of $JF_{526}$ and the differential reactivity of carboxyl groups and lactones with borohydride reductants (FIG. 7B). Deprotection of 24 with TFA yielded 33. Treatment of 33 with $LiBH_4$ at ambient temperature selectively reduced the lactone to a cyclic ether leaving the 6-carboxy group intact, providing 34 in moderate yield (54%). This was reprotected as 6-t-butyl ester with acetal 22 to give 35 (63%), which underwent Pd-catalyzed cross-coupling with 29 (74%). The resulting 6-tert-butoxycarbonyl-HM-$JF_{526}$ (36) can be deprotected to yield carboxylic acid 37 and then converted to amine-reactive N-hydroxysuccinimidyl ester 38 (HM-$JF_{526}$ NHS).

Figure 7H:
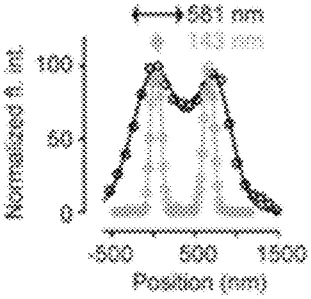

To evaluate the performance of HM-$JF_{526}$ in SMLM experiments 38 was used to label a goat-anti-mouse secondary antibody, followed by immunostaining of an anti-β-tubulin primary antibody in fixed cells. SMLM imaging in standard PBS buffer revealed that the HM-$JF_{526}$ label showed spontaneous blinking behavior throughout the imaging session and did not require short-wavelength activation light. Using standard SMLM analysis transformed movies from the imaging sessions into super-resolution images (FIGS. 7C and 7D); the HM-$JF_{526}$ label yielded 571 photons on average with a localization accuracy (σ) of 25 nm. The SMLM images showed fine structures of microtubules with a full-width at half-maximum (FWHM) of 86 nm; diffraction-limited images had an FWHM of 253 nm (FIG. 7E). Mitochondria was also labeled using an anti-TOMM20 primary antibody which gave SMLM images of mitochondria with improved resolution (FWHM=143 nm) compared to diffraction-limited images (FWHM=581 nm; FIG. 7F-7H). Thus, HM-$JF_{526}$ constitutes a new label for SMLM that is spectrally distinct from HM-SiR and compatible with standard immunolabeling protocols.

Scheme 2: Synthesis of $JF_{526}$ Derivatives a

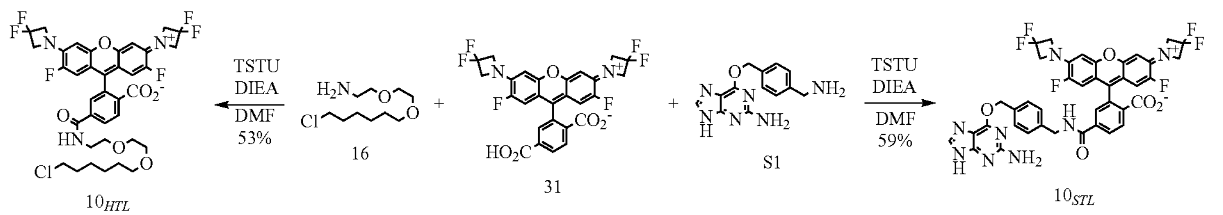

$10_{HTL}$ 16 31 S1 $10_{STL}$

-continued
b
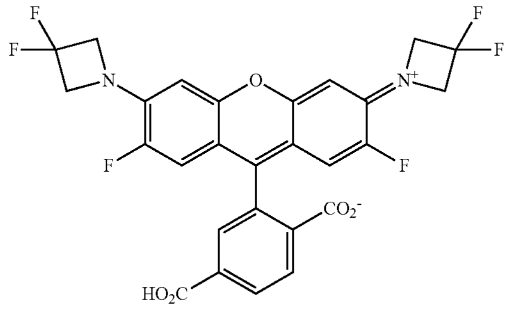
31
+
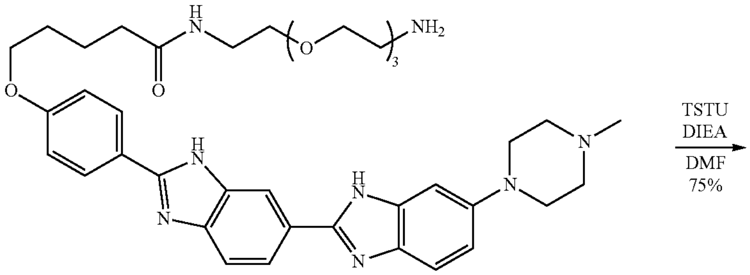
S2
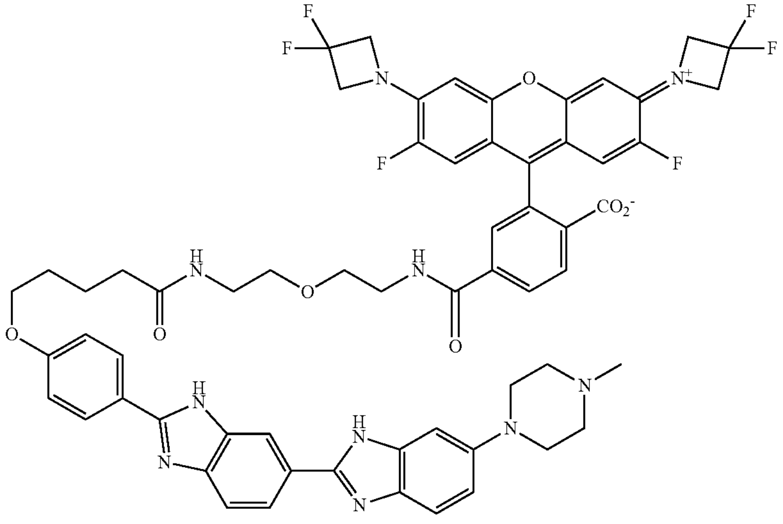
$10_{HST}$
c
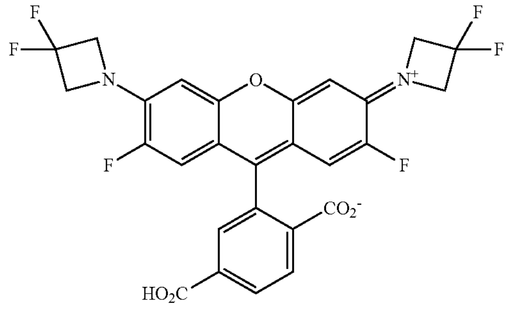
31
+
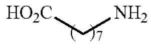
S3
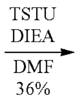

-continued
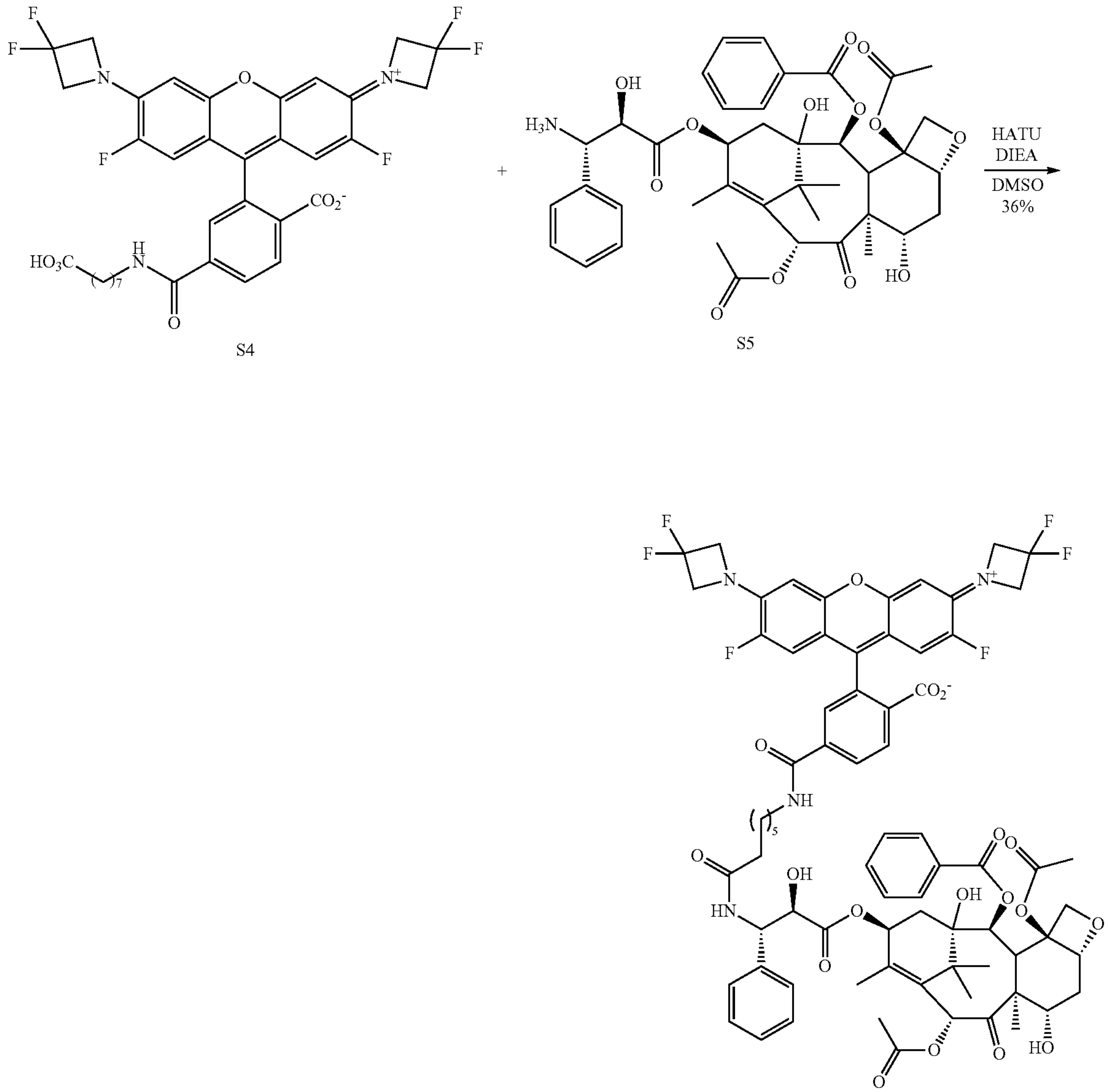
S4
S5
$10_{TXL}$
d
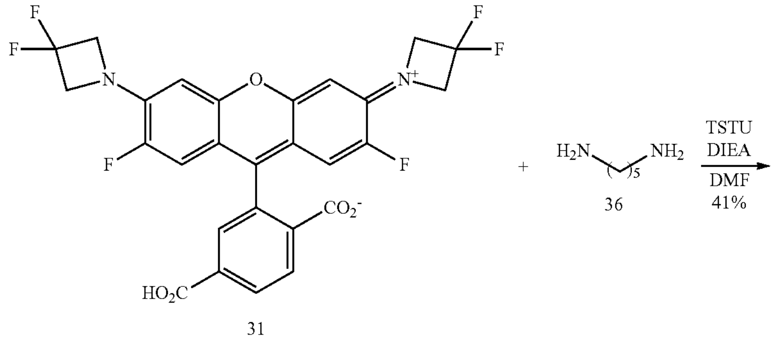
31
36

-continued
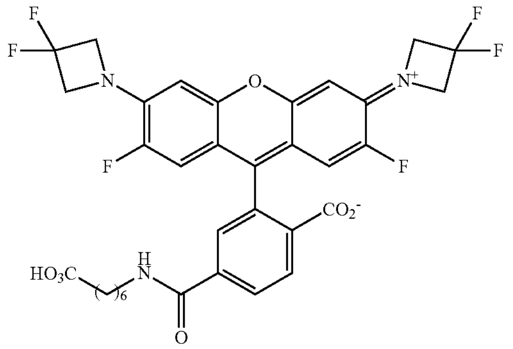
S7
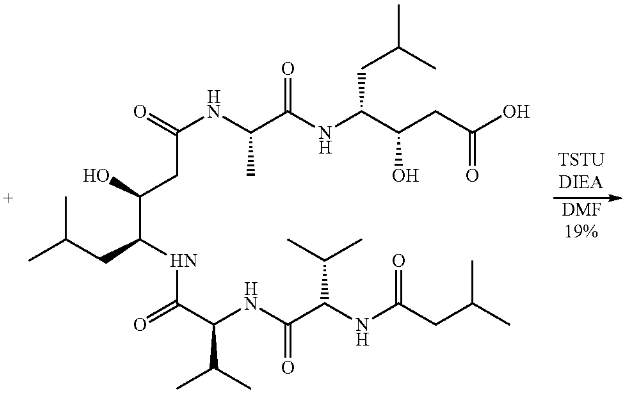
38
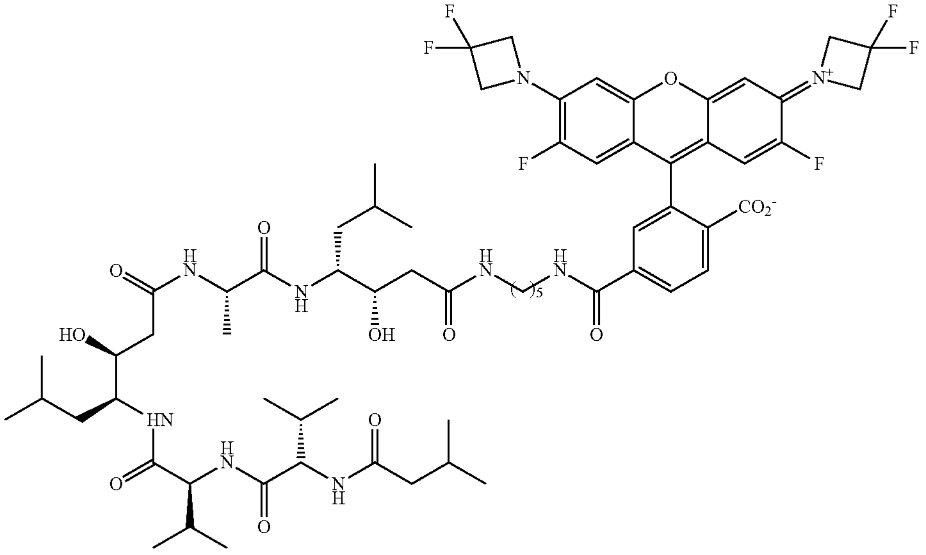
$10_{PEP}$
e
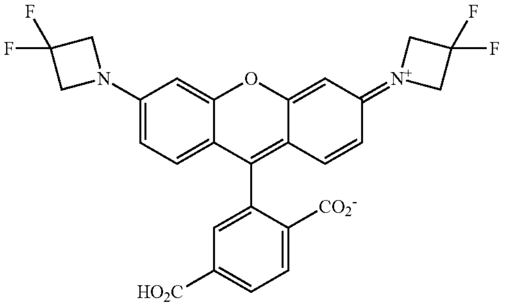
S9
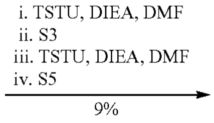

-continued

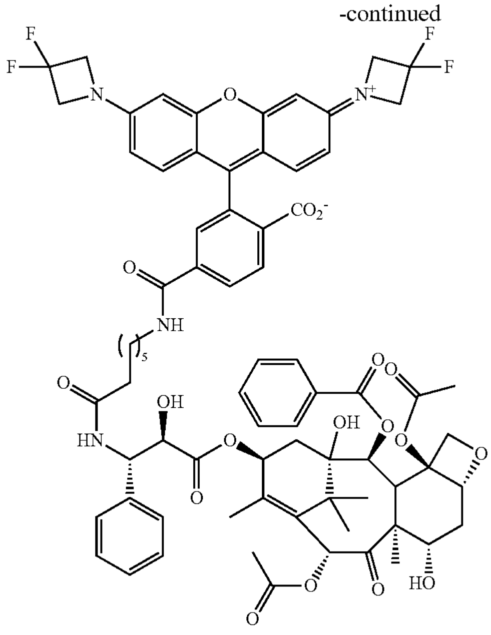

$7_{TXL}$

General Synthetic Methods. Commercial reagents were obtained from reputable suppliers and used as received. All solvents were purchased in septum-sealed bottles stored under an inert atmosphere. All reactions were sealed with septa through which a nitrogen atmosphere was introduced unless otherwise noted. Reactions were conducted in round-bottomed flasks or septum-capped crimp-top vials containing Teflon-coated magnetic stir bars. Heating of reactions was accomplished using an aluminum reaction block on top of a stirring hotplate equipped with an electronic contact thermometer to maintain the indicated temperatures unless otherwise indicated.

Reactions were monitored by thin layer chromatography (TLC) on precoated TLC glass plates (silica gel 60 F254, 250 μm thickness) or by tandem high pressure liquid chromatography mass spectrometry (Shimadzu 2020 LC-MS system; Phenomenex Kinetex 2.1 mm×30 mm 2.6 μm C18 column; 5 μL injection; 5-98% MeCN/H2O, linear gradient, with constant 0.1% v/v HCO2H additive; 6 min run; 0.5 mL/min flow; ESI; positive ion mode). TLC chromatograms were visualized by UV illumination or developed with p-anisaldehyde, ceric ammonium molybdate, or KMnO4 stain. Reaction products were purified by flash chromatography on an automated purification system using pre-packed silica gel columns or by preparative HPLC(Phenomenex Gemini-NX 30×150 mm 5 μm C18 column). Analytical LC-MS analysis was performed on an Agilent 1200 LC-MS system equipped with an autosampler, diode array detector, and mass spectrometry detector using an Agilent Eclipse XDB 4.6×150 mm 5 μm C18 column under the indicated conditions with the retention time indicated as tR. The mass spectrograms for 7TXL and 10TXL were taken from experiments using LC-MS Shimadzu system.

Previous attempts to tune the $K_{L-Z}$ of standard rhodamine dyes using 3,3-difluoroazetidine substituents transformed $JF_{549}$ (6, $K_{L-Z}$=3.5) to the highly bioavailable $JF_{525}$ (7, $K_{L-Z}$=0.068). Nevertheless, this decrease in $K_{L-Z}$ was insufficient to meet the fluorogenic threshold of $K_{L-Z}<10^{-2}$; ligands based on $JF_{525}$ show low degrees of fluorogenicity.

A complementary approach was used to further tune the $K_{L-Z}$ by fluorinating the xanthene system. This yielded the highly cell-permeant $JF_{552}$ (9) as an intermediary product (Scheme 1) and ultimately led to the fluorogenic rhodamine $JF_{526}$ (10). Akin to SiR (1), $JF_{526}$ is a versatile scaffold for fluorogenic ligands, including labels for genetically encoded self-labeling protein tags and stains for endogenous structures. These green-emitting ligands can be used in concert with red- and orange-emitting fluorogenic dyes,[14-15, 18] allowing multicolor SIM and STED imaging in live cells (FIGS. 6A-6D). The utility of $JF_{526}$ was further extended to SMLM by creating the spontaneously blinking derivative: HM-$JF_{526}$ (FIG. 7A).

NMR spectra were recorded on a 400 MHz spectrometer. $^1$H and $^{13}$C chemical shifts were referenced to TMS or residual solvent peaks, and $^{19}$F chemical shifts were referenced to CFCl3. Data for $^1$H NMR spectra are reported as follows: chemical shift (ö ppm), multiplicity (s=singlet, d=doublet, t=triplet, q=quartet, dd=doublet of doublets, m=multiplet, etc.), coupling constant (Hz), integration. Data for $^{13}$C NMR spectra are reported by chemical shift (ö ppm) with hydrogen multiplicity (C, CH, $CH_2$, $CH_3$) information obtained from DEPT spectra. Data for $^{19}$F NMR spectra are reported as follows: chemical shift (ö ppm), multiplicity, coupling constant (Hz).

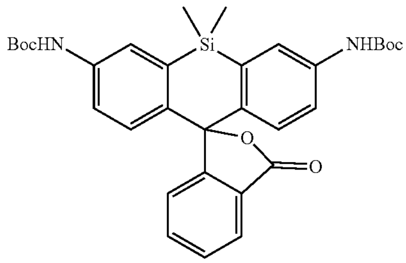 [SMILES: CC(C)(C)OC(=O)Nc1ccc2c(c1)[Si](C)(C)c1cc(NC(=O)OC(C)(C)C)ccc1C21OC(=O)c2ccccc21]

Boc2SiR110 (12): A vial was charged with Si-fluorescein ditriflate[15] (Tf2SiFl, 11, 90 mg, 141 μmol), tert-butyl carbamate (36 mg, 310 μmol, 2.2 eq), Pd2dba3 (12.9 mg, 14.1 μmol, 0.1 eq), Xantphos (24.5 mg, 42.3 μmol, 0.3 eq), and Cs2CO3 (129 mg, 395 μmol, 2.8 eq). The vial was sealed and evacuated/backfilled with nitrogen (3×). Dioxane (1 mL) was added, and the reaction was flushed again with nitrogen (3×). The reaction was stirred at 100° C. for 18 h. It was then cooled to room temperature, filtered through Celite with $CH_2Cl2$, and concentrated under reduced pressure. The residue was purified by silica gel chromatography (0-30% EtOAc/hexanes, linear gradient) to afford 12 (62 mg, 77%) as a colorless solid. $^{1}H$ NMR (CDCl3, 400 MHZ) ö 7.99-7.93 (m, 1H), 7.71 (d, J=2.2 Hz, 2H), 7.61 (td, J=7.5, 1.1 Hz, 1H), 7.52 (td, J=7.5, 0.8 Hz, 1H), 7.23-7.15 (m, 3H), 6.95 (d, J=8.7 Hz, 2H), 6.59 (s, 2H), 1.50 (s, 18H), 0.65 (s, 3H), 0.59 (s, 3H); $^{13}C$ NMR (CDCl3, 101 MHZ) δ 170.7 (C), 154.5 (C), 152.7 (C), 138.7 (C), 138.1 (C), 136.6 (C), 134.3 (CH), 129.2 (CH), 127.8 (CH), 126.2 (CH), 125.8 (C), 124.2 (CH), 123.2 (CH), 119.9 (CH), 90.2 (C), 80.9 (C), 28.5 (CH3), 0.2 (CH3), −0.1 (CH3); HRMS (ESI) calcd for C32H37N2O6Si $[M+H^+$ 573.2415, found 573.2411.

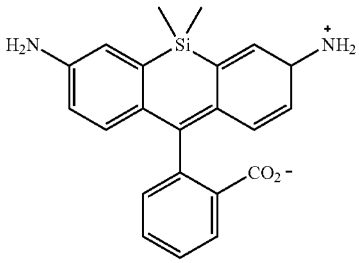

Si-Rhodamine 110 (SiR110, 8): Boc2SiR110 (12, 52 mg, 90.8 μmol) was taken up in $CH_2Cl2$ (2.5 mL), and trifluoroacetic acid (0.5 mL) was added. The reaction was stirred at room temperature for 2 h. Toluene (3 mL) was added, and the reaction mixture was concentrated under reduced pressure. The residue was dissolved in EtOAc and washed with saturated NaHCO3(aq) and brine. The organic layer was deposited onto silica gel and concentrated under reduced pressure. Flash chromatography (0-10% MeOH with 2 M NH3/CH2Cl2, linear gradient; dry load with silica gel) afforded 31 mg (92%) of 8 as a blue solid. $^{1}H$ NMR (DMSO-d6, 400 MHz) δ 7.95-7.88 (m, 1H), 7.79 (td, J=7.5, 1.1 Hz, 1H), 7.64 (td, J=7.6, 0.8 Hz, 1H), 7.35-7.28 (m, 1H), 6.93-6.87 (m, 2H), 6.50-6.39 (m, 4H), 5.28 (s, 4H), 0.52 (s, 3H), 0.45 (s, 3H); $^{13}C$ NMR (DMSO-d6, 101 MHZ) δ 169.7 (C), 153.9 (C), 148.0 (C), 136.1 (C), 134.4 (CH), 130.9 (C), 129.1 (CH), 127.6 (CH), 125.9 (C), 125.1 (CH), 124.6 (CH), 118.3 (CH), 114.8 (CH), 91.6 (C), 0.2 (CH3), −1.8 (CH3); Analytical LC-MS: tR=8.7 min, >99% purity (10-95% MeCN/H2O, linear gradient, with constant 0.1% v/v TFA additive; 20 min run; 1 mL/min flow; ESI; positive ion mode; UV detection at 254 nm); HRMS (ESI) calcd for C22H21N2O2Si $[M+H]^+$ 373.1367, found 373.1362.

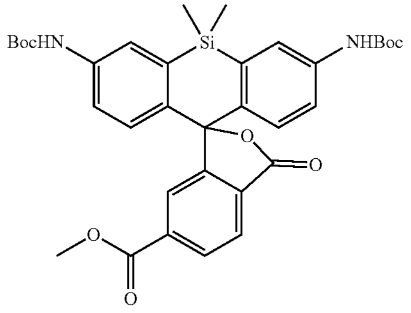 [SMILES: COC(=O)c1ccc2c(c1)C1(OC2=O)c2ccc(NC(=O)OC(C)(C)C)cc2[Si](C)(C)c2cc(NC(=O)OC(C)(C)C)ccc21]

6-Methoxycarbonyl-Boc2SiR110 (14): A vial was charged with 6-methoxycarbonyl-Si-fluorescein ditriflate 11 (Tf2SiFl-6-CO2Me, 13, 820 mg, 1.18 mmol), tert-butyl carbamate (331 mg, 2.83 mmol, 2.4 eq), Pd2dba3 (108 mg, 0.118 mmol, 0.1 eq), Xantphos (204 mg, 0.353 mmol, 0.3 eq), and Cs2CO3 (1.07 g, 3.30 mmol, 2.8 eq). The vial was sealed and evacuated/backfilled with nitrogen (3×). Dioxane (6 mL) was added, and the reaction vessel was flushed again with nitrogen (3×). The reaction was stirred at 100° C. for 3 h. It was then cooled to room temperature, filtered through Celite with CH2Cl2, and concentrated under reduced pressure. The residue was purified by silica gel chromatography (0-60% EtOAc/hexanes, linear gradient) to afford 14 (573 mg, 77%) as an off-white foam. $^{1}H$ NMR (CDCl3, 400 MHz) δ 8.17 (dd, J=8.0, 1.2 Hz, 1H), 8.01 (dd, J=8.0, 0.8 Hz, 1H), 7.87 (t, J=1.0 Hz, 1H), 7.73 (d, J=2.0 Hz, 2H), 7.20 (dd, J=8.7, 2.3 Hz, 2H), 6.98 (d, J=8.7 Hz, 2H), 6.51 (s, 2H), 3.88 (s, 3H), 1.51 (s, 18H), 0.72 (s, 3H), 0.61 (s, 3H); $^{13}C$ NMR (CDCl3, 101 MHZ) δ 169.9 (C), 165.7 (C), 155.1 (C), 152.7 (C), 138.3 (C), 138.2 (C), 136.2 (C), 135.6 (C), 130.4 (CH), 128.7 (C), 127.4 (CH), 126.2 (CH), 125.2 (CH), 123.4 (CH), 120.1 (CH), 90.2 (C), 81.0 (C), 52.8 (CH3), 28.5 (CH3), 0.1 (CH3), −0.8 (CH3); HRMS (ESI) calcd for C34H39N2O8Si $[M+H]^+$ 631.2470, found 631.2480.

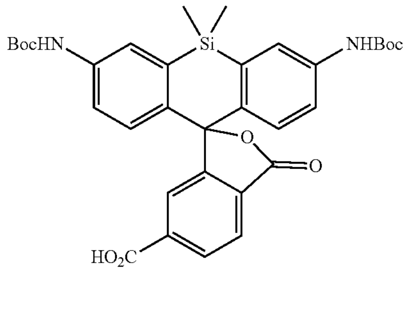 [SMILES: CC(C)(C)OC(=O)Nc1ccc2c(c1)[Si](C)(C)c1cc(NC(=O)OC(C)(C)C)ccc1C21OC(=O)c2ccc(C(=O)O)cc21]

6-Carboxy-Boc2SiR110 (15): To a solution of 14 (560 mg, 0.888 mmol) in 1:1 MeOH/THF (8 mL) was added 1 M NaOH (1.78 mL, 1.78 mmol, 2 eq). The reaction was stirred at room temperature for 18 h. It was subsequently acidified with 1 M HCl (3 mL), diluted with water, and extracted with EtOAc (2×). The combined organic extracts were washed with brine, dried over anhydrous MgSO4, filtered, and concentrated under reduced pressure to provide the carboxylic acid as a white solid (526 mg, 96%). $^{1}H$ NMR (DMSO-d6, 400 MHZ) δ 13.56 (s, 1H), 9.46 (s, 2H1), 8.13 (dd, J=8.0, 1.3 Hz, 1H), 8.07 (dd, J=7.9, 0.6 Hz, 1H), 7.91 (d, J=2.5 Hz, 2H), 7.71-7.65 (m, 1H), 7.38 (dd, J=8.8, 2.4 Hz, 2H), 6.90 (d, J=8.8 Hz, 2H), 1.46 (s, 18H), 0.63 (s, 3H), 0.52 (s, 3H); $^{13}C$ NMR (DMSO-d6, 101 MHZ) δ 169.1 (C), 165.9 (C), 154.7 (C), 152.7 (C), 139.3 (C), 136.9 (C), 136.8 (C), 134.7 (C), 130.3 (CH), 127.2 (C), 126.7 (CH), 126.3 (CH), 123.9 (CH), 122.9 (CH), 120.0 (CH), 89.3 (C), 79.3 (C), 28.1 (CH3), −0.4 (CH3), −0.8 (CH3); HRMS (ESI) calcd for C33H37N2O8Si $[M+H]^+$ 617.2314, found 617.2315.

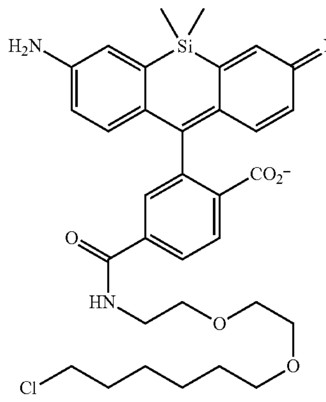

SiR110-HaloTag ligand (8HTL): Acid 15 (48.4 mg, 78.5 μmol) was combined with TSTU (35.4 mg, 118 μmol, 1.5 eq) in DMF (5 mL). After adding DIEA (68 μL, 392 μmol, 5 eq), the reaction was stirred at room temperature for 1 h. A solution of HaloTag(O2)amine61 (16, 39.8 mg, 118 μmol, 1.5 eq) in DMF (250 μL) was then added. The reaction was stirred an additional 30 min at room temperature. It was subsequently diluted with saturated NaHCO3(aq) and extracted with EtOAc (2×). The combined organic extracts were washed with brine, dried over anhydrous MgSO4, filtered, and concentrated under reduced pressure. Silica gel chromatography (0-100% EtOAc/hexanes, linear gradient) afforded Boc2SiR110-HaloTag ligand as an off-white solid.

The dicarbamate intermediate was taken up in CH2Cl2 (2 mL), and trifluoroacetic acid (400 μL) was added. The reaction was stirred at room temperature for 2 h. Toluene (2 mL) was added, and the reaction mixture was concentrated under reduced pressure. The residue was diluted with saturated NaHCO3(aq) and extracted with EtOAc (2×). The combined organic extracts were washed with brine, dried over anhydrous MgSO4, filtered, and concentrated under reduced pressure. Flash chromatography (0-100% EtOAc/CH2Cl2, linear gradient) followed by reverse phase HPLC (10-75% MeCN/H2O, linear gradient, with constant 0.1% v/v TFA additive) afforded 34 mg (59%) of $8_{HTL}$ (TFA salt) as a blue-green solid. $^1$H NMR (CD3OD, 400 MHZ) δ 8.72 (t, J=5.5 Hz, 1H), 8.13 (d, J=8.1 Hz, 1H), 8.07 (dd, J=8.1, 1.6 Hz, 1H), 7.72-7.69 (m, 1H), 7.21 (d, J=2.5 Hz, 2H), 6.82 (d, J=8.9 Hz, 2H), 6.68 (dd, J=8.9, 2.5 Hz, 2H), 3.66-3.53 (m, 8H), 3.51 (t, J=6.6 Hz, 2H), 3.42 (t, J=6.5 Hz, 2H), 1.75-1.64 (m, 2H), 1.54-1.44 (m, 2H), 1.42-1.27 (m, 4H), 0.62 (s, 3H), 0.55 (s, 3H); Analytical LC-MS: tR=10.7 min, >99% purity (10-95% MeCN/H2O, linear gradient, with constant 0.1% v/v TFA additive; 20 min run; 1 mL/min flow; ESI; positive ion mode; detection at 254 nm); HRMS (ESI) calcd for C33H41ClN3O5Si $[M+H]^+$ 622.2499, found 622.2508.

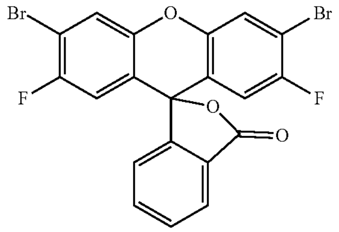 [SMILES: O=C1OC2(c3cc(F)c(Br)cc3Oc3cc(Br)c(F)cc32)c2ccccc21]

3',6'-Dibromo-2',7'-difluoro-3H-spiro[isobenzofuran-1, 9'-xanthen]-3-one (19). A round-bottom flask was charged with 3-bromo-4-fluorophenol (17, 5.0 g, 26 mmol, 2 equiv), phthalic anhydride (18, 1.9 g, 13 mmol 1 equiv), and 12.5 mL methanesulfonic acid. The flask was sealed and evacuated/backfilled with N2(g)(3×). The reaction was stirred at 140° C. for 21 h. The cooled mixture was poured into 7 volumes of stirred ice water and the precipitate was collected by filtration and dried to constant weight. Purification by silica gel chromatography (0-10% EtOAc/hexanes with constant 40% CH2Cl2, linear gradient) afforded 19 (630 mg, 10%) as a white solid. $^1$H NMR (CDCl3, 400 MHZ) δ 8.10-8.04 (m, 1H), 7.76-7.66 (m, 2H), 7.55 (d, 4JHF=5.7 Hz, 2H), 7.18-7.11 (m, 1H), 6.57 (d, 3JHF=8.3 Hz, 2H). $^{13}$C NMR (CDCl3, 101 MHz) δ 168.4 (C), 155.6 (d, 1JCF=245.4 Hz, CF), 152.0 (C), 147.2 (d, 4JCF=2.6 Hz, C), 135.9 (CH), 130.9 (CH), 126.0 (CH), 125.5 (C), 123.7 (CH), 122.4 (CH), 118.8 (d, 3JCF=6.4 Hz, C), 114.3 (d, 2JCF =25.3 Hz, CH), 112.2 (d, 2JCF=23.4 Hz, C), 80.8 (C). 19F NMR (CDCl3, 376 MHz) δ −112.44 (dd, 3JFH=8.2, 4JFH=5.5 Hz). Analytical LC-MS: tR=17.5 min; >99% purity (10-95% MeCN/H2O, linear gradient, with constant 0.1% v/v TFA additive; 20 min run; 1 mL/min flow; ESI; positive ion mode; detection at 254 nm). HRMS (ESI) calcd for C20H9Br2F2O3 [M+H]+ 492.8886, found 492.8885.

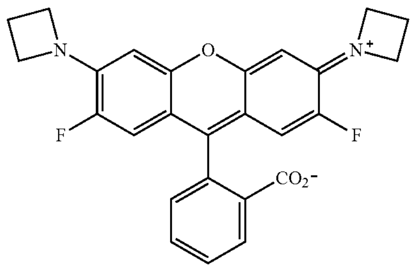

JF552 (9). The following method for 9 is representative for preparation of rhodamines via C—N cross-coupling. A vial was charged with dibromide (19, 49 mg, 100 μmol), azetidine (20, 14 mg, 240 μmol, 2.4 equiv), Pd2dba3 (9 mg, 10 μmol, 0.1 equiv), XPhos (14 mg, 30 μmol, 0.3 equiv), and $Cs_2CO_3$ (157 mg, 484 μmol, 4.8 equiv). The vial was sealed and evacuated/backfilled with N2 (3×). Dioxane (1 mL) was added, and the reaction was flushed again with N2 (3×). The reaction was then stirred at 100° C. for 18 h. It was subsequently cooled to room temperature, diluted with MeOH, deposited onto Celite, and concentrated under reduced pressure. Purification by silica gel chromatography (0-10% MeOH (2 M $NH_3$)/$CH_2Cl_2$, linear gradient; dry load with Celite) afforded 9 (37 mg, 83%) as a purple solid. The 1H and 19F NMR spectra of 9 were identical to those previously reported. 1

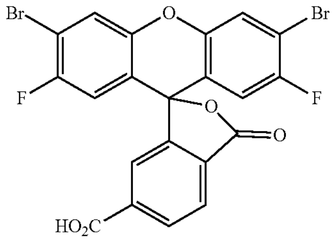 [SMILES: O=C(O)c1ccc2c(c1)C1(OC2=O)c2cc(F)c(Br)cc2Oc2cc(Br)c(F)cc21]

3',6'-Dibromo-2',7'-difluoro-3-oxo-3H-spiro[isobenzofuran-1,9'-xanthene]-6-carboxylic acid (22). A microwave vial was charged with 3-bromo-4-fluorophenol (17, 5.0 g, 26 mmol, 2 equiv), 1,2,4-benzenetricarboxylic anhydride (21, 2.5 g, 13 mmol 1 equiv), and 12.5 mL methanesulfonic acid. The vial was sealed and evacuated/backfilled with nitrogen (3×). The reaction was stirred at 140° C. in an Initiator microwave reactor (Biotage) for 12 h. The cooled mixture was poured into 7 volumes of stirred ice water and the precipitate was collected by filtration and dried to constant weight. The precipitate contained 22 and its 5-carboxylic isomer; the desired product was isolated by crystallization from 140 mL 9:1 toluene: pyridine to afford crude 22 as an off-white solid. This was further purified by silica gel chromatography (2-15% MeOH/CH2Cl2; dry load with Celite) to give 22 (700 mg, 5%) as a white solid. $^{1}$H NMR (DMSO-d6, 400 MHZ) δ 8.25 (dd, J=8.0, 1.3 Hz, 1H), 8.14 (dd, J=8.0, 0.7 Hz, 1H), 7.88 (d, $^{4}$JHF=5.8 Hz, 2H), 7.86 (s, 1H), 7.05 (d, $^{3}$JHF=8.8 Hz, 2H). $^{13}$C NMR (DMSO-d6, 101 MHZ) δ 167.2 (C), 166.0 (C), 154.7 (d, $^{1}$JCF=242.2 Hz, CF), 151.3 (C), 146.8 (d, $^{4}$JCF=2.1 Hz, C), 137.6 (C), 131.5 (CH), 128.7 (C), 126.1 (CH), 124.6 (CH), 121.9 (CH), 118.3 (d, $^{3}$JCF=6.8 Hz, C), 114.9 (d, $^{2}$JCF=25.2 Hz, CH), 111.4 (d, $^{2}$JCF=23.3 Hz, C), 80.3 (C). $^{19}$F NMR (DMSO-d6, 376 MHz) δ −112.68 (dd, $^{3}$ JFH=8.1, $^{4}$JFH=5.5 Hz). Analytical LC-MS: tR=13.4 min; 97% purity (10-95% MeCN/H2O, linear gradient, with constant 0.1% v/v TFA additive; 20 min run; 1 mL/min flow; ESI; positive ion mode; detection at 254 nm). HRMS (ESI) calcd for C21H9Br2F2O5 $[M+H]^+$ 536.8785, found 536.8786.

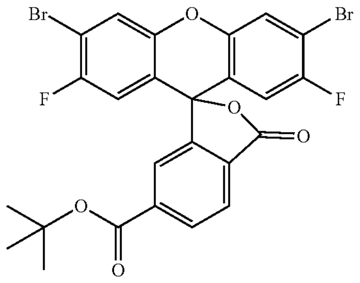 [SMILES: CC(C)(C)OC(=O)c1ccc2c(c1)C1(OC2=O)c2cc(F)c(Br)cc2Oc2cc(Br)c(F)cc21]

tert-Butyl 3',6'-dibromo-2',7'-difluoro-3-oxo-3H-spiro[isobenzofuran-1,9'-xanthene]-6-carboxylate (24). A suspension of 2',7'-difluoro-6-carboxyfluorescein dibromide (22, 340 mg, 0.669 mmol) in toluene (7 mL) was heated to 80° C., and N,N-dimethylformamide di-tert-butyl acetal (23, 2 mL, 8.3 mmol, 12 equiv) was added dropwise over 5 min. The reaction was stirred at 80° C. for 15 min. After cooling the mixture to room temperature, it was diluted with saturated NaHCO3(aq) and extracted with CH2Cl2 (2×). The combined organic extracts were dried over MgSO4 (s), filtered, and concentrated in vacuo. Purification by silica gel chromatography (75% CH2Cl2/hexanes) afforded 24 (305 mg, 81%) as a white solid. $^{1}$H NMR (CDCl3, 400 MHZ) δ 8.28 (dd, J=8.0, 1.3 Hz, 1H), 8.10 (dd, J=8.0, 0.7 Hz, 1H), 7.70 (d, J=1.0 Hz, 1H), 7.58 (d, $^{4}$JHF=5.7 Hz, 2H), 6.54 (d, $^{3}$JHF=8.2 Hz, 2H), 1.57 (s, 9H). $^{13}$C NMR (CDCl3, 101 MHZ) δ 167.7 (C), 163.7 (C), 155.6 (d, $^{1}$JCF=245.6 Hz, CF), 152.0 (C), 147.1 (d, $^{4}$JCF=2.5 Hz, C), 139.3 (C), 131.9 (CH), 128.5 (C), 125.9 (CH), 124.7 (CH), 122.5 (CH), 118.2 (d, $^{3}$JCF=6.3 Hz, C), 114.3 (d, $^{2}$JCF=25.3 Hz, CH), 112.5 (d, $^{2}$JCF=23.4 Hz, C), 83.2 (C), 81.0 (C), 28.2 (CH3). $^{19}$F NMR (CDCl3, 376 MHz) δ −112.18 (dd, $^{3}$JFH=8.1, $^{4}$JFH 5.5 Hz). Analytical LC-MS: tR=19.3 min, >99% purity (10-95% MeCN/H2O, linear gradient, with constant 0.1% v/v TFA additive; 20 min run; 1 mL/min flow; ESI; positive ion mode; detection at 254 nm). HRMS (ESI) calcd for C25H17Br2F2O5 $[M+H]^+$ 592.9411, found 592.9419.

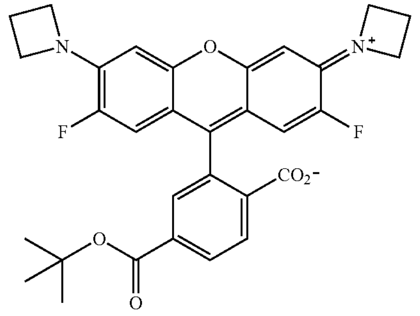

6-tert-Butoxycarbonyl-JF552 (25). The title compound was prepared from dibromide 24 and azetidine (20) following the C—N cross-coupling method described for 9 (62%, purple solid). $^{1}$H NMR (CDCl3, 400 MHZ) δ 8.22 (dd, J=8.0, 1.3 Hz, 1H), 8.03 (dd, J=8.0, 0.7 Hz, 1H), 7.73 (t, J=1.0 Hz, 1H), 6.27-6.13 (m, 4H), 4.02 (td, J=7.4 Hz, 5JHF=2.1 Hz, 8H), 2.37 (p, J=7.3 Hz, 4H), 1.57 (s, 9H). $^{13}$C NMR (CDCl3, 101 MHZ) δ 168.5 (C), 164.3 (C), 152.5 (C), 148.6 (d, 4JCF=1.1 Hz, C), 148.6 (d, 1JCF=239.3 Hz, CF), 142.3 (d, 2JCF=13.2 Hz, C), 138.4 (C), 131.1 (CH), 130.2 (C), 125.2 (CH), 125.1 (CH), 113.6 (d, 2JCF=21.3 Hz, CH), 106.0 (d, 3JCF=6.3 Hz, C), 100.7 (d, 3JCF=4.9 Hz, CH), 85.0 (C), 82.7 (C), 53.9 (d, 4JCF=2.6 Hz, CH2), 28.2 (CH3), 17.8 (d, 5JCF=2.4 Hz, CH2). $^{19}$F NMR (CDCl3, 376 MHz) δ −137.92--138.03 (m). Analytical LC-MS: tR=13.27 min, 97% purity; (10-95% MeCN/H2O, linear gradient, with constant 0.1% v/v TFA additive; 20 min run; 1 mL/min flow; ESI; positive ion mode; detection at 550 nm). HRMS (ESI) calcd for C31H29F2N2O5 $[M+H]^+$ 547.2039, found 547.2030.

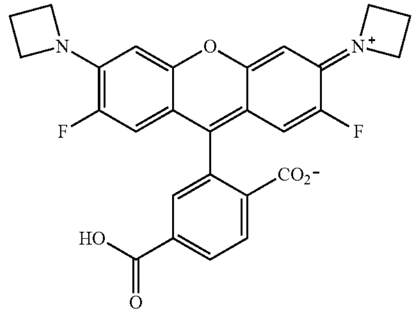

6-Carboxy-JF552 (26). Ester 25 (23.2 mg, 30.4 μmol) was taken up in CH2Cl2 (2.5 mL) to which TFA (0.5 mL) was added. The reaction was stirred at room temperature for 6 h. Toluene (3 mL) was added; the reaction mixture was concentrated under reduced pressure and then azeotroped with MeOH (3×) to provide 25 as a dark pink solid (25.0 mg, 98%, TFA salt). Analytical LC-MS and NMR indicated that the material was >95% pure and thus was used without further purification. $^{1}$H NMR (CD3OD, 400 MHZ,) δ 8.46-8.37 (m, 2H), 7.96 (d, J=1.4 Hz, 1H), 6.77 (d, $^{3}$JHF=12.6 Hz, 2H), 6.65 (d, $^{4}$JHF=7.3 Hz, 2H), 4.50 (t, J=7.4 Hz, 8H), 2.57 (p, J=7.5 Hz, 4H). $^{13}$C NMR (CD3OD, 101 MHZ,) δ 167.6 (C), 167.4 (C), 155.9 (C), 151.7 (d, $^{1}$JCF=251.0 Hz, CF), 148.8 (d, $^{2}$JCF=15.4 Hz, C), 136.2 (C), 135.0 (C), 133.0 (CH), 132.7 (CH), 132.0 (CH), 114.5 (d, $^{3}$JCF=8.5 Hz, C), 113.7 (d, $^{2}$JCF=21.6 Hz, CH), 97.8 (d, $^{3}$JCF=5.5 Hz, CH), 55.6 (CH2), 17.9 (CH2). $^{19}$F NMR (CD3OD, 376 MHz) δ −75.35 (s, 3F), −130.54 (dd, $^{3}$JFH=12.8, $^{4}$JFH=7.6 Hz, 2F). Analytical LC-MS: tR=13.26 min, 96% purity (10-95% MeCN/H2O, linear gradient, with constant 0.1% v/v TFA additive; 20 min run; 1 mL/min flow; ESI; positive ion mode; detection at 550 nm). HRMS (ESI) calcd for C27H21F2N205 [M+H]$^{+}$ 491.1413, found 491.1420.

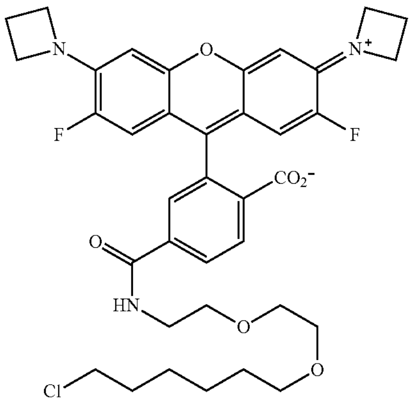

JF552-HaloTag ligand ($9_{HTL}$). 6-Carboxy-JF552 (26, 7 mg, 12 μmol) was combined with DSC(7 mg, 27 μmol, 2.2 equiv) in DMF (0.5 mL). After adding Et3N (10 μL, 72 μmol, 6 equiv) and DMAP (0.2 mg, 1.2 μmol, 0.1 equiv), the reaction was stirred at room temperature for 1 h while shielded from light. HaloTag (02) amine61 (16, TFA salt, 7 mg, 30 μmol, 2.5 equiv, Promega) was then added. The reaction was stirred overnight at room temperature, then concentrated under reduced pressure. The crude material was purified by reverse phase HPLC (10-90% MeCN/H2O, linear gradient, with constant 0.1% v/v TFA additive) to provide 7.3 mg (91%, TFA salt) of $9_{HTL}$ as a pink solid. 1H NMR (CD3OD, 400 MHZ) δ 8.77 (t, J=5.5 Hz, 1H), 8.41 (d, J=8.2 Hz, 1H), 8.20 (dd, J=8.2, 1.8 Hz, 1H), 7.78 (d, J=1.7 Hz, 1H), 6.77 (d, 3JHF=12.7 Hz, 2H), 6.66 (d, 4JHF=7.3 Hz, 2H), 4.50 (t, J=7.5 Hz, 8H), 3.70-3.55 (m, 8H), 3.53 (t, J=6.6 Hz, 2H), 3.44 (t, J=6.5 Hz, 2H), 2.58 (p, J=7.6 Hz, 4H) 1.84-1.63 (m, 2H), 1.59-1.47 (m, 2H), 1.47-1.28 (m, 4H). 19F NMR (CD3OD, 376 MHz) δ −76.55 (s, 3F), −131.84 (dd, 3JFH=12.9, 4JFH=7.4 Hz, 2F). Analytical LC-MS: tR=12.44 min, >99% purity; (10-95% MeCN/$H_2O$, linear gradient, with constant 0.1% v/v TFA additive; 20 min run; 1 mL/min flow; ESI; positive ion mode; detection at 550 nm). HRMS (ESI) calcd for C37H41ClF2N3O6 [M+H]$^{+}$ 696.2652, found 696.2656.

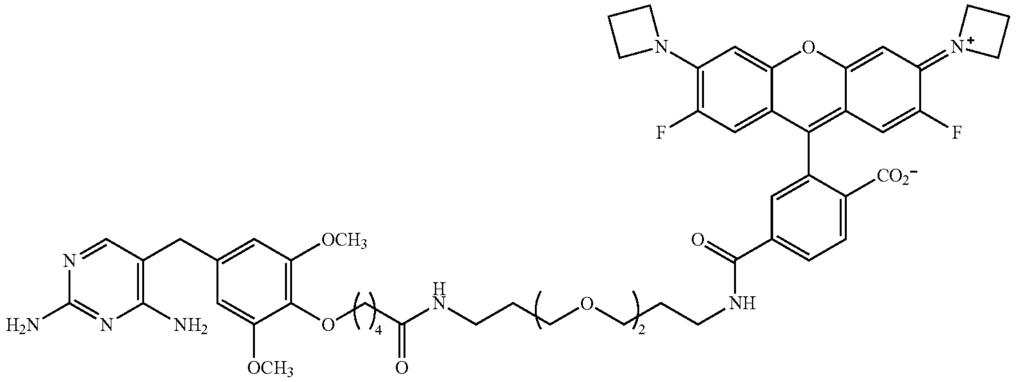

JF552-trimethoprim (JF552-TMP; 9TMP). The following method for 9TMP is representative for amidation to prepare HaloTag ligands, SNAP-tag ligands, TMP conjugates, Hoechst conjugates, and other amides unless otherwise noted. 6-Carboxy-JF552 (26, 7 mg, 12 μmol) was combined with TSTU (8.1 mg, 27 μmol, 2.2 equiv) in DMF (0.5 mL). After adding DIEA (13 μL, 72 μmol, 6 equiv), the reaction was stirred at room temperature for 1 h while shielded from light. TMP amine14 (28, 14 mg, 24 μmol, 2 equiv) was then added. The reaction was stirred overnight at room temperature, then concentrated under reduced pressure. The crude material was purified by reverse phase HPLC(10-90% MeCN/H2O, linear gradient, with constant 0.1% v/v TFA additive) to provide 13.8 mg (44%, TFA salt) of 9TMP as a pink solid. $^{1}$H NMR (CD3OD, 400 MHZ) δ 8.67 (t, J=5.6 Hz, 1H), 8.38 (d, J=8.2 Hz, 1H), 8.17 (dd, J=8.2, 1.8 Hz, 1H), 7.77 (d, J=1.7 Hz, 1H), 7.22 (s, 1H), 6.77 (d, $^{3}$JHF=12.6 Hz, 2H), 6.65 (d, $^{4}$JHF=7.3 Hz, 2H), 6.55 (s, 2H), 4.49 (t, J=7.7 Hz, 8H), 3.90 (t, J=6.1 Hz, 2H), 3.79 (s, 6H), 3.66 (s, 2H), 3.62-3.56 (m, 8H), 3.54-3.45 (m, 6H), 3.23 (t, J=6.9 Hz, 2H), 2.57 (p, J=7.7 Hz, 4H), 2.23 (t, J=7.3 Hz, 2H), 1.88 (p, J=6.5 Hz, 2H), 1.82-1.64 (m, 6H). $^{19}$F NMR (CD3OD, 376 MHz) δ −75.30 (s, 3F), −130.56–−130.70 (m, 2F). Analytical LC-MS: tR=9.93 min, >99% purity; (10-95% MeCN/H2O, linear gradient, with constant 0.1% v/v TFA additive; 20 min run; 1 mL/min flow; ESI; positive ion mode; detection at 550 nm). HRMS (ESI) calcd for C55H65F2N8O11 [M+H]$^{+}$ 1051.4741, found 1051.4737.

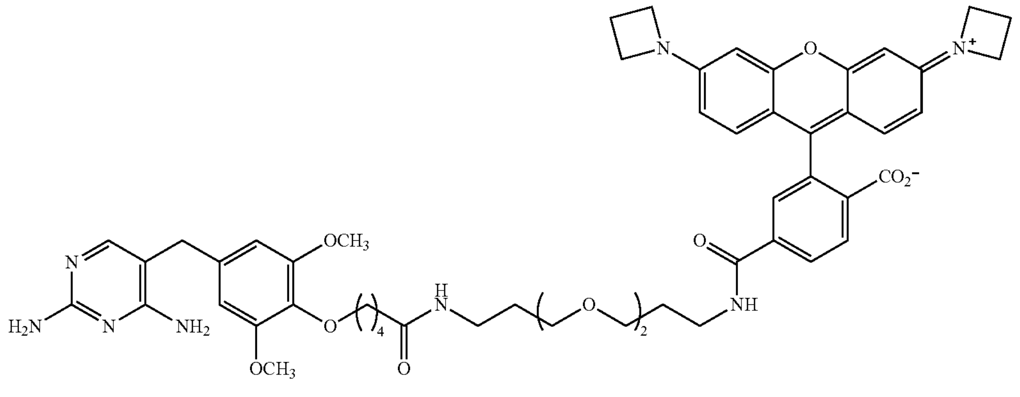

JF549-Trimethoprim (JF549-TMP; 6TMP). The title compound was prepared from 6-carboxy-JF54912 (27) and TMP amine (28) following the amidation method described for 9TMP (65%, pink solid, TFA salt). 1H NMR (CD3OD, 400 MHZ) δ 8.66 (t, J=5.7 Hz, 1H), 8.38 (d, J=8.2 Hz, 1H), 8.18 (dd, J=8.2, 1.8 Hz, 1H), 7.79 (d, J=1.7 Hz, 1H), 7.23 (s, 1H), 7.06 (d, J=9.2 Hz, 2H), 6.60 (dd, J=9.2, 2.2 Hz, 2H), 6.55 (s, 2H), 6.54 (d, J=2.1 Hz, 2H), 4.30 (t, J=7.6 Hz, 8H), 3.90 (t, J=6.1 Hz, 2H), 3.79 (s, 6H), 3.66 (s, 2H), 3.61-3.54 (m, 8H), 3.53-3.41 (m, 6H), 3.22 (t, J=6.9 Hz, 2H), 2.56 (p, J=7.6 Hz, 6H), 2.22 (t, J=7.3 Hz, 2H), 1.87 (p, J=6.4 Hz, 2H), 1.82-1.58 (m, 6H). Analytical LC-MS: tR=9.07 min, 99% purity; (10-95% MeCN/H2O, linear gradient, with constant 0.1% v/v TFA additive; 20 min run; 1 mL/min flow; ESI; positive ion mode; detection at 550 nm). HRMS (ESI) calcd for C55H67N8O11 $[M+H]^+$ 1015.4929, found 1015.4934.

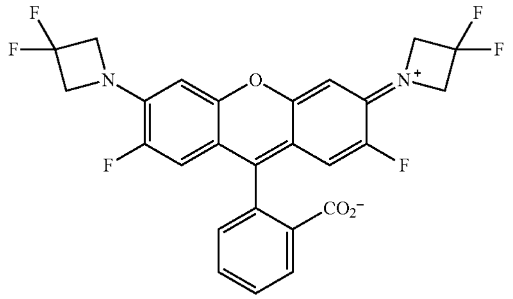

JF526 (10). The title compound was prepared from dibromide 19 and 3,3-difluoroazetidine hydrochloride (29) following the C—N cross-coupling method described for 9 (65%, pink solid). $^{1H}$ NMR (CD3CN, 400 MHZ) δ 7.99 (dt, J=7.5, 0.9 Hz, 1H), 7.77 (td, J=7.5, 1.3 Hz, 1H), 7.71 (td, J=7.5, 1.1 Hz, 1H), 7.22 (dt, J=7.6, 0.9 Hz, 1H), 6.57-6.38 (m, 4H), 4.42 (td, $^{3}$JHF=12.1, $^{5}$JHF=2.1 Hz, 8H). $^{13}$C NMR (CDCl3, 101 MHZ) δ 169.0 (C), 152.3 (C), 148.7 (d, $^{1}$JCF=239.5 Hz, CF), 148.3 (C), 139.75 (d, $^{2}$JCF=13.6 Hz, C), 135.4 (CH), 130.3 (CH), 126.8 (C), 125.5 (CH), 123.9 (CH), 116.1 (td, J=272.7, 3.4 Hz, $CF_2$), 114.2 (d, $^{2}$JCF=21.5 Hz, CH), 108.7 (d, $^{3}$JCF=6.2 Hz, C), 102.0 (d, $^{3}$JCF=3.7 Hz, CH), 83.1 (C), 64.5 (td, $^{2}$JCF=26.9, $^{4}$JCF=2.3 Hz, CH2). $^{19}$F NMR (CD3CN, 376 MHz) δ −98.97 (p, $^{3}$JFH=12.4 Hz, 4F), −135.77--136.03 (m, 2F). Analytical LC-MS: tR=13.47 min, >99% purity (10-95% MeCN/H2O, linear gradient, with constant 0.1% v/v TFA additive; 20 min run; 1 mL/min flow; ESI; positive ion mode; detection at 550 nm). HRMS (ESI) calcd for C26H17F6N2O3 $[M+H]^+$ 519.1138, found 519.1146.

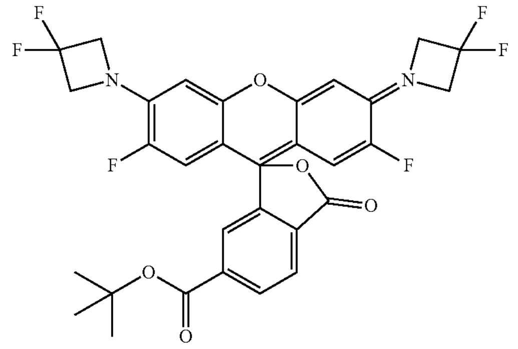

6-tert-Butoxycarbonyl-JF526 (30). The title compound was prepared from dibromide 24 and 3,3-difluoroazetidine hydrochloride (29) following the C—N cross-coupling method described for 9 (69%, white solid). 1H NMR (CDCl3, 400 MHZ) δ 8.24 (dd, J=8.0, 1.3 Hz, 1H), 8.05 (dd, J=8.0, 0.8 Hz, 1H), 7.73 (s, 1H), 6.33-6.29 (m, 4H), 4.36 (td, 3JHF=11.8, 5JHF=2.1 Hz, 8H), 1.57 (s, 9H). 19F NMR (CDCl3, 376 MHz) δ −100.16 (p, 3JFH=12.0 Hz, 4F), −137.31 (ddt, 3JFH=12.4, 4JFH=7.6, 5JFH=2.2 Hz, 2F). $^{13}$C NMR (CDCl3, 101 MHz) δ 168.2 (C), 164.1 (C), 152.4 (C), 148.7 (d, 1JCF=239.7 Hz, CF), 148.3 (d, 4JCF=1.6 Hz, C), 140.0 (C), 138.7 (C), 131.3 (CH), 129.7 (C), 125.3 (CH), 125.0 (CH), 114.1 (d, 2JCF=21.7 Hz, CH), 108.0 (d, 3JCF=6.4 Hz, C), 102.0 (d, 3JCF=3.8 Hz, CH), 83.5 (C), 82.9 (C), 64.5 (td, 2JCF=26.9 Hz, 4JCF=2.2 Hz, $CH_2$), 28.2 ($CH_3$). Analytical LC-MS: tR=15.07 min, >99% purity (10-95% MeCN/H2O, linear gradient, with constant 0.1% v/v TFA additive; 20 min run; 1 mL/min flow; ESI; positive ion mode; detection at 550 nm). HRMS (ESI) calcd for C31H25F6N2O5 $[M+H]^+$ 619.1662, found 619.1663.

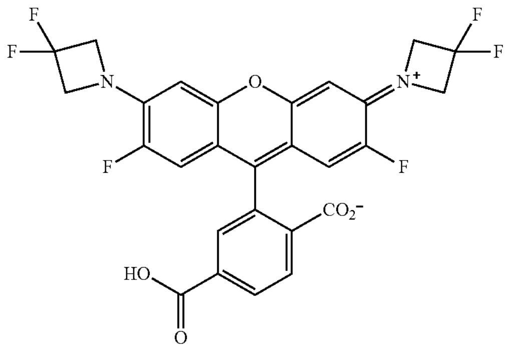

6-Carboxy-JF526 (31): Ester 30 (31.0 mg, 50 μmol) was taken up in $CH_2Cl_2$ (2.5 mL) to which TFA (0.5 mL) was added. The reaction was stirred at room temperature for 6 h. Toluene (3 mL) was added; the reaction mixture was concentrated under reduced pressure and then azeotroped with MeOH (3×) to provide 31 as a dark pink solid (33.3 mg, 98%, TFA salt). Analytical LC-MS and NMR indicated that the material was >95% pure and was used without further purification. $^{1H}$NMR (CD3CN, 400 MHZ) δ 8.31 (dd, J=8.1, 1.5 Hz, 1H), 8.20 (dd, J=8.1, 0.6 Hz, 1H), 7.87-7.80 (m, 1H), 6.68 (d, $^3$JHF=12.5 Hz, 2H), 6.59 (d, $^4$JHF=7.6 Hz, 2H), 4.58 (td, $^3$JHF=12.0, $^5$JHF=2.1 Hz, 8H). $^{13}$C NMR (CD3OD, 101 MHZ) δ 167.9 (C), 167.5 (C), 154.1 (C), 151.4 (d, $^1$JCF=247.5 Hz, CF), 146.3 (d, $^2$JCF=11.8 Hz, C), 137.1 (C), 134.1 (C), 132.9 (CH), 131.2 (CH), 130.1 (CH), 117.1 (t, $^1$JCF=270.7 Hz, $^5$JCF=3.1 Hz, $CF_2$), 114.4 (d, $^2$JCF=22.0 Hz, CH), 114.0 (d, $^3$JCF=5.2 Hz, C), 101.0 (d, $^3$JCF=3.5 Hz, CH), 66.0 (t, $^2$JCF=28.7 Hz, CH2). $^{19}$F NMR (CD3CN, 376 MHZ,) δ −76.70 (s, 3F), −101.85 (p, $^3$JFH=11.9 Hz, 4F), −133.67--134.44 (m, 2F). Analytical LC-MS: tR=11.70 min, 97% purity (10-95% MeCN/H2O, linear gradient, with constant 0.1% v/v TFA additive; 20 min run; 1 mL/min flow; ESI; positive ion mode; detection at 550 nm). HRMS (ESI) calcd for C27H17F6N2O5 $[M+H]^+$ 563.1042, found 563.1045.

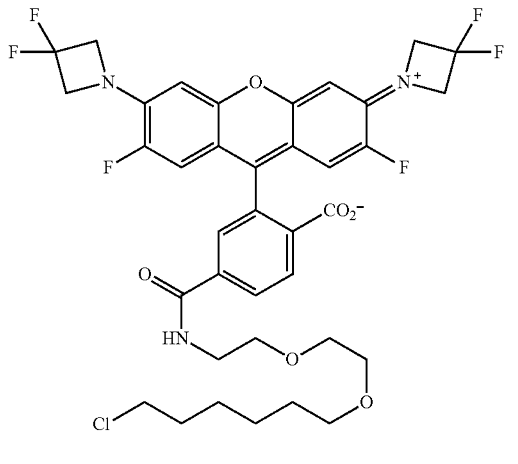

JF526-HaloTag ligand (10HTL). The title compound was prepared from 6-carboxy-JF526 (31) and HaloTag(O2) amine[61] (16) following the amidation procedure method described for 9TMP (53%, white solid, TFA salt). $^1$H NMR (CD3OD, 400 MHZ) δ 8.72 (d, J=4.6 Hz, 1H), 8.22 (d, J=8.2 Hz, 1H), 8.18 (dd, J=8.1, 1.5 Hz, 1H), 7.68 (s, 1H), 6.69 (d, $^4$JHF =7.6 Hz, 2H), 6.60 (d, $^3$JHF=12.3 Hz, 2H), 4.55 (t, J=11.8 Hz, 8H), 3.66-3.49 (m, 10H), 3.42 (t, J=6.5 Hz, 2H), 1.77-1.64 (m, 2H), 1.50 (m, J=6.8 Hz, 2H), 1.45-1.25 (m, 4H). $^{19}$F NMR (CD3OD, 376 MHz) δ −75.35 (s, 3F), −100.75 (p, $^3$JFH=11.9 Hz, 4F), −134.45--136.80 (m, 2F). Analytical LC-MS: tR=13.98 min, >99% purity; (10-95% MeCN/H2O, linear gradient, with constant 0.1% v/v TFA additive; 20 min run; 1 mL/min flow; ESI; positive ion mode; detection at 254 nm). HRMS (ESI) calcd for C37H37ClF6N3O6, $[M+H]^+$ 768.2275, found 768.2281.

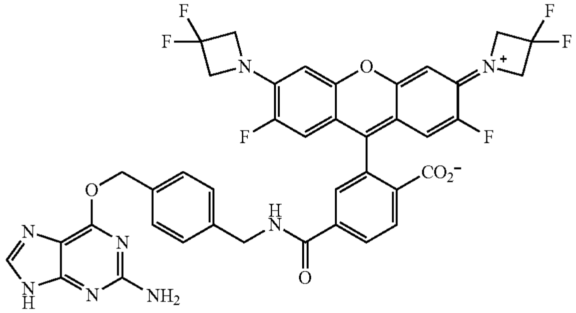

JF526-SNAP-tag ligand ($10_{STL}$). The title compound was prepared from 6-carboxy-JF526 (31) and benzylguanine-amine (BG-NH2, S1, New England Biolabs) following the amidation method described for 9TMP (58%, pink solid, TFA salt). $^1$H NMR (DMF-d7, 400 MHz) δ 9.31 (t, J=5.8 Hz, 1H), 8.36 (dd, J=8.1, 1.4 Hz, 1H), 8.22 (s, 1H), 8.14 (d, J=7.9 Hz, 1H), 7.94 (d, J=1.2 Hz, 1H), 7.51 (d, J=8.1 Hz, 2H), 7.39 (d, J=8.0 Hz, 2H), 6.70 (d, $^3$JHF=12.5 Hz, 2H), 6.66 (d, $^4$JHF=7.8 Hz, 2H), 5.53 (s, 2H), 4.66-4.36 (m, 10H). $^{19}$F NMR (DMF-d7, 376 MHZ) δ −74.57 (s, 3F), −99.94 (p, $^3$JFH=12.3 Hz, 4F), −137.36 (dd, $^3$JFH=12.7, $^4$JFH =7.9 Hz, 2F). Analytical LC-MS: tR=9.28 min, >99% purity (10-95% MeCN/H2O, linear gradient, with constant 0.1% v/v TFA additive; 20 min run; 1 mL/min flow; ESI; positive ion mode; detection at 550 nm). HRMS (ESI) calcd for C40H29F6N8O5 $[M+H]^+$ 815.2165, found 815.2164.

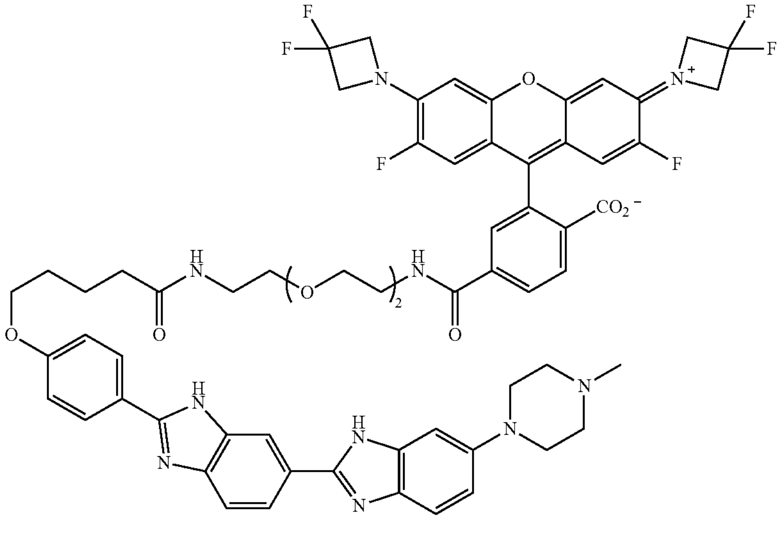

JF526-Hoechst (10HST). The title compound was prepared from 6-carboxy-JF526 (31) and Hoechst-PEG2-NH263 (S2) following the amidation method described for 9TMP (76%, purple solid, TFA salt). 1H NMR (CD3OD, 400 MHZ) δ 8.33 (d, J=1.7 Hz, 1H), 8.22-8.16 (m, 2H), 8.07-7.98 (m, 2H), 8.01 (dd, J=8.5, 1.8 Hz, 1H), 7.88-7.84 (m, 2H), 7.72 (d, J=9.1 Hz, 1H), 7.40 (dd, J=9.1, 2.3 Hz, 1H), 7.31 (d, J=2.2 Hz, 1H), 7.13-7.06 (m, 2H), 6.63-6.44 (m, 4H), 4.47 (t, J=12.0 Hz, 8H), 4.08 (t, J=6.2 Hz, 2H), 3.65-3.50 (m, 20H), 3.47 (t, J=5.4 Hz, 2H), 3.28 (t, J=5.7 Hz, 2H), 3.02 (s, 3H), 2.39 (t, J=7.2 Hz, 2H), 2.08 (p, J=6.8 Hz, 2H). 19F NMR (CD3OD, 376 MHz) δ −75.40 (s, 12F), −100.67 (p, 3JFH=11.6 Hz, 4F), −133.47-−134.98 (m, 2F). Analytical LC-MS: tR=9.16 min, >99% purity (10-95% MeCN/H2O, linear gradient, with constant 0.1% v/v TFA additive; 20 min run; 1 mL/min flow; ESI; positive ion mode; detection at 254 nm). HRMS (ESI) calcd for C62H59F6N10O8, [M+H]+ 1185.4422, found 1185.4430.

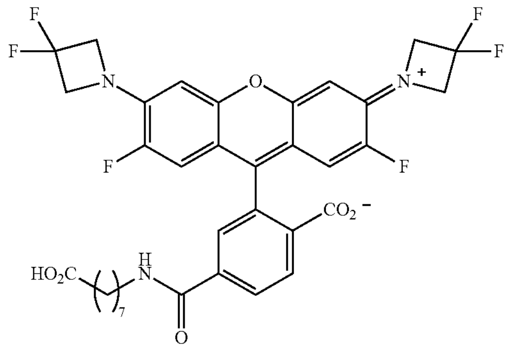

4-((7-Carboxyheptyl) carbamoyl)-2-(3-(3,3-difluoro-1λ4-azetidin-1-ylidene)-6-(3,3-difluoroazetidin-1-yl)-2,7-difluoro-3H-xanthen-9-yl)benzoate (S4). The title compound was prepared from 6-carboxy-JF526 (31) and 8-aminooctanoic acid (S3) following the amidation method described for 9TMP (38%, pink solid, TFA salt). $^1$H NMR (CD3OD, 400 MHZ) δ 8.70 (t, J=5.3 Hz, 1H), 8.21 (d, J=7.9 Hz, 1H), 8.15 (dd, J=8.1, 1.5 Hz, 1H), 7.65 (s, 1H), 6.78-6.49 (m, 4H), 4.56 (m, 8H), 3.35-3.34 (m, 2H), 2.26 (t, J=7.4 Hz, 2H), 1.64-1.50 (m, 4H), 1.41-1.23 (m, 6H). $^{19}$F NMR (CD3OD, 376 MHz) δ −75.38 (s, 3F), −100.76 (d, $^3$JFH=10.9 Hz, 4F), −135.03-−138.56 (m, 2F). Analytical LC-MS: tR=12.43 min, >99% purity (10-95% MeCN/H2O, linear gradient, with constant 0.1% v/v TFA additive; 20 min run; 1 mL/min flow; ESI; positive ion mode; detection at 550 nm). HRMS (ESI) calcd for C35H32F6N306 [M+H]$^+$ 704.2195, found 704.2193.

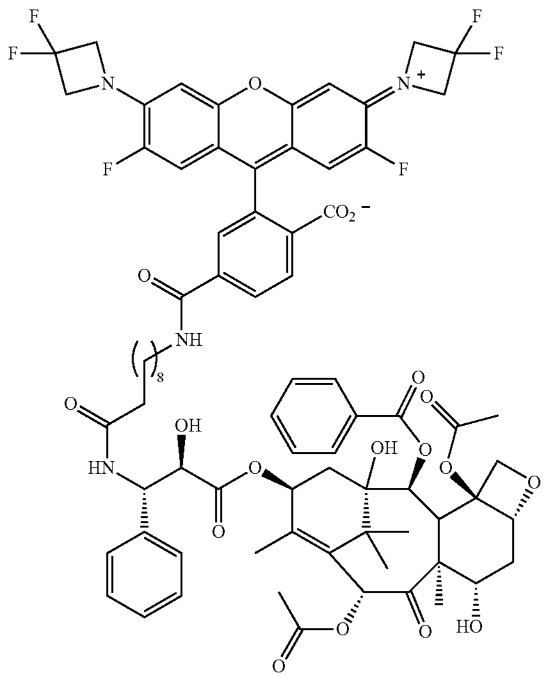

JF526-Taxol (10TXL). S4 (4 mg, 6 μmol, Scheme S1) was combined with HATU (12 mg, 31 μmol, 5.3 equiv) in DMSO (0.4 mL). After adding DIEA (50 μL, 37 mg, 290 μmol, 48 equiv), the reaction was stirred at ambient temperature for 5 min while shielded from light. 3'-aminodocetaxel4 (S5, 8 mg, 12 μmol, 2 equiv, Scheme S1) was then added. The reaction was stirred for 2 days at room temperature, then concentrated under reduced pressure. The crude material was purified by reverse phase HPLC(10-90% MeCN/H2O, linear gradient, with constant 0.1% v/v TFA additive) to provide 2.7 mg of 10TXL (36%, TFA salt) as an off-white solid. 1H NMR (CD3OD, 400 MHz) δ 8.66 (t, J=5.7 Hz, 1H), 8.40 (d, J=9.1 Hz, 1H), 8.24 (d, J=8.1 Hz, 1H), 8.14 (dd, J=8.1, 1.6 Hz, 1H), 8.10-8.05 (m, 2H), 7.68 (s, 1H), 7.66-7.59 (m, 1H), 7.54 (t, J=7.5 Hz, 2H), 7.44-7.30 (m, 4H), 7.30-7.19 (m, 1H), 6.73 (d, 3JHF=7.4 Hz, 2H), 6.65 (d, 4JHF =12.2 Hz, 2H), 6.22-6.09 (m, 1H), 5.63 (d, J=7.2 Hz, 1H), 5.46 (d, J=4.3 Hz, 1H), 5.26 (s, 1H), 4.99 (d, J=9.6 Hz, 1H), 4.69-4.44 (m, 9H), 3.86 (d, J=7.1 Hz, 1H), 2.44 (m 1H), 2.34 (s, 3H), 2.31-2.18 (m, 2H), 2.08-2.00 (m, 2H), 1.88 (m, 3H), 1.86-1.76 (m, 1H), 1.68 (s, 2H), 1.57 (m, 4H), 1.30 (m, 6H), 1.17 (s, 3H), 1.10 (s, 3H). 19F NMR (CD3OD, 376 MHZ) δ −75.38 (s, 9F), −100.82 (p, 3JHF=12.0 Hz, 4F), −132.20-−134.93 (m, 2F). Analytical LC: tR=13.64 min, >99% purity (10-95% MeCN/H2O, linear gradient, with constant 0.1% v/v TFA additive; 20 min run; 1 mL/min flow; detection at 550 nm). Analytical LC-MS: tR=3.68 min, >99% purity (Phenomenex Kinetex 2.1 mmx30 mm 2.6 μm C18 column; 5 μL injection; 5-98% MeCN/$H_2O$, linear gradient, with constant 0.1% v/v HCO2H additive; 6 min run; 0.5 mL/min flow; ESI; positive ion mode; detection at 550 nm). HRMS (ESI) calcd for C73H75F6N4O17 [M+H]$^+$ 1393.5031, found 1393.5042.

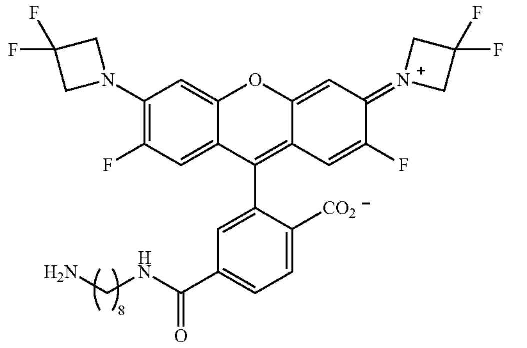

6-Aminohexyl)-3',6'-bis(3,3-difluoroazetidin-1-yl)-2',7'-difluoro-3-oxo-3H-spiro[isobenzofuran-1,9'-xanthene]-6-carboxamide (S7). The title compound was prepared from 6-carboxy-JF526 (31) and hexane-1,6-diamine (S6, Scheme S1) following the amidation method described for 9TMP (41%, pink solid, TFA salt). $^{1}$H NMR (CD3OD, 400 MHZ) δ 8.22 (d, J=8.1 Hz, 1H), 8.15 (dd, J=8.1, 1.6 Hz, 1H), 7.66 (d, J=1.3 Hz, 1H), 6.69 (d, $^{4}$JHF=7.5 Hz, 2H), 6.60 (d, $^{3}$JHF=12.2 Hz, 2H), 4.55 (t, $^{3}$JHF=11.8 Hz, 8H), 3.36 (t, J=7.2 Hz, 2H), 2.90 (t, J=7.6 Hz, 2H), 1.63 (m, 4H), 1.40 (m, 4H). $^{19}$F NMR (CD3OD, 376 MHZ) δ −75.35 (s, 6F), −100.77 (p, $^{3}$JHF=12.2 Hz, 4F), −133.10-−135.26 (m, 2F). Analytical LC-MS: tR=9.86 min, >99% purity (10-95% MeCN/H2O, linear gradient, with constant 0.1% v/v TFA additive; 20 min run; 1 mL/min flow; ESI; positive ion mode; detection at 550 nm). HRMS (ESI) calcd for C33H31F6N4O4 $[M+H]^+$ 661.2244, found 661.2241.

JF526-Pepstatin A ($10_{PEP}$). Pepstadin A (S8, 8.3 mg, 12 μmol, 2 equiv) was combined with TSTU (4 mg, 15 μmol, 2.4 equiv) in DMF (0.3 mL). After adding DIEA (53 μL, 305 μmol, 50 equiv), the reaction was stirred at room temperature for 5 min while shielded from light. S7 (4 mg, 6 μmol, 1 equiv) was then added. The reaction was stirred for 2 days at room temperature, then concentrated under reduced pressure. The crude material was purified by reverse phase HPLC(10-90% MeCN/H2O, linear gradient, with constant 0.1% v/v TFA additive) to provide 1.7 mg of $10_{PEP}$ (19%, TFA salt) as an off-white solid. $^{1}$H NMR (CD3OD, 400 MHZ) δ 8.67 (s, 1H), 8.30-8.07 (m, 2H), 7.98 (d, J=8.0 Hz, 1H), 7.94 (d, J=8.3 Hz, 1H), 7.66 (m, 2H), 7.42 (d, J=9.4 Hz, 1H), 6.66 (d, $^{4}$JHF=7.5 Hz, 2H), 6.55 (d, $^{3}$JHF=12.3 Hz, 2H), 4.51 (t, J=11.9 Hz, 8H), 4.25 (q, J=7.1 Hz, 1H), 4.19-4.08 (m, 2H), 4.05-3.88 (m, 2H), 3.21-3.06 (m, 2H), 2.36 (m, 2H), 2.25 (d, J=6.6 Hz, 2H), 2.18-1.93 (m, 5H), 1.69-1.45 (m, 7H), 1.43-1.23 (m, 8H), 1.09-0.79 (m, 30H). 19F NMR (CD3OD, 376 MHz) δ −77.03 (s, 18F), −102.47 (p, $^{3}$JFH=11.9 Hz, 4F), −135.83-−137.96 (m, 2F). Analytical LC-MS: tR=13.72 min, >99% purity (10-95% MeCN/H2O, linear gradient, with constant 0.1% v/v TFA additive; 20 min run; 1 mL/min flow; ESI; positive ion mode; detection at 550 nm). HRMS (ESI) calcd for C67H92F6N9O12 $[M+H]^+$ 1328.6770, found 1328.6783.

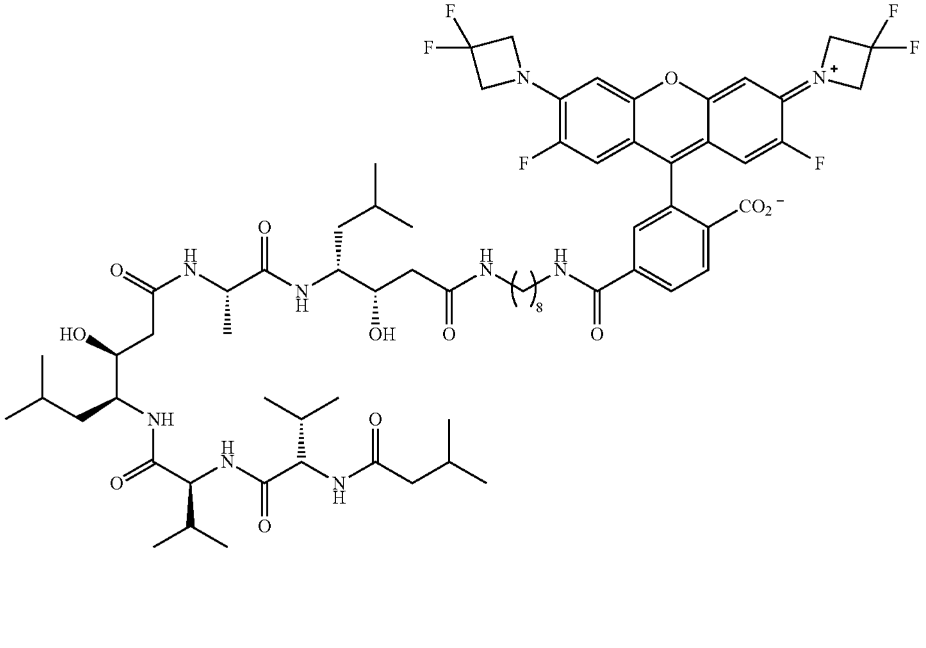

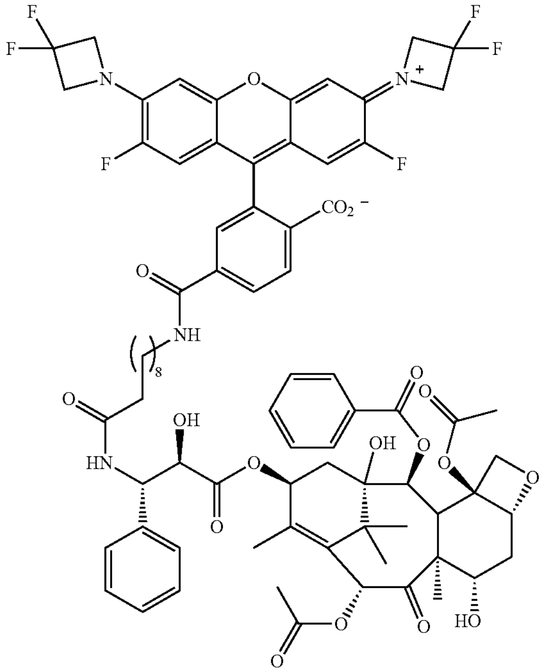

JF525-Taxol (7TXL). 6-Carboxy-JF5252 (S9, 5 mg, 8 μmol) was combined with TSTU (2.8 mg, 9 μmol, 1.2 equiv) in DMF (1 mL). After adding DIEA (28 μL, 160 μmol, 20 equiv), the reaction was stirred at room temperature for 1 h. S3 (1.5 mg, 9 μmol, 1.1 equiv, Scheme S1) was then added and the reaction was stirred for 2 days at room temperature while shielded from light. TSTU (2.8 mg, 9 μmol, 1.2 equiv) and S5 (13 mg, 22 μmol, 2 equiv, Scheme S1) was then added and the reaction was stirred for 4 days at room temperature while shielded from light, then concentrated under reduced pressure. The crude material was purified by reverse phase HPLC(10-90% MeCN/H2O, linear gradient, with constant 0.1% v/v TFA additive) to provide 1.0 mg of 7TXL (9%, TFA salt) as a pink solid. 1H NMR (CD3OD, 400 MHZ) δ 8.38 (d, J=8.2 Hz, 1H), 8.18 (dd, J=8.2, 1.8 Hz, 1H), 8.12-8.02 (m, 2H), 7.79 (d, J=1.7 Hz, 1H), 7.63 (t, J=7.4 Hz, 1H), 7.53 (t, J=7.6 Hz, 2H), 7.44-7.32 (m, 4H), 7.25 (t, J=6.9 Hz, 1H), 7.16 (dd, J=9.2, 3.0 Hz, 2H), 6.81 (s, 2H), 6.77-6.70 (m, 2H), 6.13 (t, J=9.0 Hz, 1H), 5.61 (d, J=7.1 Hz, 1H), 5.46 (d, J=4.2 Hz, 1H), 5.25 (s, 1H), 4.68 (t, 3JHF=11.6 Hz, 8H), 4.58 (d, J=4.3 Hz, 1H), 4.26-4.09 (m, 3H), 3.85 (d, J=7.2 Hz, 1H), 3.35 (m, 3H), 2.52-2.38 (m, 1H), 2.34 (s, 3H), 2.32-2.16 (m, 2H), 2.08-1.98 (m, 2H), 1.88 (d, J=1.4 Hz, 2H), 1.67 (s, 3H), 1.64-1.50 (m, 4H), 1.31 (m, 6H), 1.15 (s, 3H), 1.08 (s, 6H). 19F NMR (CD3OD, 376 MHZ) δ −75.39 (s, 9F), −100.74 (p, 3JFH=11.6 Hz, 4F). Analytical LC: tR=12.52 min, >99% purity (10-95% MeCN/H2O, linear gradient, with constant 0.1% v/v TFA additive; 20 min run; 1 mL/min flow; ESI; positive ion mode; detection at 550 nm). Analytical LC-MS: tR=3.44 min, >99% purity (Phenomenex Kinetex 2.1 mm×30 mm 2.6 μm C18 column; 5 μL injection; 5-98% MeCN/H2O, linear gradient, with constant 0.1% v/v HCO2H additive; 6 min run; 0.5 mL/min flow; ESI; positive ion mode; detection at 550 nm). HRMS (ESI) calcd for C73H77F4N4O17 $[M+H]^+$ 1357.5220, found 1357.5232.

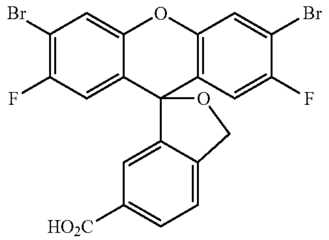 [SMILES: O=C(O)c1ccc2c(c1)C1(OC2)c2cc(F)c(Br)cc2Oc2cc(Br)c(F)cc21]

3',6'-dibromo-2',7'-difluoro-3H-spiro[isobenzofuran-1,9'-xanthene]-6-carboxylic acid (33). 2',7'-Fluoro-6-carboxyfluorescein dibromide (22, 420 mg, 0.78 mmol) was taken in 60 mL 5:1 isopropanol/THF mixture and cooled to 0° C., and LiBH4 (4.9 mL of 2.0 M solution in THF, 9.8 mmol, 12.5 equiv) was added dropwise. The reaction was stirred at room temperature for 8 h, before being diluted with saturated NH4Cl(aq) and extracted with CH2Cl2 (2×). The combined organic extracts were dried over MgSO4 (s), filtered, and concentrated under reduced pressure. Purification by silica gel chromatography (0-3% MeOH/CH2Cl2, linear gradient) afforded 33 (222 mg, 54%) as a white solid. $^1$H NMR (CD3OD, 400 MHZ) δ 8.94 (d, J=1.8 Hz, 1H), 8.09 (dd, J=8.1, 1.8 Hz, 1H), 7.71 (d, J=8.0 Hz, 1H), 7.57 (d, $^4$JHF=5.8 Hz, 2H), 6.75 (d, $^3$JHF=8.8 Hz, 2H), 3.78 (s, 2H). $^{13}$C NMR (101 MHz, CD3OD) δ 170.0 (C), 156.6 (d, $^1$JCF=242.5 Hz, CF), 147.5 (d, $^4$JCF=2.5 Hz, C), 145.1 (C), 142.9 (C), 130.8 (CH), 130.3 (C), 128.4 (CH), 127.3 (d, $^3$JCF=6.0 Hz, CH), 122.3 (CH), 116.4 (d, $^2$JCF=25.0 Hz, CH), 110.6 (d, $^2$JCF=23.5 Hz, C), 69.3 (C), 61.6 (CH2). $^{19}$F NMR (CD3OD, 376 MHZ) δ −115.79 (dd, $^3$JHF=8.9, $^4$JHF=6.1 Hz). HRMS (ESI) calcd for C21H11Br2F2O4, $[M+H]^+$ 522.8992, found 522.8994.

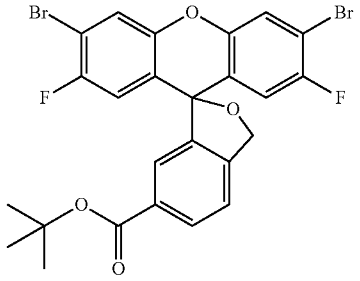 [SMILES: CC(C)(C)OC(=O)c1ccc2c(c1)C1(OC2)c2cc(F)c(Br)cc2Oc2cc(Br)c(F)cc21]

tert-Butyl 3',6'-dibromo-2',7'-difluoro-3H-spiro[isobenzofuran-1,9'-xanthene]-6-carboxylate (34). A suspension of 3',6'-dibromo-2',7'-difluoro-3H-spiro[isobenzofuran-1,9'-xanthene]-6-carboxylic acid (33, 125 mg, 0.24 mmol) in toluene was heated to 80° C. and N,N-dimethylformamide di-tert-butyl acetal (23, 480 μL, 2.4 mmol, 10 equiv) was added dropwise. The reaction was stirred at 80° C. for 15 min. After cooling the mixture to room temperature, it was diluted with saturated $NaHCO_3$(aq) and extracted with CH2Cl2 (2×). The combined organic extracts were dried ($MgSO_4$), filtered, and concentrated under reduced pressure. Flash chromatography (0-50% $CH_2Cl_2$/hexanes, linear gradient) provided 34 as a white solid (87 mg, 63%). $^1$H NMR (CDCl3, 400 MHZ) δ 8.05 (dd, J=7.9, 1.5 Hz, 1H), 7.47 (d, J=5.7 Hz, 2H), 7.45-7.41 (m, 2H), 6.72 (d, 3JHF=8.5 Hz, 2H), 5.41 (s, 2H), 1.54 (s, 9H). $^{13}$C NMR (CDCl3, 101 MHz) δ 164.9 (C), 155.5 (d, 1JCF=243.7 Hz, CF), 146.4 (C), 144.2 (C), 142.4 (C), 133.5 (C), 130.7 (CH), 124.7

(CH), 124.2 (d, 3JCF=6.1 Hz, C), 121.7 (CH), 121.3 (CH), 115.0 (d, 2JCF=24.7 Hz, CH), 110.5 (d, JCF=23.3 Hz, C), 81.9 (CH2), 73.2 (C), 28.3 (CH3). 19F NMR (CDCl3, 376 MHz) δ −113.82 (dd, 3JFH=8.5 Hz, 4JFH=5.8 Hz). HRMS (ESI) calcd for C25H19Br2F2O4 [M+H]+ 578.9618, found 578.9619.

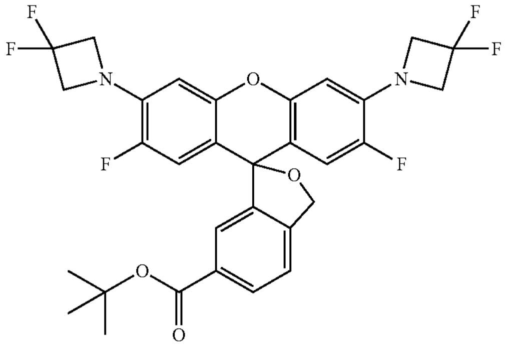 [SMILES: CC(C)(C)OC(=O)c1ccc2c(c1)C1(OC2)c2cc(F)c(N3CC(F)(F)C3)cc2Oc2cc(N3CC(F)(F)C3)c(F)cc21]

tert-Butyl 3',6'-bis(3,3-difluoroazetidin-1-yl)-2',7'-difluoro-3H-spiro[isobenzofuran-1,9'-xanthene]-6-carboxylate (35). The title compound was prepared from dibromide 34 and 3,3-difluoroazetidine hydrochloride (29) following the C—N cross-coupling method described for 9 (64%, white solid). $^{1}$H NMR (CDCl3, 400 MHz) δ 8.02 (dd, J=7.9, 1.5 Hz, 1H), 7.48 (d, J=1.3 Hz, 1H), 7.40 (d, J=7.9 Hz, 1H), 6.48 (d, $^{3}$JHF=12.4 Hz, 2H), 6.26 (d, $^{4}$JHF=7.7 Hz, 2H), 5.30 (s, 2H), 4.32 (td, $^{3}$JHF=11.9, $^{5}$JHF=2.1 Hz, 8H), 1.54 (s, 9H). $^{13}$C NMR (CDCl3, 101 MHZ) δ 165.3 (C), 147.7 (d, $^{1}$JCF=238.6 Hz, CF), 147.1 (d, $^{4}$JCF=1.1 Hz, C), 144.7 (C), 143.4 (C), 133.2 (C), 130.1 (CH), 125.2 (CH), 121.0 (CH), 115.0 (d, $^{2}$JCF=21.1 Hz, CH), 114.4 (d, $^{3}$JCF=6.1 Hz, C), 101.9 (d, $^{3}$JCF=3.7 Hz, CH), 83.7 (C), 81.6 (C), 72.0 (CH2), 64.5 (td, $^{2}$JCF=26.0, $^{4}$JCF=2.1 Hz, CH2), 28.3 (CH3). $^{19}$F NMR (CDCl3, 376 MHZ) δ −100.67 (p, $^{3}$JHF=12.0 Hz, 4F), −137.90 (ddd, $^{3}$JFH=12.6, $^{4}$JFH=7.7, $^{5}$JFH=2.1 Hz, 2F). HRMS (ESI) calcd for C31H27F6N2O4, [M+H]$^{+}$ 605.1870, found 605.1875.

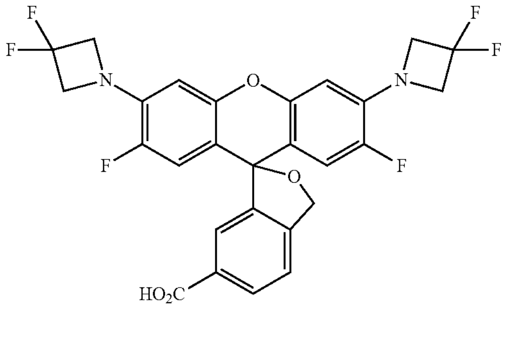 [SMILES: O=C(O)c1ccc2c(c1)C1(OC2)c2cc(F)c(N3CC(F)(F)C3)cc2Oc2cc(N3CC(F)(F)C3)c(F)cc21]

6-Carboxy-hydroxymethyl-JF526 (6-carboxy-HM-JF526, 36). Ester 35 (25 mg, 33 μmol) was dissolved in CH2Cl2 (2.5 mL), and trifluoroacetic acid (0.5 mL) was added. The reaction was stirred at room temperature for 1 h. Toluene (3 mL) was added and the reaction mixture was concentrated under reduced pressure. The residue was dissolved in MeOH after which $Na_2CO_3$ (50 mg) was added, and the reaction was stirred at room temperature for 1 h, filtered, and concentrated under reduced pressure. Flash chromatography on silica gel (2-70% EtOAc/hexanes, linear gradient) afforded 36 as a light pink solid (13 mg, 72%). $^{1}$H NMR (DMSO-d6, 400 MHZ) δ 8.08 (dd, J=8.0, 1.4 Hz, $^{1}$H), 7.61 (d, J=7.9 Hz, $^{1}$H), 7.45 (s, 1H), 6.68 (d, 3JHF=12.6 Hz, 2H), 6.46 (d, 4JHF=7.8 Hz, 2H), 5.46 (s, 2H), 4.42 (td, 3JHF=12.1, 5JHF=2.1 Hz, 8H). 13C NMR (DMSO-d6, 101 MHz) δ 166.1 (C), 148.8 (d, 1JCF=237.2 Hz, CF), 146.7 (d, 4JCF=1.6 Hz, C), 145.9 (C), 143.8 (C), 139.0 (dt, 2JCF=13.4, 4JCF=2.7 Hz, C), 131.3 (C), 129.9 (CH), 124.4 (CH), 121.7 (CH), 119.5 (t, 1JCF=270.4 Hz, CF2), 115.1 (d, 3JCF=5.9 Hz, C), 114.4 (d, 2JCF=21.3 Hz, CH), 102.1 (d, 3JCF=3.7 Hz, CH), 83.0 (C), 72.2 (CH2), 64.0 (td, 2JCF=26.0, 4JCF=2.5 Hz, CH2). 19F NMR (DMSO-d6, 376 MHz) δ −100.37 (p, 3JFH=12.1 Hz, 4F), −137.16−−137.65 (m, 2F). HRMS (ESI) calcd for C27H19F6N2O4 [M+H]+ 549.1244, found 549.1249.

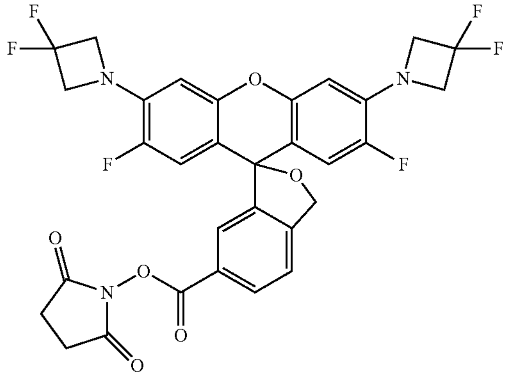 [SMILES: O=C(ON1C(=O)CCC1=O)c1ccc2c(c1)C1(OC2)c2cc(F)c(N3CC(F)(F)C3)cc2Oc2cc(N3CC(F)(F)C3)c(F)cc21]

HM-JF526-NHS (37). Acid 36 (13 mg, 23.7 μmol) was combined with TSTU (14 mg, 47 μmol, 2 eq) in DMF (1 mL), and DIEA (35 μL, 295 μmol, 9 eq) was added. After stirring the reaction at room temperature for 30 min, it was concentrated under reduced pressure. Flash chromatography on silica gel (5-60% EtOAc/hexanes, linear gradient) afforded 36 as a yellow solid (11.6 mg, 76%). $^{1}$H NMR ($CDCl_3$, 400 MHZ) δ 8.17 (dd, J=8.0, 1.6 Hz, 1H), 7.60 (d, J=1.4 Hz, 1H), 7.52 (dd, J=8.0, 0.8 Hz, 1H), 6.49 (d, $^{3}$JHF=12.2 Hz, 2H), 6.26 (d, $^{4}$JHF=7.7 Hz, 2H), 5.37 (s, 2H), 4.34 (td, $^{3}$JHF=11.8, $^{5}$JHF=2.0 Hz, 8H), 2.87 (d, J=6.5 Hz, 4H). $^{19}$F NMR (CDCl3, 376 MHz) δ −100.38 (p, $^{3}$JFH=12.1 Hz, 4F), −137.14−−137.31 (m, 2F). Analytical LC-MS: tR=12.99 min, 98% purity; (10-95% MeCN/H2O, linear gradient, with constant 0.1% v/v TFA additive; 20 min run; 1 mL/min flow; ESI; positive ion mode; detection at 550 nm). HRMS (ESI) calcd for C31H22F6N3O6 [M+H]$^{+}$ 646.1407, found 646.1419.

All publications, patents, and patent applications mentioned in this specification are herein incorporated by reference to the same extent as if each individual publication, patent, or patent application was specifically and individually indicated to be incorporated by reference, including the references set forth in the following list:

REFERENCES

1. Lavis, L. D.; Raines, R. T., Bright ideas for chemical biology. ACS Chem. Biol. 2008, 3 (3), 142-155.
2. Lavis, L. D.; Raines, R. T., Bright building blocks for chemical biology. ACS Chem. Biol. 2014, 9 (4), 855-866.
3. Baeyer, A., Ueber eine neue Klasse von Farbstoffen. Ber. Dtsch. Chem. Ges. 1871, 4, 555-558.

4. Ceresole, M. Production of new red coloring matter. U.S. Pat. No. 377,349, Jan. 31, 1888, 1888.
5. Haugland, R. P.; Spence, M. T. Z.; Johnson, I. D.; Basey, A., The handbook: a guide to fluorescent probes and labeling technologies, 10th ed. Molecular Probes: Eugene, OR, 2005.
6. Lavis, L. D., Teaching old dyes new tricks: biological probes built from fluoresceins and rhodamines. Annu. Rev. Biochem. 2017, 86, 825-843.
7. Liu, J. X.; Diwu, Z. J.; Leung, W. Y.; Lu, Y. X.; Patch, B.; Haugland, R. P., Rational design and synthesis of a novel class of highly fluorescent rhodamine dyes that have strong absorption at long wavelengths. Tetrahedron Lett. 2003, 44 (23), 4355-4359.
8. Kolmakov, K.; Belov, V.; Bierwagen, J.; Ringemann, C.; Mueller, V.; Eggeling, C.; Hell, S., Red-emitting rhodamine dyes for fluorescence microscopy and nanoscopy. Chemistry: A European Journal 2010, 16.
9. Arden-Jacob, J.; Frantzeskos, J.; Kemnitzer, N. U.; Zilles, A.; Drexhage, K. H., New fluorescent markers for the red region. Spectrochim. Acta, Part A 2001, 57 (11), 2271-2283.
10. Kolmakov, K.; Belov, V. N.; Wurm, C. A.; Harke, B.; Leutenegger, M.; Eggeling, C.; Hell, S. W., A versatile route to red-emitting carbopyronine dyes for optical microscopy and nanoscopy. Eur. J. Org. Chem. 2010, 2010 (19), 3593-3610.
11. Grimm, J. B.; Sung, A. J.; Legant, W. R.; Hulamm, P.; Matlosz, S. M.; Betzig, E.; Lavis, L. D., Carbofluoresceins and carborhodamines as scaffolds for high-contrast fluorogenic probes. ACS Chem. Biol. 2013, 8 (6), 1303-1310.
12. Koide, Y.; Urano, Y.; Hanaoka, K.; Terai, T.; Nagano, T., Evolution of Group 14 rhodamines as platforms for near-infrared fluorescence probes utilizing photoinduced electron transfer. ACS Chem. Biol. 2011, 6, 600-608.
13. Egawa, T.; Hanaoka, K.; Koide, Y.; Ujita, S.; Takahashi, N.; Ikegaya, Y.; Matsuki, N.; Terai, T.; Ueno, T.; Komatsu, T.; Nagano, T., Development of a far-red to near-infrared fluorescence probe for calcium ion and its application to multicolor neuronal imaging. J. Am. Chem. Soc. 2011, 133 (36), 14157-14159.
14. Lukinavičius, G.; Umezawa, K.; Olivier, N.; Honigmann, A.; Yang, G.; Plass, T.; Mueller, V.; Reymond, L.; Corrêa Jr, I. R.; Luo, Z. G.; Schultz, C.; Lemke, E. A.; Heppenstall, P.; Eggeling, C.; Manley, S.; Johnsson, K., A near-infrared fluorophore for live-cell super-resolution microscopy of cellular proteins. Nat. Chem. 2013, 5, 132-139.
15. Grimm, J. B.; English, B. P.; Chen, J.; Slaughter, J. P.; Zhang, Z.; Revyakin, A.; Patel, R.; Macklin, J. J.; Normanno, D.; Singer, R. H.; Lionnet, T.; Lavis, L. D., A general method to improve fluorophores for live-cell and single-molecule microscopy. Nat. Methods 2015, 12 (3), 244-250.
16. Zhou, X.; Lai, R.; Beck, J. R.; Li, H.; Stains, C. I., Nebraska red: a phosphinate-based near-infrared fluorophore scaffold for chemical biology applications. Chem. Commun. 2016, 52 (83), 12290-12293.
17. Chai, X.; Cui, X.; Wang. B.; Yang, F.; Cai, Y.; Wu, Q.; Wang, T., Near-infrared phosphorus-substituted rhodamine with mission wavelength above 700 nm for bioimaging. Chem. Eur. J. 2015, 21 (47), 16754-16758.
18. Grimm, J. B.; Muthusamy, A. K.; Liang, Y.; Brown, T. A.; Lemon, W. C.; Patel, R.; Lu, R.; Macklin, J. J.; Keller, P. J.; Ji, N.; Lavis, L. D., A general method to fine-tune fluorophores for live-cell and in vivo imaging. Nat. Methods 2017, 14 (10), 987-994.
19. Grimm, J. B.; Heckman, L. M.; Lavis, L. D., The chemistry of small-molecule fluorogenic probes. Prog. Mol. Biol. Transl. Sci. 2013, 113, 1-34.
20. Li, X.; Gao, X.; Shi, W.; Ma, H., Design strategies for water-soluble small molecular chromogenic and fluorogenic probes. Chem. Rev. 2014, 114 (1), 590-659.
21. Spahn, C.; Grimm, J. B.; Lavis, L. D.; Lampe, M.; Heilemann, M., Whole-cell, 3D, and multicolor STED imaging with exchangeable fluorophores. Nano Lett. 2019, 19 (1), 500-505.
22. Reichardt, C., Solvatochromic dyes as solvent polarity indicators. Chem. Rev. 1994, 94 (8), 2319-2358.
23. Han, J.; Burgess, K., Fluorescent indicators for intracellular pH. Chem. Rev. 2010, 110 (5), 2709-2728.
24. Lavis, L. D.; Rutkoski, T. J.; Raines, R. T., Tuning the pKa of fluorescein to optimize binding assays. Anal. Chem. 2007, 79 (17), 6775-6782.
25. Shieh, P.; Dien, V. T.; Beahm, B. J.; Castellano, J. M.; Wyss-Coray, T.; Bertozzi, C. R., CalFluors: A universal motif for fluorogenic azide probes across the visible spectrum. J. Am. Chem. Soc. 2015, 137 (22), 7145-7151.
26. Sun, X.; Zhang, A.; Baker, B.; Sun, L.; Howard, A.; Buswell, J.; Maurel, D.; Masharina, A.; Johnsson, K.; Noren, C. J.; Xu, M.-Q.; Corrêa Jr., I. R., Development of SNAP-tag fluorogenic probes for wash-free fluorescence imaging. ChemBioChem 2011, 12 (14), 2217-2226.
27. Lukinavičius, G.; Reymond, L.; D'Este, E.; Masharina, A.; Gottfert, F.; Ta, H.; Guther, A.; Fournier, M.; Rizzo, S.; Waldmann, H.; Blaukopf, C.; Sommer, C.; Gerlich, D. W.; Arndt, H.-D.; Hell, S. W.; Johnsson, K., Fluorogenic probes for live-cell imaging of the cytoskeleton. Nat. Methods 2014, 11, 731-733.
28. Lukinavičius, G.; Blaukopf, C.; Pershagen, E.; Schena, A.; Reymond, L.; Derivery, E.; Gonzalez-Gaitan, M.; D'Este, E.; Hell, S. W.; Wolfram Gerlich, D.; Johnsson, K., SiR-Hoechst is a far-red DNA stain for live-cell nanoscopy. Nat. Commun. 2015, 6, 8497.
29. Brewer, T. F.; Chang, C. J., An aza-cope reactivity-based fluorescent probe for imaging formaldehyde in living cells. J. Am. Chem. Soc. 2015, 137 (34), 10886-10889.
30. Krishnamoorthy, L.; Cotruvo Jr, J. A.; Chan, J.; Kaluarachchi, H.; Muchenditsi, A.; Pendyala, V. S.; Jia, S.; Aron, A. T.; Ackerman, C. M.; Wal, M. N. V.; Guan, T.; Smaga, L. P.; Farhi, S. L.; New, E. J.; Lutsenko, S.; Chang, C. J., Copper regulates cyclic-AMP-dependent lipolysis. Nat. Chem. Biol. 2016, 12, 586.
31. Uno, S.-n.; Kamiya, M.; Yoshihara, T.; Sugawara, K.; Okabe, K.; Tarhan, M. C.; Fujita, H.; Funatsu, T.; Okada, Y.; Tobita, S., A spontaneously blinking fluorophore based on intramolecular spirocyclization for live-cell super-resolution imaging. Nat. Chem. 2014, 6 (8), 681-689.
32. Li, L.; Liu, H.; Dong, P.; Li, D.; Legant, W. R.; Grimm, J. B.; Lavis, L. D.; Betzig, E.; Tjian, R.; Liu, Z., Real-time imaging of Huntingtin aggregates diverting target search and gene transcription. eLife 2016, 5, e17056.
33. Wu, B.; Eliscovich, C.; Yoon, Y. J.; Singer, R. H., Translation dynamics of single mRNAs in live cells and neurons. Science 2016, 352 (6292), 1430-1435.
34. Lukinavicius, G.; Mitronova, G. Y.; Schnorrenberg, S.; Butkevich, A. N.; Barthel, H.; Belov, V. N.; Hell, S. W., Fluorescent dyes and probes for super-resolution microscopy of microtubules and tracheoles in living cells and tissues. Chem. Sci. 2018, 9 (13), 3324-3334.

35. Deumie, M.; El Baraka, M., Self-aggregation of R110 and R123 rhodamines with surfactants and phospholipid vesicles of negative charge: a qualitative fluorescence study. J. Photochem. Photobiol. A 1993, 74 (2), 255-266.
36. Ferguson, J.; Mau, A. W. H., Absorption studies of acid-base equilibria of dye solutions. Chem. Phys. Lett. 1972, 17 (4), 543-546.
37. Nagano, T.; Hanaoka, K.; Koide, Y.; Egawa, T.; Kushida, Y. Preparation of sila-anthracene analog and related compound as fluorescent probe. WO2012111818, 2012.
38. Grimm, J. B.; Lavis, L. D., Synthesis of rhodamines from fluoresceins using Pd-catalyzed C—N cross-coupling. Org. Lett. 2011, 13, 6354-6357.
39. Grimm, J. B.; English, B. P.; Choi, H.; Muthusamy, A. K.; Mehl, B. P.; Dong, P.; Brown, T. A.; Lippincott-Schwartz, J.; Liu, Z.; Lionnet, T.; Lavis, L. D., Bright photoactivatable fluorophores for single-molecule imaging. Nat. Methods 2016, 13, 985-988.
40. Abdelfattah, A. S.; Kawashima, T.; Singh, A.; Novak, O.; Liu, H.; Shuai, Y.; Huang, Y.-C.; Grimm, J. B.; Patel, R.; Friedrich, J.; Mensh, B. D.; Paninski, L.; Macklin, J. J.; Podgorski, K.; Lin, B.-J.; Chen, T.-W.; Turner, G. C.; Liu, Z.; Koyama, M.; Svoboda, K.; Ahrens, M. B.; Lavis, L. D.; Schreiter, E. R., Bright and photostable chemigenetic indicators for extended in vivo voltage imaging. bioRxiv 2018, 436840.
41. Grimm, J. B.; Brown, T. A.; Tkachuk, A. N.; Lavis, L. D., General synthetic method for Si-fluoresceins and Si-rhodamines. ACS Cent. Sci. 2017, 3 (9), 975-985.
42. Surry, D. S.; Buchwald, S. L., Dialkylbiaryl phosphines in Pd-catalyzed amination: a user's guide. Chem. Sci. 2011, 2 (1), 27-50.
43. Butkevich, A. N.; Bossi, M. L.; Lukinavičius, G.; Hell, S. W., Triarylmethane Fluorophores Resistant to Oxidative Photobluing. J. Am. Chem. Soc 2019, 141 (2), 981-989.
44. Miller, L. W.; Cai, Y.; Sheetz, M. P.; Cornish, V. W., In vivo protein labeling with trimethoprim conjugates: a flexible chemical tag. Nat. Methods 2005, 2 (4), 255.
45. Shao, L.; Kner, P.; Rego, E. H.; Gustafsson, M. G., Super-resolution 3D microscopy of live whole cells using structured illumination. Nat. Methods 2011, 8 (12), 1044.
46. Legant, W. R.; Shao, L.; Grimm, J. B.; Brown, T. A.; Milkie, D. E.; Avants, B. B.; Lavis, L. D.; Betzig, E., High-density three-dimensional localization microscopy across large volumes. Nat. Methods 2016, 13 (4), 359-365.
47. Klar, T. A.; Jakobs, S.; Dyba, M.; Egner, A.; Hell, S. W., Fluorescence microscopy with diffraction resolution barrier broken by stimulated emission. Proc. Natl. Acad. Sci. 2000, 97.
48. Chen, B.-C.; Legant, W. R.; Wang, K.; Shao, L.; Milkie, D. E.; Davidson, M. W.; Janetopoulos, C.; Wu, X. S.; Hammer, J. A.; Liu, Z., Lattice light-sheet microscopy: imaging molecules to embryos at high spatiotemporal resolution. Science 2014, 346 (6208), 1257998.
49. Uno, S.-n.; Kamiya, M.; Yoshihara, T.; Sugawara, K.; Okabe, K.; Tarhan, M. C.; Fujita, H.; Funatsu, T.; Okada, Y.; Tobita, S.; Urano, Y., A spontaneously blinking fluorophore based on intramolecular spirocyclization for live-cell super-resolution imaging. Nat. Chem. 2014, 6, 681.
50. Halabi, E. A.; Pinotsi, D.; Rivera-Fuentes, P., Photoregulated fluxional fluorophores for live-cell super-resolution microscopy with no apparent photobleaching. Nat. Commun. 2019, 10 (1), 1232.
51. Takakura, H.; Zhang, Y.; Erdmann, R. S.; Thompson, A. D.; Lin, Y.; McNellis, B.; Rivera-Molina, F.; Uno, S.-n.; Kamiya, M.; Urano, Y., Long time-lapse nanoscopy with spontaneously blinking membrane probes. Nat. Biotechnol. 2017, 35 (8), 773.
52. Liu, J.; Sun, Y.-Q.; Zhang, H.; Shi, H.; Shi, Y.; Guo, W., Sulfone-rhodamines: a new class of near-infrared fluorescent dyes for bioimaging. ACS Appl. Mater. Interfaces 2016, 8 (35), 22953-22962.
53. Enander, K.; Choulier, L.; Olsson, A. L.; Yushchenko, D. A.; Kanmert, D.; Klymchenko, A. S.; Demchenko, A. P.; Mély, Y.; Altschuh, D., A peptide-based, ratiometric biosensor construct for direct fluorescence detection of a protein analyte. Bioconjugate Chem. 2008, 19 (9), 1864-1870.
54. Deo, C.; Lavis, L. D., Synthetic and genetically encoded fluorescent neural activity indicators. Curr. Opin. Neurobiol. 2018, 50, 101-108.
55. MacNevin, C. J.; Watanabe, T.; Weitzman, M.; Gulyani, A.; Fuehrer, S.; Pinkin, N. K.; Tian, X.; Liu, F.; Jin, J.; Hahn, K. M., Membrane-permeant, environment-sensitive dyes generate biosensors within living cells. J. Am. Chem. Soc. 2019, 141 (18), 7275-7282.
56. Zheng, Q.; Ayala, A. X.; Chung, I; Weigel, A.V.; Ranjan, A.; Falco, N.; Grimm, J. B.; Tkachuk, A. N.; Wu, C.; Lippincott-Schwartz, J.; Singer, R. H.; Lavis, L. S., Rational Design of Fluorogenic and Spontaneously Blinking Labels for Super-Resolution Imaging. ACS Cent. Sci. 2019 (Sep. 5, 2019).
57. Suzuki, K.; Kobayashi, A.; Kaneko, S.; Takehira, K.; Yoshihara, T.; Ishida, H.; Shiina, Y.; Oishi, S.; Tobita, S. Reevaluation of absolute luminescence quantum yields of standard solutions using a spectrometer with an integrating sphere and a back-thinned CCD detector. Phys. Chem. Chem. Phys. 2009, 11, 9850-9860.
58. Schindelin, J.; Arganda-Carreras, I.; Frise, E.; Kaynig, V.; Longair, M.; Pietzsch, T.; Preibisch, S.; Rueden, C.; Saalfeld, S.; Schmid, B.; Tinevez, J. Y.; White, D. J.; Hartenstein, V.; Eliceiri, K.; Tomancak, P.; Cardona, A. Fiji: an open-source platform for biological-image analysis. Nat. Methods 2012, 9, 676-682.
59. Lu-Walther, H.-W.; Kielhorn, M.; Förster, R.; Jost, A.; Wicker, K.; Heintzmann R. fastSIM: a practical implementation of fast structured illumination microscopy. Methods Appl. Fluoresc. 2015, 3, 014001.
60. Whelan, D. R.; Bell, T. D. M. Image artifacts in Single Molecule Localization Microscopy: Why optimization of sample preparation protocols matters. Sci. Rep. 2015, 5, 7924.
61. Los, G. V.; Encell, L. P.; McDougall, M. G.; Hartzell, D. D.; Karassina, N.; Zimprich, C.; Wood, M. G.; Learish, R.; Ohana, R. F.; Urh, M.; Simpson, D.; Mendez, J.; Zimmerman, K.; Otto, P.; Vidugiris, G.; Zhu, J.; Darzins, A.; Klaubert, D. H.; Bulleit, R. F.; Wood, K. V. HaloTag: A novel protein labeling technology for cell imaging and protein analysis. ACS Chem. Biol. 2008, 3, 373-382.
62. Calloway, N. T.; Choob, M.; Sanz, A.; Sheetz, M. P.; Miller, L. W.; Cornish, V. W. Optimized fluorescent trimethoprim derivatives for in vivo protein labeling. ChemBioChem 2007, 8, 767-774.
63. Nakamura, A.; Takigawa, K.; Kurishita, Y.; Kuwata, K.; Ishida, M.; Shimoda, Y.; Hamachi, I.; Tsukiji, S. Hoechst tagging: a modular strategy to design synthetic fluorescent probes for live-cell nucleus imaging. Chem. Commun. 2014, 50, 6149-6152.
64. U.S. Pat. No. 9,933,417
65. U.S. Pat. No. 9,933,417

66. U.S. Pat. No. 10,018,624
67. U.S. Pat. No. 10,161,932
68. U.S. Pat. No. 10,495,632

It will be understood that various details of the presently disclosed subject matter can be changed without departing from the scope of the subject matter disclosed herein. Furthermore, the foregoing description is for the purpose of illustration only, and not for the purpose of limitation.

What is claimed is:

1. A compound of the formula:

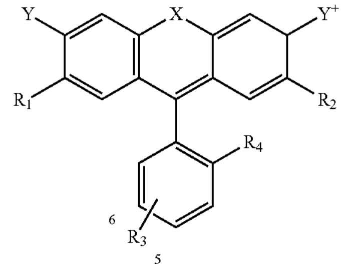

or a closed form thereof, wherein (a) X is selected from the group consisting of O, N-alkyl, S, and C(alkyl)$_2$;

Y is —$NH_2$ or

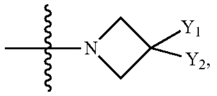

wherein each $Y_1$ and $Y_2$ is each independently selected from the group consisting of H, F, CN, $OCH_3$, $SO_2CH_3$, $CF_3$, $CH_3$, and $CO_2H$;

$R_1$ and $R_2$ are each independently selected from the group consisting of H, alkyl, and halogen;

$R_3$, which can be a substitution at either the 5 position or the 6 position of the ring to which it is bound, is selected from the group consisting of H, self-labeling protein tag ligand, $CO_2H$, $CO_2CH_3$, $CO_2$t-Bu, N-hydroxysuccinimidyl (NHS) ester, and a targeting moiety; and $R_4$ is $CH_2OH$;

(b) X is Si(alkyl)$_2$;

Y is —$NH_2$;

$R_1$ and $R_2$ are each independently selected from the group consisting of H, alkyl, and halogen;

$R_3$, which can be a substitution at either the 5 position or the 6 position of the ring to which it is bound, is selected from the group consisting of H, self-labeling protein tag ligand, $CO_2H$, $CO_2CH_3$, $CO_2$t-Bu, NHS ester, and a targeting moiety; and $R_4$ is $CH_2OH$;

(c) X is Si(alkyl)$_2$;

Y is

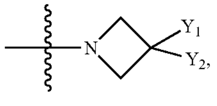

wherein each $Y_1$ and $Y_2$ is each independently selected from the group consisting of F, CN, $OCH_3$, $SO_2CH_3$, $CF_3$, $CH_3$, and $CO_2H$;

$R_1$ and $R_2$ are each independently selected from the group consisting of H, alkyl, and halogen;

$R_3$, which can be a substitution at either the 5 position or the 6 position of the ring to which it is bound, is selected from the group consisting of H, self-labeling protein tag ligand, $CO_2H$, $CO_2CH_3$, $CO_2$t-Bu, NHS ester, and a targeting moiety; and $R_4$ is $CH_2OH$;

(d) X is Si(alkyl)$_2$;

Y is

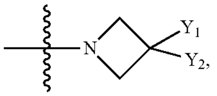

wherein $Y_1$ and $Y_2$ are H;

$R_1$ and $R_2$ are each independently selected from the group consisting of alkyl, and halogen;

$R_3$, which can be a substitution at either the 5 position or the 6 position of the ring to which it is bound, is selected from the group consisting of H, self-labeling protein tag ligand, $CO_2H$, $CO_2CH_3$, $CO_2$t-Bu, NHS ester, and a targeting moiety; and $R_4$ is $CH_2OH$; or (e) X is Si(alkyl)$_2$;

Y is

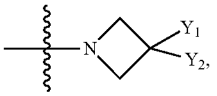

wherein $Y_1$ and $Y_2$ are H;

$R_1$ and $R_2$ are H;

$R_3$, which can be a substitution at either the 5 position or the 6 position of the ring to which it is bound, is selected from the group consisting of H, self-labeling protein tag ligand, $CO_2H$, $CO_2CH_3$, $CO_2$t-Bu, and a targeting moiety; and $R_4$ is $CH_2OH$.

2. The compound of claim 1, according to the following formula:

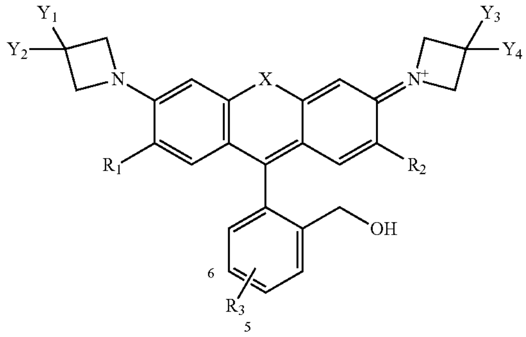

wherein $Y_1$-$Y_4$ are each independently selected from the group consisting of H, F, CN, $OCH_3$, $SO_2CH_3$, $CF_3$, $CH_3$, and $CO_2H$;

X is selected from the group consisting of O, N-alkyl, S, Si(alkyl)$_2$, and C(alkyl)$_2$;

$R_1$ and $R_2$ are each independently selected from the group consisting of H, alkyl, and halogen; and $R_3$, which can be a substitution at either the 5 position or the 6 position, is selected from the group consisting of H, self-labeling protein tag ligand, $CO_2H$, $CO_2CH_3$, $CO_2$t-Bu, and a targeting moiety.

3. The compound of claim 1, according to the following formula:

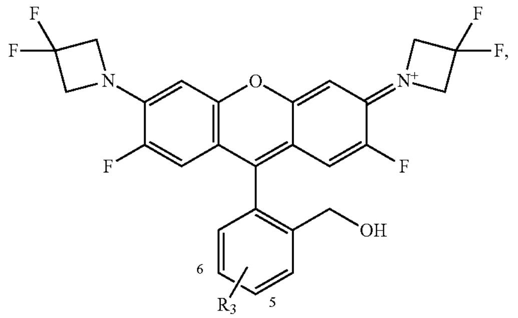

wherein $R_3$, which can be a substitution at either the 5 position or the 6 position, is selected from the group consisting of H, self-labeling protein tag ligand, $CO_2H$, $CO_2CH_3$, $CO_2$t-Bu, N-hydroxysuccinimidyl (NHS) ester, and a targeting moiety.

4. The compound of claim 1, according to the following formula:

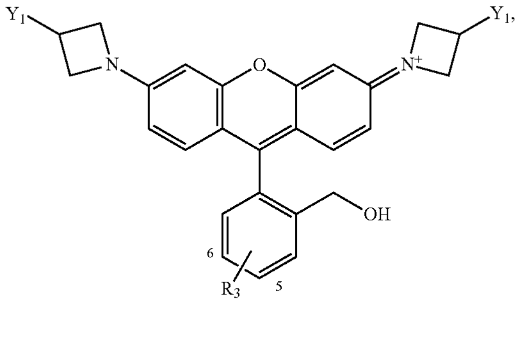

wherein, $R_3$, which can be a substitution at either the 5 position or the 6 position, is selected from the group consisting of H, self-labeling protein tag ligand, $CO_2H$, $CO_2CH_3$, $CO_2$t-Bu, N-hydroxysuccinimidyl (NHS) ester, and a targeting moiety; and $Y_1$ is H, F, CN, $OCH_3$, $SO_2CH_3$, or $CF_3$.

5. The compound of claim 1, according to the following formula:

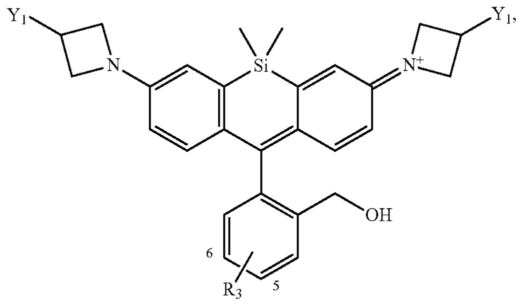

wherein $R_3$, which can be a substitution at either the 5 position or the 6 position, is selected from the group consisting of H, self-labeling protein tag ligand, $CO_2H$, $CO_2CH_3$, $CO_2$t-Bu, N-hydroxysuccinimidyl (NHS) ester, and a targeting moiety; and $Y_1$ is F, CN, $OCH_3$, $SO_2CH_3$, or $CF_3$.

6. The compound of claim 1, according to the following formula:

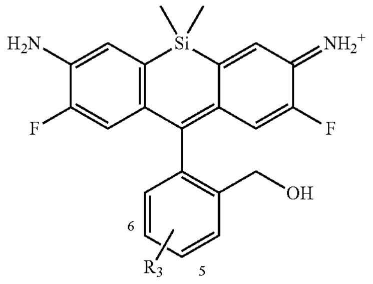

or

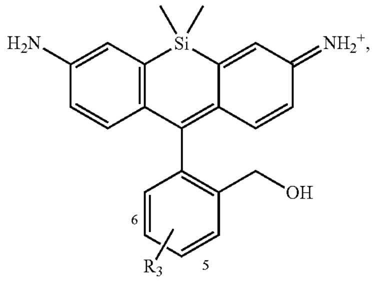

wherein $R_3$, which can be a substitution at either the 5 position or the 6 position, is selected from the group consisting of H, self-labeling protein tag ligand, $CO_2H$, $CO_2CH_3$, $CO_2$t-Bu, N-hydroxysuccinimidyl (NHS) ester, and a targeting moiety.

7. The compound of claim 1, according to a formula selected from the group consisting of:

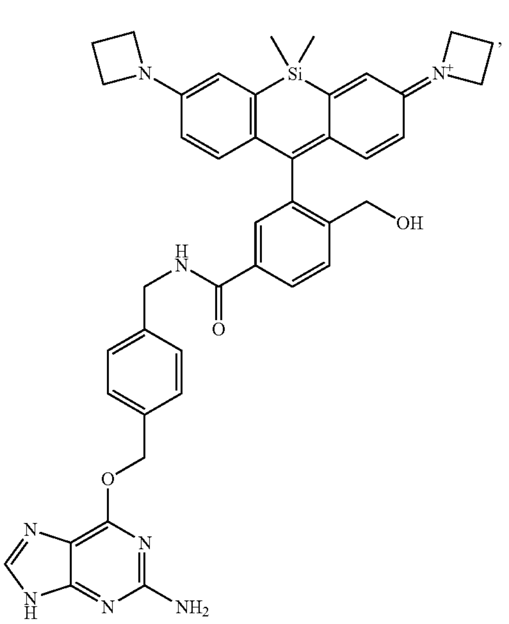
,
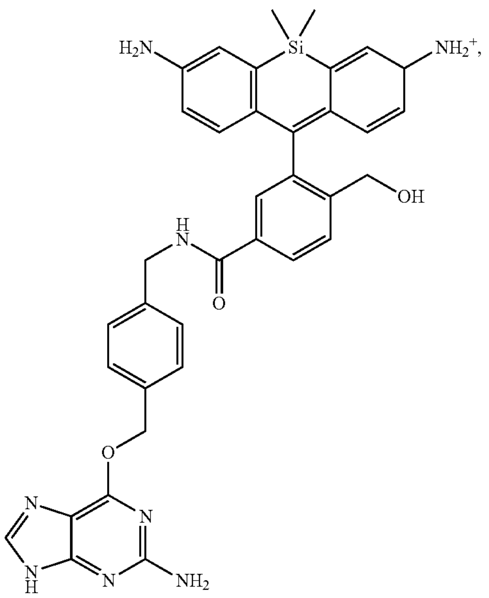
,
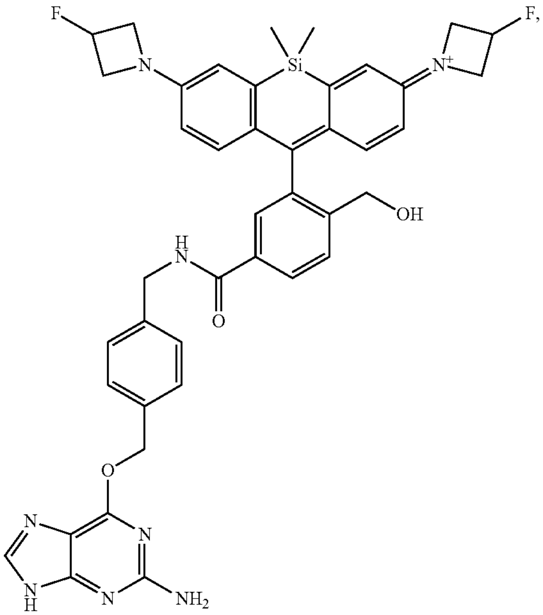
,
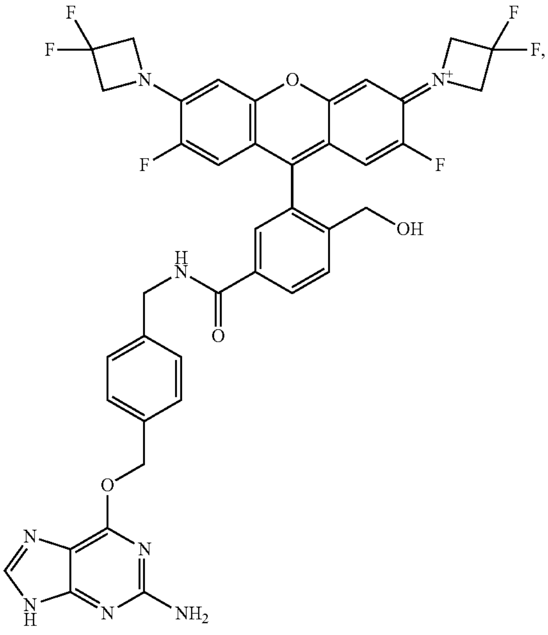
,
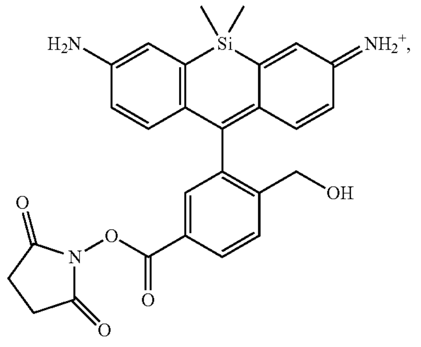
,

-continued
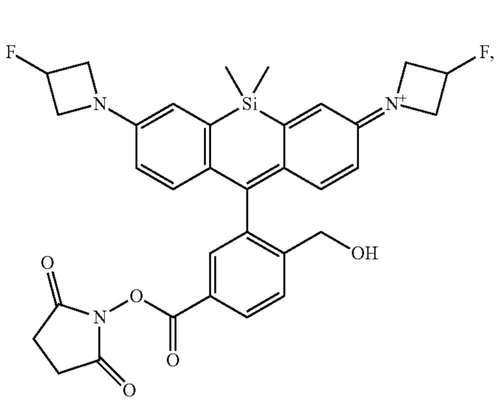
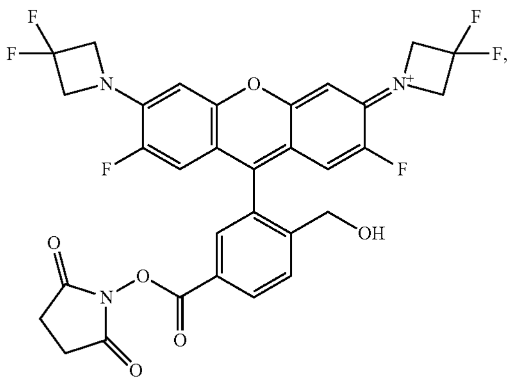
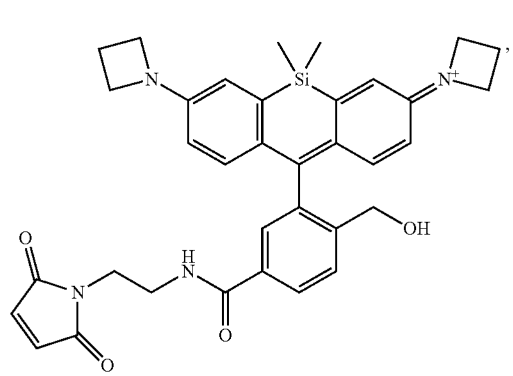
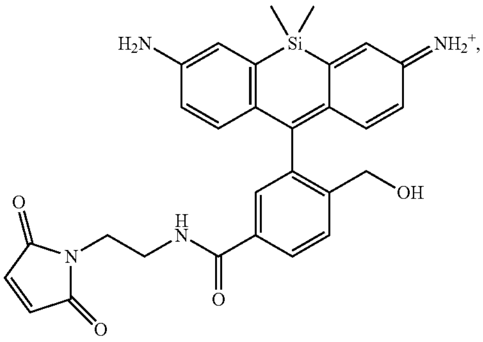
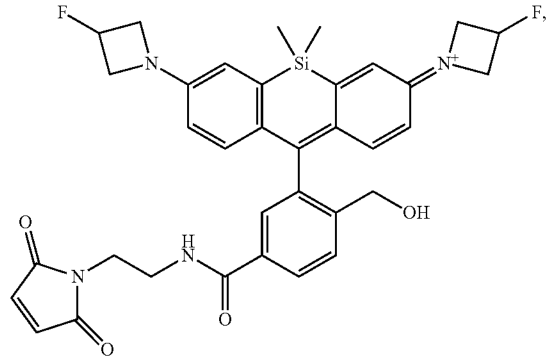
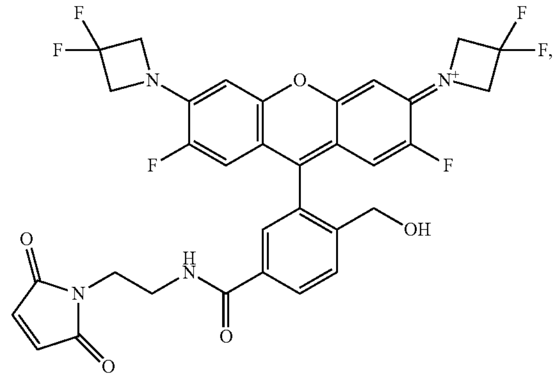
and
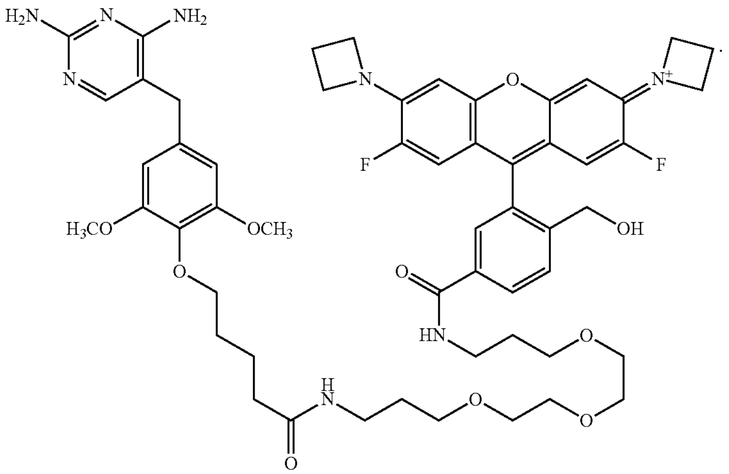

8. The compound of claim 1, wherein $R_3$ is a targeting moiety that is a self-labeling protein tag ligand.

9. The compound of claim 1, wherein $R_3$ is a targeting moiety for directing the compound to DNA, microtubules, or lysosomes.

10. The compound of claim 1, wherein $R_3$ is a targeting moiety selected from the group consisting of trimethoprim, Taxol, Hoechst, and pepstatin A.

11. A method for detecting a target substance, comprising:

contacting a sample with the compound of claim 1; and detecting an emission light from the compound, the emission light indicating the presence of the target substance.

12. The method of claim 11, wherein the target substance is selected from a protein, a carbohydrate, a polysaccharide, a glycoprotein, a hormone, a receptor, an antigen, an antibody, a virus, a substrate, a metabolite, an inhibitor, a drug, a nutrient, a growth factor, a lipoprotein, and a combination thereof.

13. The method of claim 11, wherein the detecting step is performed with a microscope.

14. The method of claim 11, further comprising a step of exposing the compound to an absorption light that includes a wavelength of about 100 nm to about 1000 nm.

15. The method of claim 11, wherein the contacting step and the detecting step are performed in a live cell.

16. The method of claim 11, wherein:

the compound includes a first compound and a second compound;

the first compound being selective for a first target substance and capable of emitting a first emission light;

the second compound being selective for a second target substance and capable of emitting a second emission light, and the detecting step includes detecting the first emission light that indicates the presence of the first target substance and the second emission light that indicates the presence of the second target substance.

17. The compound of claim 1, wherein

Y is

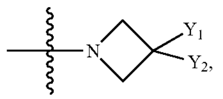

wherein $Y_1$ and $Y_2$ are selected from the group consisting of (a) $Y_1$ is $OCH_3$ and $Y_2$ is H, (b) $Y_1$ is F and $Y_2$ is H, (c) $Y_1$ is CN and $Y_2$ is H, (d) $Y_1$ is $SO_2CH_3$ and $Y_2$ is H, (d) $Y_1$ is $CF_3$ and $Y_2$ is H, and (e) $Y_1$ and $Y_2$ are F;

X is $Si(alkyl)_2$;

$R_1$ and $R_2$ are H;

$R_3$ is selected from the group consisting of H, self-labeling protein tag ligand, $CO_2H$, $CO_2CH_3$, $CO_2t$-Bu, N-hydroxysuccinimidyl (NHS) ester, and a targeting moiety; and $R_4$ is $CH_2OH$.

18. The compound of claim 17, wherein $R_3$ is a self-labeling protein tag ligand.

19. The compound of claim 17, wherein $R_3$ is selected from the group consisting of:

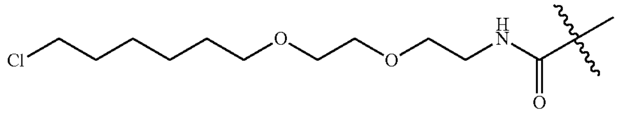

,

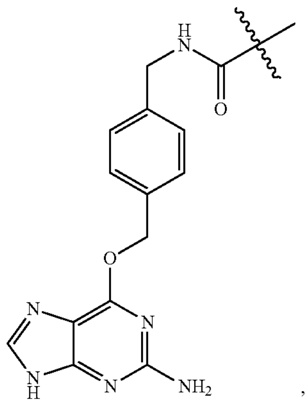

,

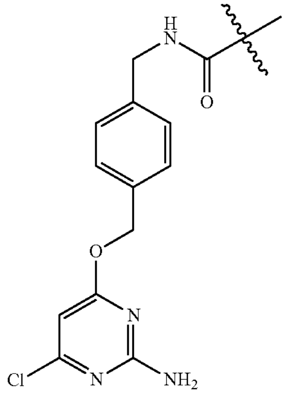

,

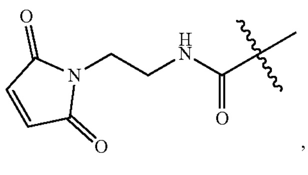

,

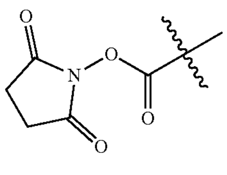

, and

-continued

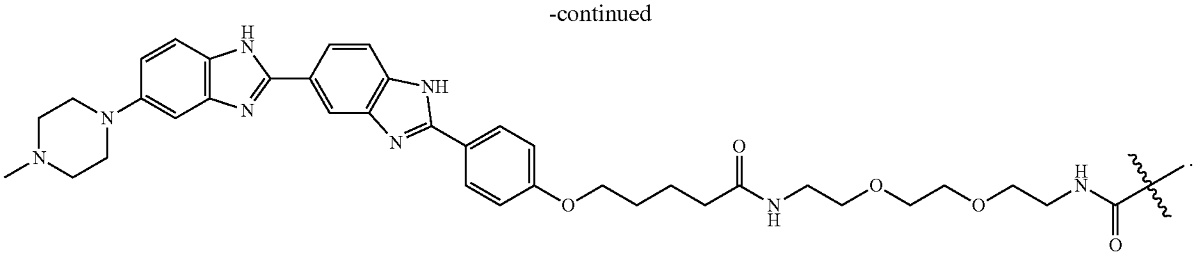

20. The compound of claim 1, wherein Y is $NH_2$; X is O; $R_1$ and $R_2$ are F; $R_3$ is selected from the group consisting of self-labeling protein tag ligand, $CO_2CH_3$, $CO_2$t-Bu, N-hydroxysuccinimidyl (NHS) ester, and a targeting moiety; and $R_4$ is $CO_2H$.

21. The compound of claim 20, wherein $R_3$ is a self-labeling protein tag ligand.

22. The compound of claim 20, wherein $R_3$ is selected from the group consisting of:

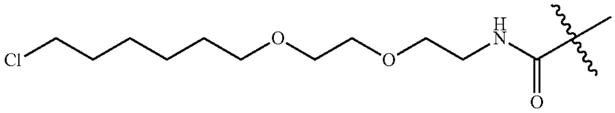

,

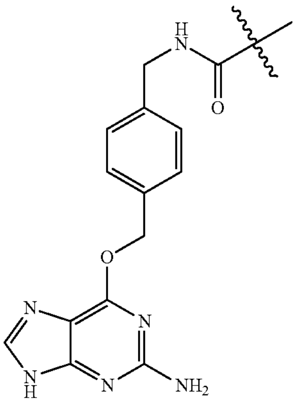

,

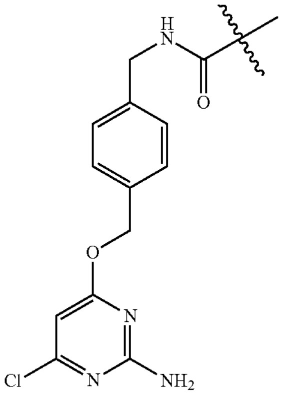

,

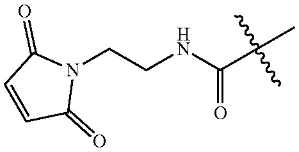

,

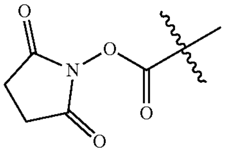

, and

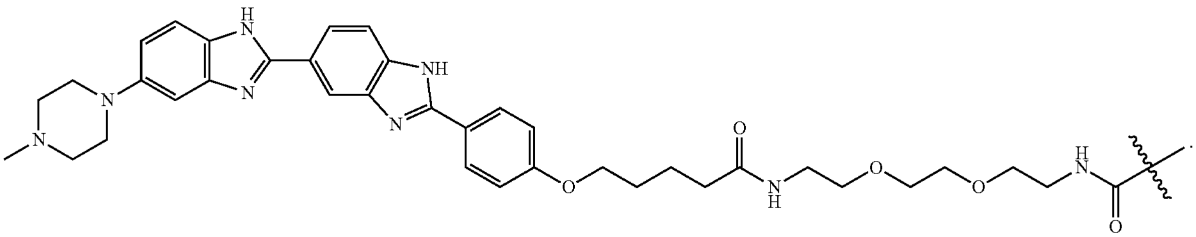

23. The compound of claim 1, wherein Y is

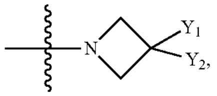

wherein $Y_1$ and $Y_2$ are selected from the group consisting of (a) $Y_1$ is $OCH_3$ and $Y_2$ is H, (b) $Y_1$ is F and $Y_2$ is H, (c) $Y_1$ is CN and $Y_2$ is H, (d) $Y_1$ is $SO_2CH_3$ and $Y_2$ is H, (d) $Y_1$ is $CF_3$ and $Y_2$ is H, and (e) $Y_1$ and $Y_2$ are F;

X is O, N-alkyl, S, and $C(alkyl)_2$;

$R_1$ and $R_2$ are H, alkyl, or halogen;

$R_3$ is selected from the group consisting of H, self-labeling protein tag ligand, $CO_2H$, $CO_2CH_3$, $CO_2$t-Bu, N-hydroxysuccinimidyl (NHS) ester, and a targeting moiety; and $R_4$ is $CH_2OH$.

24. The compound of claim 23, wherein $R_3$ is selected from the group consisting of:

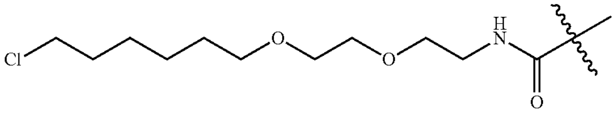

,

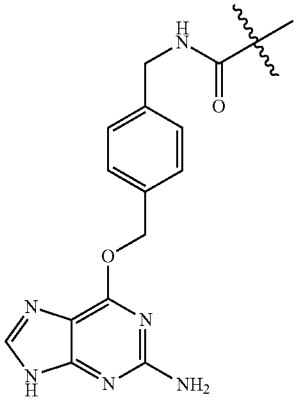

,

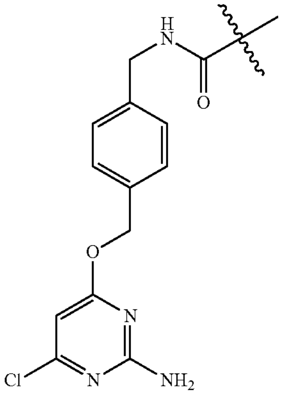

,

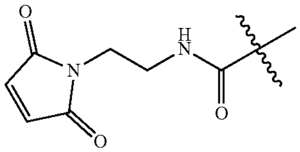

,

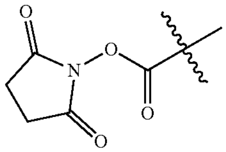

, and

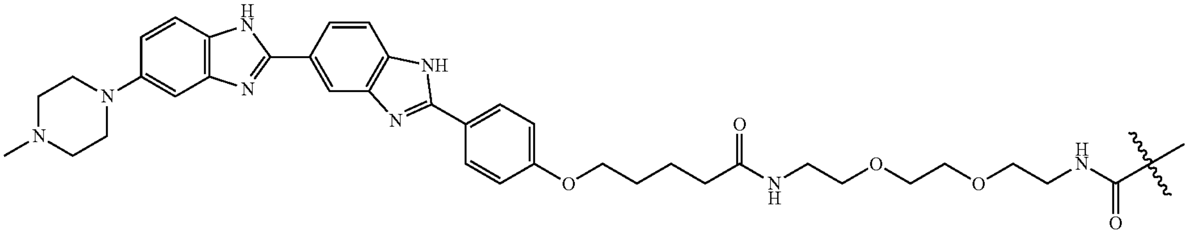

.

* * * * *